United States Patent [19]

Fray et al.

[11] Patent Number: 5,852,016
[45] Date of Patent: Dec. 22, 1998

[54] QUINOXALINE DERIVATIVES USEFUL IN THERAPY

[75] Inventors: Michael Jonathan Fray; Charles Eric Mowbray; Alan Stobie, all of Sandwich, United Kingdom

[73] Assignee: Pfizer Inc., New York, N.Y.

[21] Appl. No.: 809,337

[22] PCT Filed: Sep. 8, 1995

[86] PCT No.: PCT/EP95/03559

§ 371 Date: Mar. 21, 1997

§ 102(e) Date: Mar. 21, 1997

[87] PCT Pub. No.: WO96/09295

PCT Pub. Date: Mar. 28, 1996

[30] Foreign Application Priority Data

Sep. 24, 1994 [GB] United Kingdom ............ 9419318

[51] Int. Cl.⁶ .............. A01N 43/58; A61K 31/495
[52] U.S. Cl. .............. 514/249; 514/247; 514/248; 514/255; 544/349; 544/353; 544/354; 544/355; 544/356
[58] Field of Search .............. 514/255, 249, 514/248; 544/355, 356, 349, 353, 354

[56] References Cited

U.S. PATENT DOCUMENTS

| | | | |
|---|---|---|---|
| 4,889,855 | 12/1989 | Jacobsen et al. | 514/250 |
| 5,283,244 | 2/1994 | Sakamoto et al. | 514/249 |
| 5,385,903 | 1/1995 | Steppuhn et al. | 514/249 |
| 5,614,508 | 3/1997 | Nikam | 514/80 |

FOREIGN PATENT DOCUMENTS

| | | |
|---|---|---|
| 377112 | 7/1990 | Denmark . |
| 572852 | 5/1993 | Germany . |
| WO 94/00124 | 1/1994 | WIPO . |

*Primary Examiner*—Marianne M. Cintins
*Assistant Examiner*—Dwayne C. Jones
*Attorney, Agent, or Firm*—Peter C. Richardson; Paul H. Ginsburg

[57] ABSTRACT

Compounds of formula (I), wherein A represents N or CH; $R^1$ and $R^2$ independently represent $C_{1-4}$ alkyl, halo or $CF_3$; $R^3$ represents $C_{1-4}$ alkyl (optionally substituted), $C_{3-7}$ cycloalkyl, $CF_3$ or aryl; $R^4$ represents H, $C_{3-7}$ cycloalkyl or $C_{1-6}$ alkyl (optionally substituted); and their pharmaceutically acceptable derivatives; are useful in the treatment of, inter alia, neurodogenerative disorders.

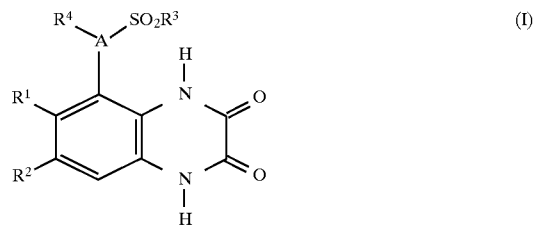

13 Claims, No Drawings

QUINOXALINE DERIVATIVES USEFUL IN THERAPY

This application is a 371 of PCT/EP95/03559 which was filed on Sep. 8, 1995.

BACKGROUND OF THE INVENTION

This invention relates to quinoxaline derivatives useful in therapy.

L-Glutamic acid is an excitatory amino acid neurotransmitter whose physiological role in the brain involves interaction with four receptors, three of which are named after the selective agonists NMDA (N-methyl-D-aspartate), AMPA (2-amino-3-hydroxy-5-methyl-4-isoxazolepropionic acid) and kainate. The fourth receptor is termed the metabotropic receptor. In addition to a binding site for glutamic acid, the NMDA receptor possesses high affinity binding sites for dissociative anaesthetics (e.g. ketamine), polyamines (e.g. spermine), glycine and certain metal ions (e.g. $Mg^{2+}$, $Zn^{2+}$). Since the NMDA receptor has an absolute requirement to bind glycine for activation to occur, glycine antagonists can act as functional NMDA antagonists.

In the region of a cerebral infarct, for example, anoxia causes abnormally high concentrations of glutamic acid to be released, which leads to an over-stimulation of NMDA receptors, resulting in the degeneration and death of neurones. Thus, NMDA receptor antagonists, which have been shown to block the neurotoxic effects of glutamic acid in vitro and in vivo, may be useful in the treatment and/or prevention of pathological conditions in which NMDA receptor activation is thought to be important. Examples of such conditions include neurodegenerative disorders including senile dementia and Alzheimer's disease and those arising from events such as stroke, transient ischaemic attack, peri-operative ischaemia and traumatic head injury to the brain or spinal cord. They may also have utility in conditions in which peripheral nerve function has been impaired such as retinal and macular degeneration.

Furthermore, NMDA antagonists have been shown to possess anti-convulsant and anxiolytic activity and may therefore be used to treat epilepsy and anxiety. They may also be useful in the treatment of pain.

NMDA antagonists may also attenuate the effects of alcohol withdrawal from physically dependent animals (K. A. Grant et al. J. Pharm. Exp. Ther. (1992), 260, 1017) and thus NMDA antagonists may be of use in the treatment of alcohol addiction.

Various derivatives of 1,2,3,4-tetrahydroquinoline-2,4-dione have been described as NMDA (glycine site) antagonists (see EP-A-0459561 and EP-A-0481676), while WO-A-91/13878 and JP-A-3220124 describe 1,4-dihydroquinoxalin-2,3-diones as glutamic acid antagonists. WO-A-94/00115 describes 1,4-dihydroquinoxalin-2,3-diones (including 6,7-dichloro-5-nitro-1,4-dihydroquinoxalin-2,3-dione) having high affinity for the glycine binding site with utility for treating stroke and related disorders.

SUMMARY OF THE INVENTION

According to the present invention, there is provided a compound of formula 1,

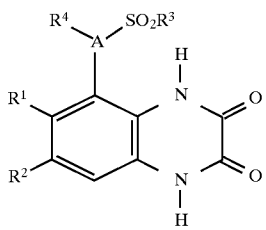

wherein
A represents N or CH;
$R^1$ and $R^2$ independently represent $C_{1-4}$ alkyl, halo or $CF_3$;
$R^3$ represents $C_{1-4}$ alkyl (optionally substituted by $C_{3-7}$ cycloalkyl or aryl), $C_{3-7}$ cycloalkyl, $CF_3$ or aryl;
$R^4$ represents H, $C_{3-7}$ cycloalkyl or $C_{1-6}$ alkyl [optionally substituted by OH, $C_{1-4}$ alkoxy, aryl (optionally substituted by up to 3 substituents independently selected from $C_{1-4}$ alkyl, $C_{1-4}$ alkoxy, halo and $CF_3$), heterocyclyl (optionally substituted by up to 3 substituents independently selected from $C_{1-4}$ alkyl, $C_{1-4}$ alkoxy, OH, halo, $CF_3$ and oxo and optionally benzo-fused), $C_{2-6}$ alkenyl, $C_{2-6}$ alkynyl, $C_{2-6}$ alkanoyl, $CO_2H$, $C_{1-4}$ alkoxycarbonyl, $NH_2$, $C_{1-4}$ alkylamino, di($C_{1-4}$ alkyl) amino, $NHSO_2CF_3$, $CONR^5R^6$, $NHCONR^5R^6$ or $O(CH_2)_n NR^5R^6$];
$R^5$ and $R^6$ independently represent H or $C_{1-4}$ alkyl, or taken together with the nitrogen atom to which they are attached they may represent a pyrrolidino, piperidino or morpholino group; and
n represents 2, 3 or 4;
or a pharmaceutically acceptable salt thereof (referred to together herein as "the compounds of the invention").

Pharmaceutically acceptable salts include salts of acidic or basic groups which may be present (for example sodium salts of carboxylic acid groups and hydrochloride salts of amino groups).

Preferably, A represents N.

"Halo" means fluoro, chloro, bromo or iodo. Preferred groups are fluoro, chloro and bromo.

Preferred groups which $R^1$ and $R^2$ independently represent are halo and $C_{1-4}$ alkyl. For example, they may both represent chlorine, or one may represent chlorine and the other may represent methyl or ethyl.

"Aryl" means an aromatic hydrocarbon such as naphthyl or more particularly phenyl.

Preferably, $R^3$ represents $C_{1-4}$ alkyl, more preferably methyl.

"Heterocyclyl" means an aromatic or non-aromatic heterocyclic group containing one or more heteroatoms each selected from O, S and N. It can be attached to the $C_1$–$C_6$ alkyl group by a nitrogen or more preferably a carbon atom. Heterocyclyl groups which may be mentioned are pyridinyl, imidazolyl, pyrimidinyl, pyrazolyl, triazolyl, pyrazinyl, tetrazolyl, furyl, thienyl, isoxazolyl and thiazolyl. Heterocyclyl groups having a fused benzene ring include benzimidazolyl.

Preferably, $R^4$ represents $C_{1-6}$ alkyl substituted by OH or $CO_2H$, more preferably it represents $CH_2CH_2OH$ or $CH_2CO_2H$.

Alkyl, alkoxy, alkenyl, alkynyl and alkanoyl groups, where appropriate, can be straight or branched.

Compounds of formula I in which an O or N atom in $R^4$ is connected to A via a single carbon atom may not be sufficiently stable to be used as drug compounds. Any such unstable compounds do not form part of the invention.

In some instances the compounds of the invention may exist as tautomers and all such tautomers are included within the scope of the invention, whether separated or not. In addition compounds containing asymmetric centres can exist as enantiomers and diastereoisomers, and the invention includes the separated individual isomers as well as mixtures of isomers.

In particular, rotation about the bond between A and the 1,4-dihydro-2,3-dioxoquinoxaline ring may be restricted, and so atropisomerism may arise. Preferably, when A represents N, $R^4$ is disposed above the plane of the paper and $SO_2R^3$ is disposed below the plane of the paper in formula I, as shown in formula IA below:

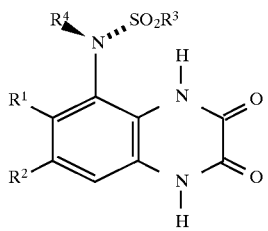

IA

The stereochemical assignment of this bond is (R) when $R^1$ represents Cl, and (S) when $R^1$ represents methyl, for example.

Optical isomers (including atropisomers) may be separated using conventional techniques such as fractional crystallization of diastereomeric derivatives [for example see Example 80(b)].

DETAILED DESCRIPTION OF THE INVENTION

There is further provided a process for the production of a compound of the invention, which comprises removing the protecting groups from a compound of formula II,

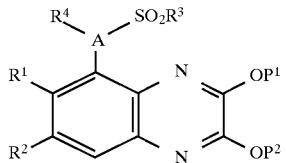

II wherein A and $R^{1-4}$ are as defined above and $P^1$ and $p^2$ are protecting groups for hydroxy groups attached to aromatic rings, and where desired or necessary converting the resulting compound into a pharmaceutically acceptable salt or vice versa. Protecting groups which $P^1$ and $p^2$ may represent include benzyl and $C_{1-6}$ alkyl, in particular methyl. These protecting groups may be removed using conventional deprotection methods (see 'Protective Groups in Organic Synthesis' by T W Greene and P G M Wuts, John Wiley and Sons Inc, 1991). For example, when they represent methyl, they may be removed by acidic hydrolysis using dilute aqueous hydrochloric acid (e.g. 2 molar). The reaction is typically carried out by heating the compound of formula II, preferably under reflux, in a mixture of dilute aqueous hydrochloric acid and a suitable organic solvent such as dioxane or acetone for, say, 2 to 48 hours until reaction is complete. The compound of the invention can then be isolated and purified by conventional procedures.

Compounds of formula II, as defined above, form a further aspect of the invention.

Compounds of formula II in which $R^4$ is other than hydrogen may be prepared by reaction of a corresponding compound of formula II in which $R^4$ is H with the appropriate halide of formula $R^{4a}X$, wherein X is Cl, Br or I, and $R^{4a}$ has the same significance as $R^4$ as defined above except that it cannot represent H, in the presence of a base such as potassium t-butoxide. Typically the base is added to a solution of the compound of formula II (in which $R^4$ represents H) in a suitable organic solvent such as dimethylformamide. After stirring for a few minutes, the halide $R^4X$ is added and the mixture stirred for a few hours at about room temperature [see e.g. Example 7 (a)]. The desired intermediate can then be isolated and purified by conventional procedures.

In addition, compounds of formula II can be prepared from other compounds of formula II using conventional methods. For example, compounds in which A is CH, and $R^4$ is allyl may be converted to compounds in which $R^4$ is 2-hydroxyethyl by ozonolysis followed by reduction. Compounds of formula II in which A is CH, and $R^4$ is allyl may also be prepared from corresponding compounds of formula II in which $R^4$ is H by reaction with diallyl carbonate (e.g. see Example 93).

As an alternative to the above alkylation procedure when A is N, the Mitsunobu reaction can be used. This involves the reaction of an alcohol of the formula $R^{4a}OH$ (in which $R^{4a}$ is as defined above) with diethyl azodicarboxylate, triphenylphosphine and a compound of formula II in which $R^4$ is H. The reaction is typically carried out in a suitable organic solvent, e.g. tetrahydrofuran, at about room temperature with stirring for, say, 6–12 hours [see e.g. Example 49 (a)].

Compounds of formula II in which $R^4$ is a $C_1$–$C_6$ alkyl group substituted by hydroxy can also be prepared by, or analogously to, the methods of Preparations 8 to 10, which involve the formation of an alkanoylalkyl derivative which is either reduced with e.g. diisobutylaluminium hydride or reacted with an alkylmagnesium halide.

Compounds of formula II in which $R^4$ is hydrogen and A is N can be prepared by sulphonylation of a corresponding quinoxaline of formula III,

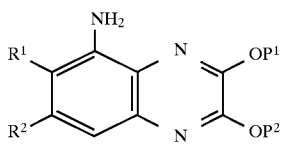

III in which $R^1$, $R^2$, $p^1$ and $p^2$ are as defined above, using an appropriate sulphonyl chloride $R^3SO_2Cl$ or anhydride of formula $(R^3SO_2)_2O$, in which $R^3$ is as defined above, in a suitable organic solvent, e.g. dichloromethane or tetrahydrofuran, in the presence of an acid acceptor such as pyridine (see e.g. Preparation 5) or triethylamine. With some starting materials, if a large excess of the sulphonyl chloride or anhydride is used, then di-sulphonylation or some degree of di-sulphonylation may occur. In this situation, one of the $R^3SO_2$— substituents can be removed by reaction of the di-sulphonylated product with aqueous sodium hydroxide (see e.g. Preparation 3). Compounds of formula III can be prepared by conventional techniques such as those illustrated in Preparations 1 and 2.

Compounds of formula II in which $R^4$ is hydrogen and A is CH may be prepared by reaction of a compound of formula IV,

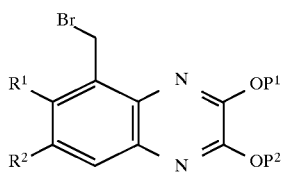

in which $R^1$, $R^2$, $p^1$ and $p^2$ are as defined above, with a thiolate of formula $NaSR^3$, in which $R^3$ is as defined above, followed by oxidation using a peracid such as 3-chloroperbenzoic acid (see for example Preparation 29). Compounds of formula IV may be prepared by conventional techniques (see for example Preparation 28).

In the synthesis of the compounds of the invention it may be necessary or desirable to protect sensitive functional groups and then deprotect them. Methods for such operations are known to those skilled in the art and are described in 'Protective Groups in Organic Synthesis' mentioned above.

The compounds of the invention are useful because they possess pharmacological activity in animals (including humans). In particular, the compounds are useful in the treatment or prevention of neurodegenerative disorders (including senile dementia, Alzheimer's disease and those arising from events such as stroke, transient ischaemic attack, peri-operative ischaemia and traumatic head injury to the brain or spinal cord; and retinal and macular degeneration), convulsions, pain and anxiety. The treatment of stroke is of particular interest.

Thus, according to another aspect of the invention, there is provided an anxiolytic, anticonvulsant, analgesic or neuroprotective method of treatment, which comprises administration of a compound of the invention to a patient in need of 8such treatment. The use of the compounds of the invention as pharmaceuticals, and the use of the compounds of the invention in the manufacture of an anxiolytic, anticonvulsant, analgesic or neuroprotective medicament, are also provided.

The biological activity of the compounds of the invention may be demonstrated in the tests set out below:

(a) Binding affinity for the glycine site of the NMDA receptor

This may be measured by testing a compound's ability to displace a selective glycine site radioligand from rat brain membranes as described in Brit J Pharm (1991), 104, 74. In a variation of this method, thoroughly washed membrane protein is incubated with [$^3$H]-L-689,560 for 90 minutes using tris-acetate buffer (pH 7.4). Displacement of the radioligand, using a range of test compound concentrations, is used to derive $IC_{50}$ (50% inhibitory concentration) values.

(b) Binding affinity for the AMPA receptor

This may be measured by testing a compound's ability to displace the radioligand [$^3$H]-AMPA from rat brain membranes. Membrane homogenate is incubated with radioligand (10 nM) in the presence or absence of test compounds at various concentrations at 4° C. for 45 min. Free and bound radiolabel is separated by rapid filtration, and radioactivity is measured by liquid scintillation counting.

(c) Functional in vitro NMDA antagonism

This is demonstrated by the ability of a compound to inhibit the depolarizations in rat cortical slices induced by NMDA, similar to the method described in J Med Chem, (1990), 33, 789 and Brit J Pharm (1985), 84, 381. In a variation of the procedure, the response to a standard concentration of NMDA is measured in the presence of a range of test compound concentration, and the results obtained are used to derive $IC_{50}$ (50% inhibitory concentration) values.

(d) NMDA antagonism in vivo

This can be demonstrated by the ability of a compound to inhibit NMDA-induced wild running in the mouse according to a variation of the method described in Brit J Pharm Proceedings Supplement (1992), 107, 58P. In this model, groups of mice are treated with test compounds at various doses prior to administration of NMDA (60 mg/kg i.v.). The latency of onset of wild running is recorded and the presence or absence of this behaviour used to determine an $ED_{50}$. Probit analysis is used to estimate a dose at which 50% of mice fail to display wild running by 10 minutes post NMDA administration.

(e) Blocking of cortical spreading depression

In vivo activity of a compound may also be demonstrated by measuring its ability to block the propagation of electrically-initiated cortical spreading depression in anaesthetised rats. Thus, male rats are anaesthetised and two glass microelectrodes are inserted into the right parietal cortex to a depth of 0.5–1 mm for recording brain activity. In addition, a bipolar stimulating electrode is placed on the dura in front of the microelectrodes. The dura is then electrically stimulated at 10 minute intervals, and the waves of spreading depression are detected by the microelectrodes, amplified and displayed using a chart recorder. Test compounds are dissolved in water as their sodium salts, or hydrochloride salts (where possible) and administered by i.v. injection at various doses to determine the minimum dose which blocks the propagation of the spreading depression.

The compounds of the invention may be administered to a patient in need of treatment by a variety of conventional routes of administration, including oral and intravenous administration. The compounds have potential for absorption through the gastrointestinal tract and thus administration by slow release formulations is also possible.

In general, a therapeutically-effective oral dose is likely to range from 0.1 to 100 mg/kg body weight of the subject to be treated, preferably 1 to 10 mg/kg, and an intravenous dose is likely to range from 0.01–10 mg/kg of body weight of subject treated, preferably 0.1–5 mg/kg. Where necessary, the compounds may also be administered by intravenous infusion, at a dose which is likely to range from 0.01–1 mg/kg/hr. In practice the physician will determine the actual dosage which will be most suitable for an individual patient and it will vary with age, weight and response of the particular patient. The above dosages are exemplary of the average case but there can, of course, be individual instances where higher or lower dosage ranges are merited, and such are within the scope of the invention.

Although the compounds of the invention can be administered alone, they will generally be administered in admixture with a pharmaceutical carrier selected with regard to the intended route of administration and standard pharmaceutical practice. For example, oral administration may be in the form of tablets containing such excipients as starch or lactose, in capsules either alone or in admixture with excipients, or in the form of elixirs or suspensions containing flavouring or colouring agents. The compounds may be injected parenterally, for example intravenously, intramuscularly or subcutaneously. For parenteral administration they are best used in the form of a sterile aqueous solution of an appropriate salt of the compound and the solution may contain other substances such as salts to make it isotonic with blood.

Thus, there is further provided a pharmaceutical formulation comprising a compound of the invention, in admixture with a pharmaceutically acceptable adjuvant, diluent or carrier.

The compounds of the invention may have the advantage that they are more potent, more soluble, more selective [for example being potent antagonists of the NMDA (glycine site) receptor but with little or no affinity for the AMPA receptor], less toxic or possess other more desirable properties than the compounds of the prior art.

The invention is illustrated by the following Examples. Intermediate compounds may be prepared as described in the following Preparations.

Melting points were determined using a Buchi apparatus in glass capillary tubes and are uncorrected. Spectroscopic data were recorded on Perkin-Elmer 983 (Infra Red), Fisons Trio 1000 (Mass Spectrometer, thermospray using ammonium acetate in aqueous methanol as carrier), and Bruker AC300 and Varian Unity 300 NMR instruments (both 300 MHz), and were consistent with the assigned structures. Column chromatography was accomplished on Kieselgel 60, (230–400 mesh) from E. Merck, Darmstadt. Kieselgel 60 $F_{254}$ plates from E. Merck were used for thin layer chromatography (TLC), and compounds were visualized with UV light or chloroplatinic acid/potassium iodide solution. In cases where compounds analyzed as hydrates, the presence of water was evident in the enhanced peak due to water in the proton NMR spectra. The purity of compounds was carefully assessed using analytical TLC and proton NMR (300 MHz), and the latter technique was used to calculate the amount of solvent in solvated samples. In multistep sequences, the purity and structure of intermediates were verified spectroscopically by proton NMR. Proton NMR shifts are quoted in parts per million downfield from tetramethylsilane.

Some abbreviations familiar to those skilled in the art have been used in the Examples and Preparations, e.g. Me (methyl), Et (ethyl), Ac (acetyl), h (hour), m (in relation to silica gel-mesh).

EXAMPLE 1

N-(1,4-Dihydro-6,7-dichloro-2,3-dioxoguinoxalin-5-yl)ethanesulphonamide

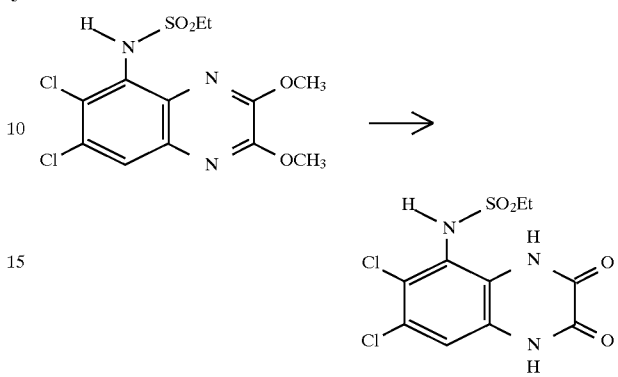

A mixture of N-(6,7-dichloro-2,3-dimethoxyquinoxalin-5-yl)ethanesulphonamide (Preparation 4) (100 mg, 0.273 mmol), 2M hydrochloric acid (2 ml) and dioxane (4 ml) was heated at reflux for 2.5 hours, cooled, and concentrated under reduced pressure. The solid residue was suspended in water, filtered off, and washed with water and ether to give the title compound (90 mg, 98%) as a white solid, m.p. 297° C. (dec.).

Analysis %:-Found: C, 33.97; H, 2.97; N, 11.68. $C_{10}H_9Cl_2N_3O_4S.H_2O$ requires C, 33.72; H, 3.11; N, 11.79%.

EXAMPLES 2–6

The following Examples, shown in Table 1 were prepared by the method of Example 1, using the corresponding 2,3-dimethoxyquinoxaline derivative (Preparations 3, 5 to 7 and 12).

TABLE 1

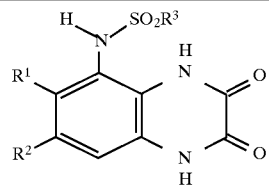

| Example | $R^1,R^2$ | $R^3$ | Yield | m.p. (°C.) | Formula | Analysis % Found (Required) C | H | N |
|---|---|---|---|---|---|---|---|---|
| 2 | —Cl | —$CH_3$ | 51% | >330 | $C_9H_7Cl_2N_3O_4S.H_2O$ | 31.33 (31.56 | 2.43 2.65 | 11.88 12.28) |
| 3 | —Cl | —Ph | 86% | >300 | $C_{14}H_9Cl_2N_3O_4S$ | 43.10 (43.54 | 2.16 2.35 | 10.75 10.88) |
| 4 | —$CH_3$ | —$CH_3$ | 88% | >300 | $C_{11}H_{13}N_3O_4S.0.15H_2O$ | 46.21 (46.20 | 4.78 4.69 | 14.46 14.69) |
| 5 | —$CH_3$ | —$CH_2CH_3$ | 97% | >315 | $C_{12}H_{15}N_3O_4S$ | 48.20 (48.48 | 4.94 5.09 | 13.61 14.13) |
| 6 | —$CH_3$ | —$CF_3$ | 84% | >300 | $C_{11}H_{10}F_3N_3O_4S.H_2O$ | 37.45 (37.19 | 3.37 3.40 | 11.83 11.83) |

EXAMPLE 7

N-(1,4-Dihydro-6,7-dichloro-2,3-dioxoquinoxaline-5-yl)-N-(methyl)-ethanesulphonamide

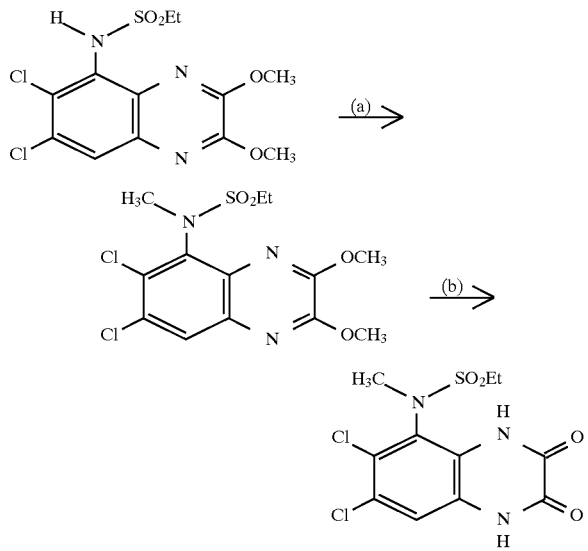

(a) Potassium tert-butoxide (67.5 mg, 1.1 mmol) was added to a stirred solution of N-(6,7-dichloro-2,3-dimethoxyquinoxalin-5-yl)ethanesulphonamide (Preparation 4) (200 mg, 0.55 mmol) in dry dimethylformamide (3 ml) under nitrogen at 20° C. After 5 minutes, methyl iodide (38 μl, 1.1 mmol) was added and the mixture was stirred at 20° C. for 2 hours. The mixture was concentrated under reduced pressure, partitioned between ethyl acetate and water, and the combined organic extracts were washed with dilute aqueous sodium hydroxide. The solution was dried ($MgSO_4$) and concentrated under reduced pressure. The residue was purified by flash chromatography (eluting with dichloromethane) to give N-(6,7-dichloro-2,3-dimethoxyquinoxalin-5-yl)-N-(methyl)ethanesulphonamide (150 mg, 79%).

$^1$H NMR (300 MHz, $CDCl_3$): δ=1.51 (3H, t, J7 Hz), 3.35 (3H,s) 3.37 (2H, q, J7 Hz), 4.14 (3H, s), 4.20 (3H,s), 7.92 (1H,s). m/z (thermospray) 380 ($MH^+$).

(b) A mixture of N-(6,7-dichloro-2,3-dimethoxyquinoxalin-5-yl)-N-(methyl)-ethanesulphonamide (150 mg, 0.39 mmol), 2M hydrochloric acid (4 ml) and dioxane (8 ml) was heated at reflux for 16 hours, cooled, and concentrated under reduced pressure. The solid residue was suspended in water, filtered off, and washed with water and ether to give the title compound (140 mg, 99%) as a white solid, m.p. >300° C.

Analysis %:—Found: C, 37.69; H, 3.09; N, 11.84. $C_{11}H_{11}Cl_2N_3O_4S$ requires: C, 37.51; H, 3.15; N, 11.93%.

EXAMPLES 8–48

The following examples, shown in Table 2, were prepared by the method of Example 7, using the corresponding 2,3-dimethoxyquinoxaline derivative (Preparations 3, 4, 6, 7, 11, 12, 13 and 14) and the appropriate alkyl halide [i.e. methyl iodide, ethyl iodide, n-butyl bromide, 3-(N,N-dimethylamino)propyl chloride, benzyl chloride, phenethyl bromide, 2-propyl bromide, 2-methoxyethyl bromide, allyl bromide, cyclopentyl bromide, 2-(morpholino)ethyl chloride, 4-picolyl chloride, 2-hydroxyethyl bromide, n-propyl bromide, 2-picolyl chloride, 3-hydroxypropyl bromide, chloroacetone, propargyl bromide and 2-(bromomethyl)-6-methoxypyridine (the compound of Preparation 22)].

TABLE 2

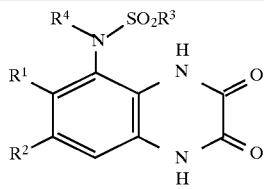

| Ex. No. | $R^1,R^2$ | $R^3$ | $R^4$ | m.p. (°C.) | Formula | Analysis % Found (Required) C | H | N |
|---|---|---|---|---|---|---|---|---|
| 8 | —Cl | —$CH_3$ | —$CH_3$ | >330 | $C_{10}H_9Cl_2N_3O_4S.0.5H_2O$ | 35.07 (34.90) | 2.62 (2.83) | 11.95 (12.21) |
| 9 | —Cl | —$CH_3$ | —$CH_2CH_3$ | 294–297 | $C_{11}H_{11}Cl_2N_3O_4S$ | 37.13 (37.51) | 2.98 (3.14) | 11.40 (11.93) |
| 10 | —Cl | —$CH_3$ | —$CH_2CH_2CH_2CH_3$ | 260–261 | $C_{13}H_{15}Cl_2N_3O_4S$ | 41.42 (41.06) | 4.09 (3.98) | 10.77 (11.05) |
| 11$^{(a)}$ | —Cl | —$CH_3$ | —$CH_2Ph$ | 282–283 | $C_{16}H_{13}Cl_2N_3O_4S$ | | | |
| 12 | —Cl | —$CH_3$ | —$CH_2CH_2Ph$ | 265–266 | $C_{17}H_{15}Cl_2N_3O_4S.0.4$-dioxane | 47.91 (48.16) | 3.91 (3.93) | 8.86 (9.11) |
| 13 | —Cl | —$CH_3$ | —$CH(CH_3)_2$ | >300 | $C_{12}H_{13}Cl_2N_3O_4S$ | 39.38 (39.35) | 3.53 (3.58) | 11.30 (11.47) |
| 14 | —Cl | —$CH_3$ | —$CH_2CH=CH_2$ | 276–277 | $C_{12}H_{11}Cl_2N_3O_4S$ | 39.42 (39.57) | 2.97 (3.04) | 11.43 (11.54) |
| 15 | —Cl | —$CH_3$ | cyclopentyl | 295(dec) | $C_{14}H_{15}Cl_2N_3O_4S$ | 42.78 (42.86) | 3.84 (3.85) | 10.34 (10.71) |

TABLE 2-continued

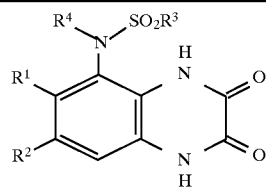

| Ex. No. | $R^1, R^2$ | $R^3$ | $R^4$ | m.p. (°C.) | Formula | C | H | N |
|---|---|---|---|---|---|---|---|---|
| 16 | —Cl | —CH$_3$ | —CH$_2$CH$_2$OCH$_3$ | 273–274 | C$_{12}$H$_{13}$Cl$_2$N$_3$O$_5$S | 37.96 (37.71 | 3.11 3.43 | 10.85 10.99) |
| 17† | —Cl | —CH$_3$ | —CH$_2$CH$_2$OH | 289–291 | C$_{11}$H$_{11}$Cl$_2$N$_3$O$_5$S | 35.82 (35.88 | 3.04 3.01 | 11.37 11.41) |
| 18 | —Cl | —CH$_3$ | —CH$_2$CH$_2$CH$_2$N(CH$_3$)$_2$ | 225(dec) | C$_{14}$H$_{18}$Cl$_2$N$_4$O$_4$S.HCl | 37.74 (37.72 | 4.49 4.30 | 12.32 12.57) |
| 19 | —Cl | —CH$_3$ | —CH$_2$CH$_2$N(morpholino) | 271–272 (dec) | C$_{15}$H$_{18}$Cl$_2$N$_4$O$_5$S.HCl | 37.73 (38.02 | 4.46 4.04 | 11.69 11.83) |
| 20 | —Cl | —CH$_3$ | —H$_2$C-(4-pyridyl) | 278–279 | C$_{15}$H$_{12}$Cl$_2$N$_4$O$_4$S.HCl.H$_2$O | 38.47 (38.35 | 3.38 3.21 | 12.33 11.93) |
| 21 | —Cl | —CH$_3$ | —H$_2$C-(2-pyridyl) | 285–286 (dec) | C$_{15}$H$_{12}$Cl$_2$N$_4$O$_4$S.HCl | 39.96 (39.88 | 2.96 2.90 | 12.21 12.40) |
| 22 | —Cl | —CH$_2$CH$_3$ | —CH$_2$CH$_3$ | 197–199 | C$_{12}$H$_{13}$Cl$_2$N$_3$O$_4$S.0.5-dioxane | 41.38 (40.98 | 4.27 4.17 | 9.91 10.24) |
| 23 | —Cl | —CH$_2$CH$_3$ | —CH$_2$CH=CH$_2$ | >300 | C$_{13}$H$_{13}$Cl$_2$N$_3$O$_4$S | 41.51 (41.28 | 3.52 3.46 | 11.09 11.11) |
| 24 | —Cl | —CH$_2$CH$_3$ | —CH$_2$CH$_2$OH | >300 | C$_{12}$H$_{13}$Cl$_2$N$_3$O$_5$S.H$_2$O | 36.20 (36.01 | 3.48 3.78 | 10.63 10.50) |
| 25 | —CH$_3$ | —CH$_3$ | —CH$_2$CH$_3$ | 287–289 | C$_{13}$H$_{17}$N$_3$O$_4$S.0.15H$_2$O | 49.74 (49.72 | 5.42 5.55 | 13.15 13.38) |
| 26 | —CH$_3$ | —CH$_3$ | —CH$_2$CH$_2$CH$_2$CH$_3$ | 308–311 | C$_{15}$H$_{21}$N$_3$O$_4$S | 53.14 (53.08 | 6.37 6.24 | 12.35 12.38) |
| 27 | —CH$_3$ | —CH$_3$ | —CH$_2$CH=CH$_2$ | 267–268 | C$_{14}$H$_{17}$N$_3$O$_4$S.0.1H$_2$O | 51.75 (51.71 | 5.44 5.33 | 12.91 12.92) |
| 28 | —CH$_3$ | —CH$_3$ | —CH$_2$CH$_2$OH | 313–314 | C$_{13}$H$_{17}$N$_3$O$_5$S.0.3H$_2$O | 46.88 (46.92 | 5.46 5.33 | 12.60 12.63) |
| 29 | —Cl | —CH$_3$ | —CH$_2$CH$_2$CH$_2$OH | 248–249 | C$_{12}$H$_{13}$Cl$_2$N$_3$O$_5$S | 37.57 (37.71 | 3.57 3.43 | 10.79 10.99) |
| 30 | —Cl | —CH$_3$ | —CH$_2$CH$_2$CH$_3$ | 286–287 | C$_{12}$H$_{13}$Cl$_2$N$_3$O$_4$S | 39.19 (39.35 | 3.60 3.58 | 11.17 11.47) |
| 31 | —Cl | —CH$_3$ | —CH$_2$C≡CH | 261–263 (dec) | C$_{12}$H$_9$Cl$_2$N$_3$O$_4$S | 39.73 (39.79 | 2.40 2.50 | 11.50 11.60) |
| 32 | —Cl | —CH$_3$ | —CH$_2$COCH$_3$ | >300 | C$_{12}$H$_{11}$Cl$_2$N$_3$O$_5$S | 37.92 (37.90 | 2.83 2.92 | 10.86 11.05) |
| 33 | —CH$_3$ | —CH$_2$CH$_3$ | —CH$_2$CH$_3$ | 245–246 | C$_{14}$H$_{19}$N$_3$O$_4$S | 51.94 (51.68 | 5.82 5.89 | 12.99 12.91) |
| 34 | —CH$_3$ | —CH$_2$CH$_3$ | —CH$_2$CH=CH$_2$ | 206–208 | C$_{15}$H$_{19}$N$_3$O$_4$S | 53.72 (53.40 | 5.74 5.68 | 12.47 12.45) |
| 35 | —Br | —CH$_3$ | —CH$_2$CH$_3$ | 302–304 | C$_{11}$H$_{11}$Br$_2$N$_3$O$_4$S | 30.04 (29.95 | 2.49 2.51 | 9.40 9.53) |
| 36 | —Br | —CH$_3$ | —CH$_2$CH$_2$OH | 291–293 | C$_{11}$H$_{11}$Br$_2$N$_3$O$_5$S | 28.72 (28.90 | 2.52 2.43 | 8.94 9 19) |
| 37(b) | Cl | CH$_3$ | (6-methyl-2-oxo-1,2-dihydropyridin-3-yl)methyl | 300(dec) | C$_{15}$H$_{12}$Cl$_2$N$_4$O$_5$S0.75H$_2$O | 40.56 (40.51 | 3.13 3.06 | 12.34 12.60) |
| 38 | 6-Cl,7 —CH$_2$CH$_3$ | CH$_3$ | CH$_2$CH$_2$OH | 276–279 | C$_{13}$H$_{16}$ClN$_3$O$_5$S.0.1CH$_2$Cl$_2$ | 42.63 (42.62 | 4.04 4.42 | 11.15 11.38) |

TABLE 2-continued

[Structure diagram showing substituted quinoxalinedione with R1, R2, R3, R4 groups]

| Ex. No. | R¹,R² | R³ | R⁴ | m.p. (°C.) | Formula | Analysis % Found (Required) C | H | N |
|---|---|---|---|---|---|---|---|---|
| 39(c) | 6-Cl,7—CH$_2$CH$_3$ | CH$_3$ | CH$_2$CH$_3$ | 265–269 | C$_{13}$H$_{16}$ClN$_3$O$_4$S | | | |
| 40 | 7-Cl,6—CH$_2$CH$_3$ | CH$_3$ | CH$_2$CH$_2$OH | 298–300 | C$_{13}$H$_{16}$ClN$_3$O$_5$S | 42.88 (43.16 | 4.15 4.46 | 11.21 11.61) |
| 41(d) | CH$_3$ | CH$_3$ | CH$_2$CH$_2$CH$_3$ | 287–291 | C$_{14}$H$_{19}$N$_3$O$_4$S | | | |
| 42(e) | CH$_3$ | CH$_3$ | CH$_3$ | >300 | C$_{12}$H$_{15}$N$_3$O$_4$S | | | |
| 43(f) | 6-Cl,7—CH$_3$ | CH$_3$ | CH$_2$CH$_3$ | 300–304 | C$_{11}$H$_{14}$ClN$_3$O$_4$S | | | |
| 44(g) | 6-Cl,7—CH$_3$ | CH$_3$ | CH$_2$CH$_2$OH | >300 | C$_{12}$H$_{14}$ClN$_3$O$_5$S | | | |
| 45(h) | 7-Cl,6—CH$_3$ | CH$_3$ | CH$_2$CH$_3$ | 289–290 | C$_{12}$H$_{14}$ClN$_3$O$_4$S | 43.16 (43.44 | 4.11 4.25 | 11.74 12.67) |
| 46(i) | 7-Cl,6—CH$_3$ | CH$_3$ | CH$_2$CH$_2$OH | 311 (dec) | C$_{12}$H$_{14}$ClN$_3$O$_5$S | 41.53 (41.44 | 4.17 4.06 | 11.14 12.08) |
| 47(j) | CH$_3$ | CF$_3$ | CH$_2$CH$_3$ | 235–237 | C$_{13}$H$_{14}$F$_3$O$_4$S | | | |
| 48(k) | CH$_3$ | CF$_3$ | CH$_2$CH$_2$OH | 239–241 | C$_{13}$H$_{14}$F$_3$N$_3$O$_5$S | | | |

Notes to Table 2
(a)¹H NMR (300 MHz, DMSO-d$_6$): 3.39(3H, s), 4.74(1H, d, J 14Hz), 4.82(1H, d, J 14Hz), 7.20(4H, m), 7.30(2H, m), 10.24(1H, br s), 12.13(1H, br s).
(b)Prepared by the method of Example 7(b) using N-(6,7-dichloro-2,3-dimethoxyquinoxalin-5-yl)-N-[(6-methoxypyridin-2-yl)methyl]-methane-sulphonamide (Preparation 22). During the hydrolysis of the dimethoxyquinoxaline, the methoxypyridine is converted to the 2-pyridone.
(c)¹H NMR (300 MHz, DMSO-d$_6$) δ = 0.95(3H, t, J 8Hz), 1.18(3H, t, J 8Hz), 2.70 2H, q, J 8Hz), 3.20(3H, s), 3.71(2H, m), 7.05(1H, s), 10.75(1H, brs), 12.09(1H, br s). m/z (thermospray) 357 (MNH$_4$⁺), v$_{max}$ (KBr) 3300, 2950, 1720, 1330 and 1150 cm⁻¹.
(d)¹H NMR (300 MHz, DMSO-d$_6$) δ = 0.80(3H, t, J 8Hz), 1.30(2H, m), 2.19(3H, s), 2.22(3H, s), 3.19(3H, obscured), 3.49(2H, m), 6.98(1H, s), 9.95(1H, brs), 11.83(1H, br s). m/z (thermospray) 326 (MH⁺), 343 (MNH$_4$⁺), v$_{max}$ (KBr) 3380, 3220, 1720, 1680 and 1150 cm⁻¹.
(e)¹H NMR (300 MHz, DMSO-d$_6$) δ = 2.19(3H, s), 2.21(3H, s), 3.16(3H, s), 6.95(1H, s), 10.67(1H, br s), 11.82(1H, br s). m/z (thermospray 298 (MH⁺), 315 (MNH$_4$⁺), v$_{max}$ (KBr) 3225, 1700, 1325, 1140 and 750 cm⁻¹.
(f)¹H NMR (300 MHz, DMSO-d$_6$) δ = 1.00(3H, t, J 8Hz), 2.35(3H, s), 3.58(3H, s), 3.72(2H, m), 7.12(1H, s), 10.40(1H, br s), 12.01(1H, br s). m/z (thermospray) 349 (MNH$_4$⁺), v$_{max}$ (KBr) 3450, 3260, 2950, 1700, 1380, 1330, 1150 and 520 cm⁻¹.
(g)¹H NMR (300 MHz, DMSO-d$_6$) δ = 2.31(3H, s), 3.20(3H, s), 3.34(2H, m), 4.02(2H, m), 7.10(1H, s), 10.80(1H, br s), 12.10(1H, br s). m/z (thermospray) 365 (MNH$_4$⁺).
(h)¹H NMR (300 MHz, DMSO-d$_6$) δ = 1.00(3H, t, J 7Hz), 2.30(3H, s), 3.23(3H, s), 3.65(2H, q, J 7Hz), 7.24(1H, s), 10.40(1H, br s), 11.93(1H, br s). m/z (thermospray) 349 (MNH$_4$⁺).
(i)¹H NMR (300 MHz, DMSO-d$_6$) δ = 2.30(3H, s), 3.19(3H obscured), 3.34(2H, m), 3.74(2H, m), 4.05(1H, m), 5.98(1H, m), 7.23(1H, s), 10.92(1H, br s), 11.91(1H, brs). m/z( thermospray) 348 (MH⁺), 365 (MNH$_4$⁺).
(j)¹H NMR (300 MHz, DMSO-d$_6$) δ = 1.05(3H, t, J 8Hz), 2.18(3H, s), 2.22(3H, s), 3.90(2H, m), 7.10(1H, s), 10.82(1H, br s), 11.94(1H, br s). m/z (thermospray) 383 (MNH$_4$⁺).
(k)¹H NMR (300 MHz, DMSO-d$_6$) δ = 2.18(3H, s), 2.22(3H, s), 3.35(1H, m), 3.50(1H, m), 3.70(1H, m), 4.16(1H, m), 6.10(1H, br s), 7.05(1H, s), 10.85(1H, br s), 11.95(1H, br s). m/z (thermospray) 382 (MH⁺), 399 (MNH$_4$⁺).
†Alternatively, the compound of Example 17 may be prepared as follows:

(RS)-N-(f1,4-Dihydro-6,7-dichloro-2,3-dioxoquinoxaline-5-yl)-N-(2-hydroxyethyl) methanesulphonamide

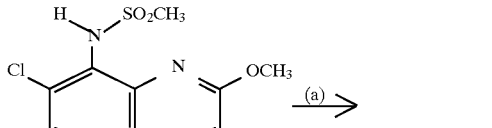

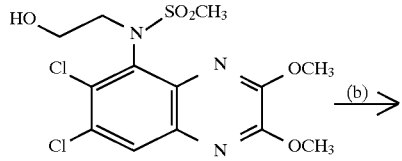

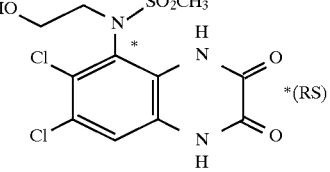

a) A mixture of potassium carbonate (25.81 g, 0.187 mol), 2-bromoethanol (13.26 ml, 0.187 mol) and N-(6,7-dichloro-2,3-dimethoxyquinoxalin-5-yl)-methanesulphonamide (Preparation 3) (55.0 g, 0.156 mol) in acetone (2.5 L), was heated at reflux for 20 h, cooled and the acetone removed under reduced pressure. The residue was partitioned between dichloromethane and 1M sodium hydroxide. The organic layer was then dried (MgSO$_4$), concentrated under reduced pressure and the residue purified by recrystallisation three times from methanol to give (RS)-N-(6,7-dichloro-2, 3-dimethoxyquinoxalin-5-yl)-N-(2-hydroxyethyl)methanesulphonamide (43.7g, 70%) as a white solid, m.p. 240°–242° C.

Analysis %: Found: C,39.35; H,3.78; N,10.55. $C_{13}H_{15}N_3O_5Cl_2$ requires: C,39.41; H,3.82; N,10.61%.

b) A mixture of (RS)-N-(6,7-dichloro-2,3-dimethoxyquinoxalin-5-yl)-N-(2-hydroxyethyl)methanesulphonamide (11.41 g, 0.029 mol) and 2M hydrochloric (300 ml) acid was heated at reflux for 18½ h then cooled in an ice-bath. The solid was filtered off, and washed with water to give the title compound (9.65 g, 91%) as a white solid, m.p. 272–274° C.

Analysis %: Found: C,35.82; H,3.04; N,11.37. $C_{11}H_{11}N_3O_5Cl_2S$ requires: C,35.88; H,3.01; N,11.41%.

EXAMPLE 49

N-(1.4-Dihydro-6.7-dichloro-2.3-dioxoquinoxaline-5-yl)-N-(3-pyridylmethyl)methanesulphonamide hydrochloride

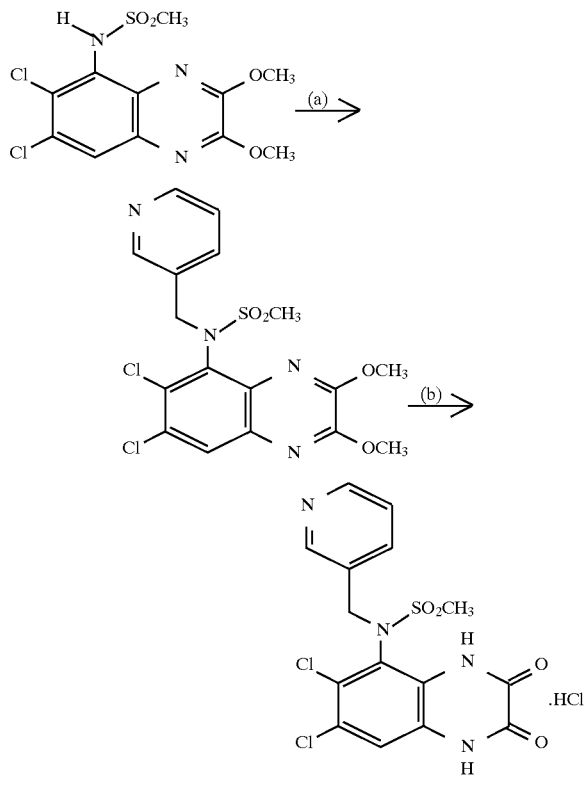

(a) Diethyl azodicarboxylate (90 μl, 0.57 mmol) was added to a stirred solution of N-(6,7-dichloro-2,3-dimethoxyquinoxalin-5-yl)methanesulphonamide (200 mg, 0.57 mmol - see Preparation 3), 3-(hydroxymethyl)pyridine (55 gl, 5 0.57 mmol), and triphenylphosphine (149 mg, 0.57 mmol) in dry tetrahydrofuran (12 ml) under nitrogen at 23° C. After 8 hours, the solvent was removed under reduced pressure and the residue was purified by flash chromatography (gradient elution with ether/methanol) to give N-(6, 7-dichloro-2,3-dimethoxyquinoxalin-5-yl)-N-(3-pyridylmethyl)methanesulphonamide (145 mg, 57%) as a white solid, m.p. 217° C. (dec.).

$^1$H NMR (300 MHz, $CDCl_3$): δ=3.18 (3H, s), 4.10 (3H, s), 4.14 (3H, s), 4.95 (2H, s), 7.17 (1H, dd, J 4 and 6 Hz), 7.68 (1H, dt, J 2 and 6 Hz), 7.90 (1H, s), 8.41 (1 H, d, J 2 Hz), 8.48 (1 H, dd, J 2 and 4 Hz). m/z (thermospray) (443 MH$^+$).

(b) A mixture of N-(6,7-dichloro-2,3-dimethoxyquinoxalin-5-yl)-N-(3-pyridylmethyl)-methanesulphonamide (130 mg, 0.293 mmol), 2M hydrochloric acid (2 ml) and dioxane (4 ml) was heated at reflux for 2.5 hours, cooled, and concentrated under reduced pressure. The residue was suspended in water (1 ml), filtered off, and washed with water and ether to give the title compound (120 mg, 98%) as a white solid, m.p. 234°–235° C. (dec.).

Analysis %: Found:C, 39.67; H, 3.06; N, 12.20;S, 7.05. $C_{15}H_{12}Cl_2N_4O_4S.HCl$ requires: C, 39.88; H, 2.90; N, 12.40; S, 7.10%.

EXAMPLES 50–65

The following Examples, shown in Table 3, were prepared by the method of Example 49, using the corresponding 2,3-dimethoxyquinoxaline derivative (Preparations 3 and 4) and the appropriate alcohol (commercially available and/or as prepared in Preparations 15–19. The trityl protecting group in Preparations 15–19 is removed simultaneously in the final acid hydrolysis step).

TABLE 3

Structure: benzene ring with R¹, R² substituents, and R⁴N(SO₂R³)- group, with a fused piperazine-2,3-dione (two NH linked to oxalyl)

| Ex. No. | R¹, R² | R³ | R⁴ | m.p.(°C.) | Formula | C (Found / Required) | H | N |
|---|---|---|---|---|---|---|---|---|
| 50 | —Cl | —CH₃ | (1H-imidazol-4-yl)CH₂— | 245(dec) | $C_{13}H_{11}Cl_2N_5O_4S \cdot HCl$ | 35.71 (35.43) | 3.10 (2.75) | 16.00 (15.89) |
| 51 | —Cl | —CH₃ | (1-methylimidazol-2-yl)CH₂— | 238–239 | $C_{14}H_{13}Cl_2N_5O_4S \cdot HCl \cdot H_2O$ | 35.85 (35.57) | 3.40 (3.41) | 14.73 (14.81) |
| 52 | —Cl | —CH₃ | —(CH₂)₂O(CH₂)₂—N(CH₂CH₃)₂ | 269–270 | $C_{17}H_{24}Cl_2N_5O_5S \cdot HCl$ | 40.20 (40.52) | 4.95 (5.00) | 10.86 (11.12) |
| 53[a] | —Cl | —CH₃ | (4-methyl-1H-imidazol-2-yl)CH₂— | 235–236 | $C_{14}H_{13}Cl_2N_5O_4S \cdot HCl$ | | | |
| 54 | —Cl | —CH₃ | (1H-imidazol-2-yl)CH₂— | 210(dec) | $C_{13}H_{11}Cl_2N_5O_4S \cdot HCl$ | 35.31 (35.43) | 2.81 (2.75) | 15.70 (15.89) |
| 55 | —Cl | —CH₂CH₃ | (1-methylimidazol-2-yl)CH₂— | >300 | $C_{15}H_{15}Cl_2N_5O_4S \cdot HCl$ | 38.99 (38.44) | 3.35 (3.44) | 14.92 (14.94) |
| 56 | —Cl | —CH₃ | (1-methylbenzimidazol-2-yl)CH₂— | 261–262 | $C_{18}H_{15}Cl_2N_5O_4S \cdot HCl$ | 42.93 (42.83) | 2.93 (3.20) | 14.15 (13.88) |
| 57 | —Cl | —CH₃ | (furan-2-yl)CH₂— | 235–236 | $C_{14}H_{11}Cl_2N_3O_5S$ | 41.29 (41.60) | 2.68 (2.74) | 10.48 (10.40) |
| 58[b],[c] | Cl | CH₃ | (1H-pyrazol-4-yl)CH₂— | >300 | $C_{13}H_{11}Cl_2N_5O_4S$ | | | |
| 59[b] | Cl | CH₃ | (1H-pyrazol-3-yl)CH₂— (with additional N) | >300 | $C_{12}H_{10}Cl_2N_6O_4S \cdot 0.5H_2O$ | 34.42 (34.80) | 2.40 (2.68) | 20.45 (20.29) |

TABLE 3-continued

| Ex. No. | R¹, R² | R³ | R⁴ | m.p.(°C.) | Formula | Analysis % Found (Required) C | H | N |
|---|---|---|---|---|---|---|---|---|
| 60[b] | Cl | $CH_3$ | (triazolyl-CH₂, H on N) | >300 | $C_{12}H_{10}Cl_2N_6O_4S \cdot 0.5H_2O \cdot$ 0.375 dioxane | 36.19 (36.25 | 2.86 3.16 | 18.90 18.79) |
| 61[b] | Cl | $CH_3$ | (pyrazolyl-CH₂, H on N) | >300 | $C_{13}H_{11}Cl_2N_5O_4S \cdot 0.5H_2O \cdot$ 0.33$CH_3OH$ | 37.97 (37.78 | 2.80 3.17 | 16.13 16.52) |
| 62[b] | Cl | $CH_3$ | (imidazolyl-CH₂-CH₃, H on N) | 240–243 | $C_{14}H_{13}Cl_2N_5O_4S \cdot HCl \cdot$ 0.8$H_2O$ | 36.04 (35.84 | 3.31 3.35 | 14.43 14.92) |
| 63 | Cl | $CH_3$ | (isoxazolyl-CH₂, CH₃) | 285–290 (dec) | $C_{14}H_{12}Cl_2N_4O_5S \cdot 0.5H_2O$ | 39.38 (39.27 | 2.84 3.06 | 12.83 13.08) |
| 64 | Cl | $CH_3$ | (3-hydroxypyridin-2-yl-CH₂) | 285–290 (dec) | $C_{15}H_{12}Cl_2N_4O_5S \cdot HCl$ | 38.81 (38.52 | 2.59 2.80 | 11.98 11.98) |
| 65 | Cl | $CH_3$ | (pyrazin-2-yl-CH₂) | >300 | $C_{14}H_{11}Cl_2N_5O_4S \cdot 0.25 H_2O \cdot 0.4$ dioxane | 41.47 (41.09 | 2.92 3.25 | 15.04 15.36) |

Notes to Table 3:
[a] ¹H NMR (300 MHz, DMSO-d₆, broadened signals due to tautomer interconversion) 2.10(3H, s), 3.22(3H, br s), 4.80(2H, br s), 7.38(1H, s), 8.65(1H, br s), 12.23(1H, br s), 14.0(1H, br s).
[b] As mentioned above for the Mitsunobu reaction, the heterocycles were trityl protected, as described in Preparations 15–19. The trityl protecting group was removed concurrently with hydrolysis of the dimethoxquinoxaline, and the trityl containing side product removed by trituration with acetone.
[c] ¹H NMR(300 MHz, DMSO-d₆) δ = 3.22(3H, s), 4.73(1H, d, J15Hz), 4.89 (1H, d, J15Hz), 7.23(1H, s), 7.47(2H, s), 10.68(1H, br s), 12.10(1H, br s).

EXAMPLE 66

(RS), (RS)-N-(1,4-Dihydro-6,7-dichloro-2,3-dioxoquinoxalin-5-yl)-N-(2-hydroxypropyl)methanesulphonamide

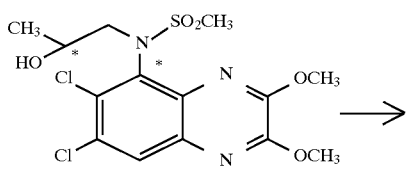

→

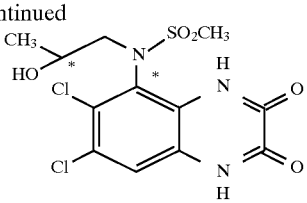

The title compound was prepared from (RS)-N-(6,7-dichloro-2,3-dimethoxyquinoxalin-5-yl)-N-(2-hydroxypropyl)methanesulphonamide (Preparation 9) by the method of Example 1; yield 81% of a white solid (a mixture 10 of diastereoisomers), m.p. 291°–292° C. (from water).

Analysis %: Found: C, 37.77; H, 3.15; N, 10.63. $C_{12}H_{13}Cl_2N_3O_5S$ requires: C, 37.71; H, 3.43; N, 10.99%.

EXAMPLE 67

N-(1,4-Dihydro-6,7-dichloro-2,3-dioxoquinoxaline-5-yl)-N-(2-hydroxy-2-methylpropyl)methanesulphonamide

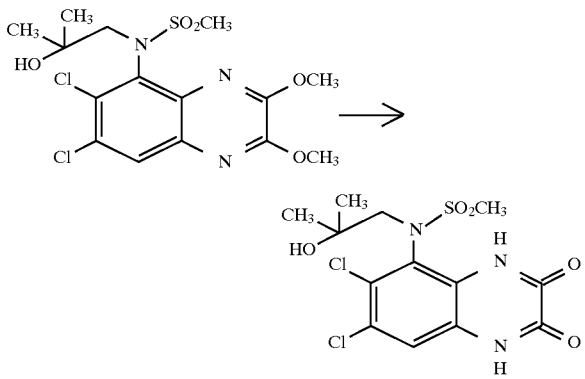

The title compound was prepared from N-(6,7-dichloro-2,3-dimethoxyquinoxalin-5-yl)-N-(2-hydroxy-2-methylpropyl)methanesulphonamide (Preparation 10) by the method of Example 1; yield 83% of a white solid, m.p. 252°–253° C. (dec.)

Analysis %:—Found: C, 39.32; H, 3.71; N, 10.55. $C_{13}H_{15}Cl_2N_3O_5S$ requires: C, 39.40; H, 3.81; N, 10.60%.

EXAMPLE 68

N-(1,4-Dihydro-6-chloro-7-trifluoromethyl-2,3-dioxoquinoxaline-5-yl)-N-ethylmethanesulphonamide

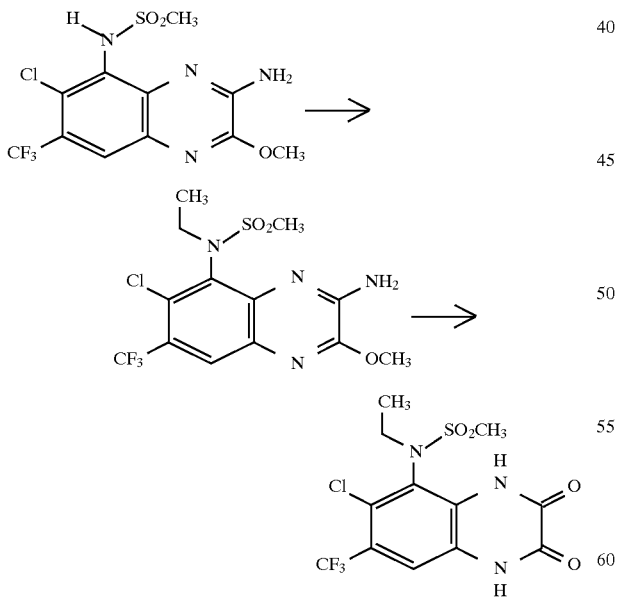

(a) A mixture of N-(3-amino-6-chloro-7-trifluoromethyl-2-methoxyquinoxalin-5-yl)methanesulphonamide (Preparation 20, 73 mg, 0.2 mmol) and anhydrous potassium carbonate (33 mg, 0.24 mmol) in acetone was stirred under reflux for 20 mins. Iodoethane (32 μl, 0.4 mmol) was added, and the mixture was heated for a further 2 h. Additional iodoethane (32 μl, 0.4 mmol) was added, and heating was continued for a further 4 h. The mixture was concentrated under reduced pressure and the residue was partitioned between water and ethyl acetate. The organic solution was dried (MgSO$_4$), concentrated under reduced pressure, and the residue was purified by flash chromatography (gradient elution with dichloromethane/methanol) to give N-(3-amino-6-chloro-7-trifluoromethyl-2-methoxyquinoxalin-5-yl)-N-ethyl-methanesulphonamide (75 mg, 96%), as a white solid.

$^1$H NMR (300MHz, CDCl$_3$) δ=1.16 (3H,t,J7 Hz), 3.20 (3H,s), 3.86 (2H,m), 4.16 (3H,s), 5.50 (2H,br s), 8.06 (1 H,s). m/z (thermospray) 399 (MH$^+$).

(b) A mixture of N-(3-amino-6-chloro-7-trifluoromethyl-2-methoxyquinoxalin-5-yl)-N-ethyl-methanesulphonamide (step (a) above, 70 mg, 0.18 mmol), 2M hydrochloric acid (3 ml) and dioxane (6 ml) was heated at reflux for 2 h, cooled and concentrated under reduced pressure. The residue was suspended in water, filtered and the solid was washed with water. After being dried, the title compound (33 mg, 48%) was obtained as a white solid, m.p. >300° C.

Analysis:—Found: C,37.61; H,2.73; N,10.80. $C_{12}H_{11}ClF_3N_3O_4S$ requires: C,37.36; H, 2.87; N,10.89%.

EXAMPLE 69

N-(1,4-Dihydro-6-chloro-7-trifluoromethyl-2,3-dioxoquinoxaline-5-yl)-N-(2-hydroxyethyl)methanesulphonamide

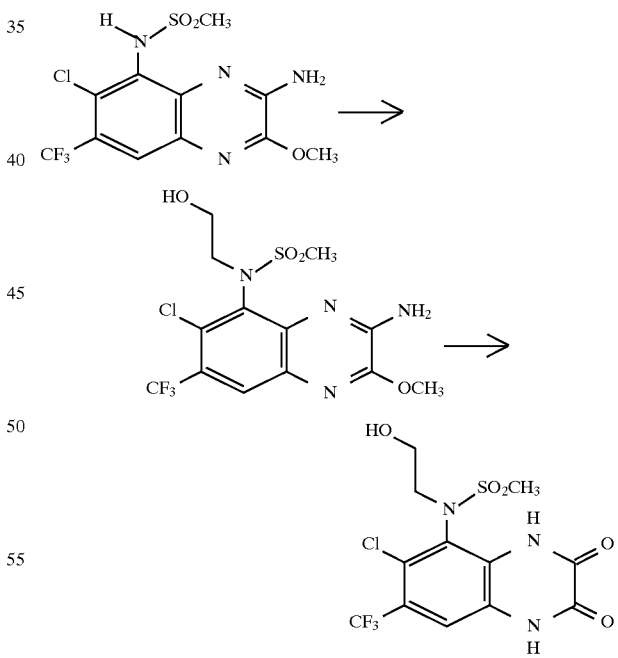

By the method of Example 68 above, the title compound was prepared, substituting 2-bromoethanol for iodoethane. It was obtained as a white solid (40 mg, 44% yield for the two steps), m.p. 292°–294° C.

Analysis %:—Found: C,36.17; H,2.73; N,10.26. $C_{12}H_{11}ClF_3N_3O_5S$ requires: C,35.88; H,2.76; N,10.46%.

EXAMPLE 70

(RS)-N-(Carboxymethyl)-N-(1,4-dihydro-6,7-dichloro-2,3-dioxoquinoxaline-5-yl)methanesulphonamide

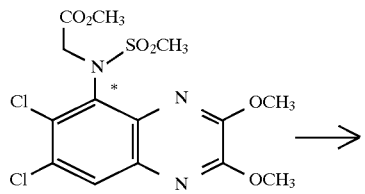

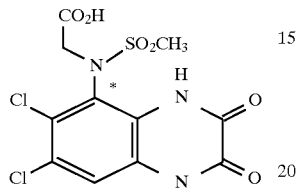

A mixture of N-(6,7-dichloro-2,3-dimethoxyquinoxalin-5-yl)-N-(methoxycarbonylmethyl) methanesulphonamide (Preparation 21, 3.17 g, 7.48 mmol), 2M hydrochloric acid (80 ml) and dioxane (80 ml) was heated at reflux for 18 h, cooled and concentrated under reduced pressure to give a yellow solid (2.85 g, 100%), m.p. 271° C. (dec).

Analysis %:—Found: C,33.98; H,2.64; N,10.50. $C_{11}H_9Cl_2N_3O_6S \cdot \tfrac{1}{2}H_2O$ requires: C,33.77; H,2.58; N,10.74%.

EXAMPLE 71

(RS)-N-(1,4-Dihydro-6,7-dichloro-2,3-dioxoquinoxalin-5-yl)-N-(methoxycarbonylmethyl)methanesulphonamide

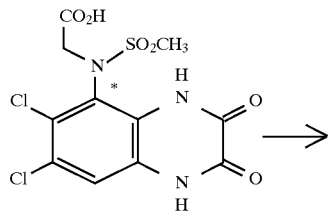

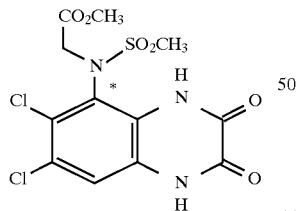

A solution of N-(carboxymethyl)-N-(1,4-dihydro-6,7-dichloro-2,3-dioxoquinoxalin-5-yl)methanesulphonamide (Example 70, 2.85 g, 7.46 mmol) in dry methanol (100 ml) saturated with hydrogen chloride gas was heated under reflux for 3 h, cooled and concentrated under reduced pressure to give a yellow solid (2.838 g, 96%) m.p. 301° C. (dec).

Analysis %:—Found: C,36.29; H,2.60; N,10.49. $C_{12}H_{11}Cl_2N_3O_6S$ requires: C,36.38; H,2.80; N,10.61%.

EXAMPLE 72

N-(1,4-Dihydro-6,7-dichloro-2,3-dioxoguinoxalin-5-yl)-N-(N'-methylcarbamoylmethyl)methanesulphonamide

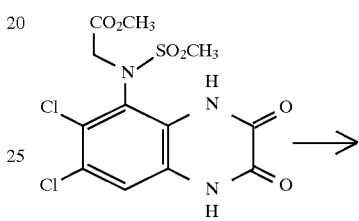

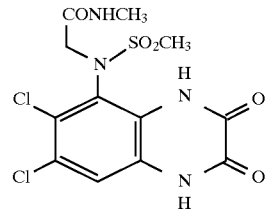

A mixture of N-(1,4-dihydro-6,7-dichloro-2,3-dioxoquinoxalin-5-yl)-N-(methoxycarbonylmethyl) methanesulphonamide (from Example 71, 150 mg, 0.38 mmol), ethanol (3 ml) and methylamine (33% solution in ethanol, 3 ml) was heated in a closed vessel at 75° C. for 1 h, then 90° C. for 1.5 h. The mixture was cooled and poured slowly into an excess of 2M hydrochloric acid. The white precipitate was filtered off and dried to afford the title compound (107 mg, 72%), m.p. 289° C.

Analysis %:—Found: C,36.24; H,2.99; N,13.98. $C_{12}H_{12}Cl_2N_4O_5S$ requires: C,36.47; H,3.06; N,14.18%.

The compounds shown in Table 4 below were prepared from the compound of Example 71 by the method of Example 72, using the appropriate amine instead of methylamine.

TABLE 4

[Structure shown with CONR⁵R⁶, SO₂CH₃, Cl substituents on dihydroquinoxaline-dione scaffold]

| Ex. No. | $R^5$ | $R^6$ | m.p.(°C.) | Formula | Analysis % Found (Required) C | H | N |
|---|---|---|---|---|---|---|---|
| 73 | H | H | 223(dec) | $C_{11}H_{10}Cl_2N_4O_5S \cdot 1.5H_2O$ | 32.28 (32.37 | 3.04 3.21 | 13.59 13.73) |
| 74 | $CH_3$ | $CH_3$ | >300 | $C_{13}H_{14}Cl_2N_4O_5S$ | 37.92 (38.15 | 3.26 3.45 | 13.62 13.69) |
| 75 | $CH_2CH_3$ | H | 297 | $C_{13}H_{14}Cl_2N_4O_5S$ | 38.20 (38.15 | 3.23 3.45 | 13.45 13.69) |
| 76 | $CH(CH_3)_2$ | H | 278(dec) | $C_{14}H_{16}Cl_2N_4O_5S \cdot 0.75H_2O$ | 38.58 (38.49 | 3.89 4.04 | 12.81 12.83) |
| 77 | $-CH_2CH_2CH_2CH_2-$ | | 300(dec) | $C_{15}H_{16}Cl_2N_4O_5S \cdot H_2O$ | 39.71 (39.75 | 3.93 4.00 | 12.21 12.36) |
| 78 | $-CH_2CH_2OCH_2CH_2-$ | | 300(dec) | $C_{15}H_{16}Cl_2N_4O_6S \cdot H_2O$ | 38.41 (38.39 | 3.69 3.87 | 11.73 11.94) |

EXAMPLE 79

(RS), (RS)-N-(1-Carboxyethyl)-N-(1,4-dihydro-6, 7-dichloro-2,3-dioxoquinoxalin-5-yl) methanesulphonamide

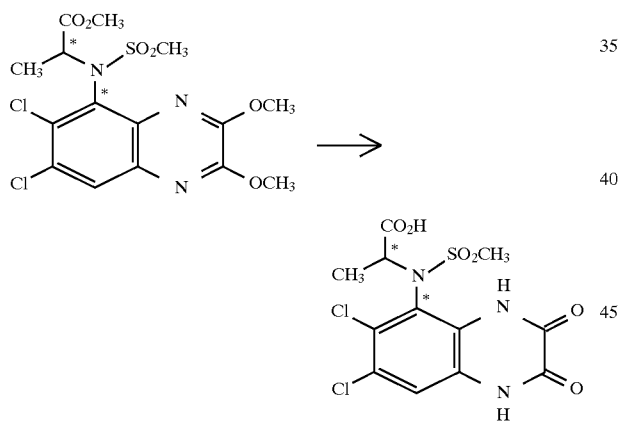

A 1:1 mixture of the two isomers of N-(6,7-dichloro-2, 3-dimethoxyquinoxalin-5-yl)-N-(1-methoxycarbonyl-1-ethyl)-methanesulphonamide (Preparation 23, 1.40 g, 32 mmol), 2M hydrochloric acid (40 ml) and dioxane (40 ml) was heated in an autoclave at 130° C. for 48 h and 150° C. for 24 h. The mixture was cooled, concentrated to low volume under reduced pressure and the solid filtered off and washed with ether. The product was dissolved in 1M aqueous sodium hydroxide (40 ml) and precipitated by the addition of 2M hydrochloric acid (to pH3). The white solid was filtered off and dried in vacuo, to give the title compound (1.13 g, 89%), as a mixture of diastereomers, m.p. 282° C. (dec).

Analysis %: Found: C,33.68; H,3.17; N,9.61. $C_{12}H_{11}Cl_2N_3O_6S \cdot 0.5H_2O$ requires: C,34.06; H,3.33; N,9.93%.

EXAMPLE 80

(R)- and (S)-N-(1,4-Dihydro-6,7-dichloro-2,3-dioxoquinoxaline-5-yl)-N-(2-hydroxyethyl) methanesulphonamide (a) (RS)-N-(Carboxymethyl)-N-(1,4-dihydro-6,7-dichloro-2,3-dioxoquinoxaline-5-yl)methanesulphonamide

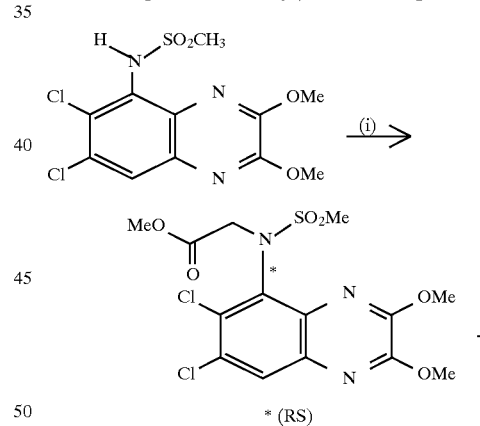

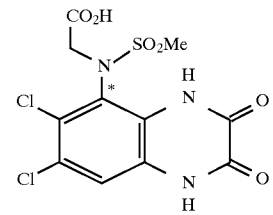

(i) A mixture of potassium carbonate (42.37 g, 0.3 mol), methylbromoacetate (48.4 ml, 0.51 mol) and N-(6,7-dichloro-2,3-dimethoxyquinoxalin-5-yl) methanesulphonamide (Preparation 3) (90 g, 0.256 mol) in acetone (1.75 L), was heated at reflux for 8½ h, cooled and the acetone removed under reduced pressure. The residue was stirred with water (1.5 L) for ¼h, filtered and the solid washed with water then ether to give (RS)-N-(6,7-dichloro-2,3-dimethoxyquinoxalin-5-yl)-N-(methoxycarbonylmethyl)-methanesulphonamide (108 g, 100%).

Analysis %: Found: C,39.51; H,3.52; N,9.89. $C_{14}H_{15}Cl_2N_3O_6S$ requires: C,39.63; H,3.56; N,9.90%.

(ii) A mixture of (RS)-N-(6,7-dichloro-2,3-dimethoxyquinoxalin-5-yl)-N-(methoxycarbonylmethyl) methanesulphonamide from (i) above, 2M hydrochloric acid (1 L) and dioxan (1 L) was heated at reflux for 18 h, cooled, and concentrated under reduced pressure. The solid residue was suspended in water (1.5 L), filtered off, and washed with water and ether to give the subtitle compound (95 g, 92%) as a white powder, m.p. 271 0° C. (dec).

Analysis %: Found: C,33.98; H,2.64; N,10.50. $C_{11}H_9Cl_2N_3O_6S \cdot \frac{1}{2}H_2O$ requires: C,33.77; H,2.58; N,10.74%.

(b) (R)-N-(Carboxymethyl)-N-(1,4-dihydro-6,7-dichloro-2,3-dioxoquinoxalin-5-yl)methanesulphonamide and (S)-N-(carboxymethyl)-N-(1,4-dihydro-6,7-dichloro-2,3-dioxoquinoxalin-5-yl-methanesulphonamide

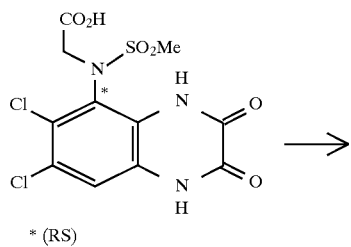

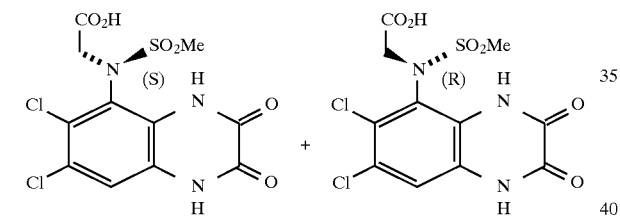

Quinine (25.48 g, 0.078 mol) in ethanol (300 ml) was added to a refluxing solution of (RS)-N-(carboxymethyl)-N-(1,4-dihydro-6,7-dichloro-2,3-dioxoquinoxalin-5-yl) methanesulphonamide (from step (a), 30 g, 0.078 mol) in ethanol (2.1 L). After ½ h at reflux the suspension was filtered hot and the solid washed with ethanol to give the subtitle compound of (S) stereochemistry as its quinine salt (23.2 g, 41.3%). $[\alpha]_D^{25}=-125.7$ (c=0.07, MeOH).

The filtrate was allowed to cool to room temperature with stirring, left a further 1 h then filtered to give the subtitle compound of (R) stereochemistry as its quinine salt (19.1 g, 34%).

$[\alpha]_D^{25}=-98.7°$ (c=0.15, MeOH).

The quinine salts were individually suspended in water (1.3 L) and treated with concentrated hydrochloric acid (22 ml) with vigorous stirring to give the two subtitle compounds after filtration.

The subtitle compound of (R) stereochemistry was obtained as a white solid (9.8 g, 95%) m.p. >218° C. (dec). $[\alpha]_D^{25}=+19.4°$ (c=0.18, MeOH).

Analysis %: Found: C,33.51; H,2.32; N,10.46. $C_{11}H_9Cl_2N_3O_6S \cdot \frac{1}{2}H_2O$ requires: C,33.77; H,2.58; N,10.74%.

The subtitle compound of (S) stereochemistry was obtained as a white solid (11.9 g, 95%).

(c) (R)-N-(1,4-Dihydro-6,7-dichloro-2,3-dioxoquinoxalin-5-yl)-N-(methoxycarbonylmethyl) methanesulphonamide

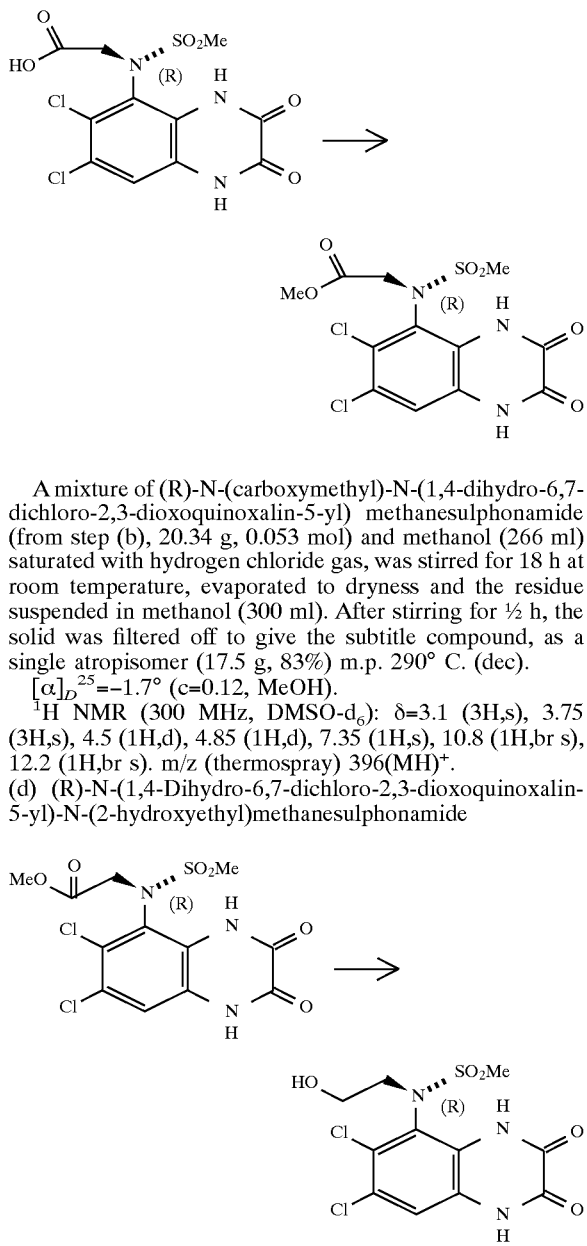

A mixture of (R)-N-(carboxymethyl)-N-(1,4-dihydro-6,7-dichloro-2,3-dioxoquinoxalin-5-yl) methanesulphonamide (from step (b), 20.34 g, 0.053 mol) and methanol (266 ml) saturated with hydrogen chloride gas, was stirred for 18 h at room temperature, evaporated to dryness and the residue suspended in methanol (300 ml). After stirring for ½ h, the solid was filtered off to give the subtitle compound, as a single atropisomer (17.5 g, 83%) m.p. 290° C. (dec).

$[\alpha]_D^{25}=-1.7°$ (c=0.12, MeOH).

$^1$H NMR (300 MHz, DMSO-$d_6$): δ=3.1 (3H,s), 3.75 (3H,s), 4.5 (1H,d), 4.85 (1H,d), 7.35 (1H,s), 10.8 (1H,br s), 12.2 (1H,br s). m/z (thermospray) 396(MH)$^+$.

(d) (R)-N-(1,4-Dihydro-6,7-dichloro-2,3-dioxoquinoxalin-5-yl)-N-(2-hydroxyethyl)methanesulphonamide Lithium aluminium hydride (39.4 ml, 1 molar in THF, 39.4 mmol) was added to (R)-N-(1,4-dihydro-6,7-dichloro-2,3-dioxoquinoxalin-5-yl)-N-(methoxycarbonylmethyl) methanesulphonamide (from step (c), 9.75 g, 24.6 mmol) in tetrahydrofuran (590 ml), cooled in an ice-bath to between 0°–5° C. After ¼ hour, further lithium aluminium hydride (2.4 ml, 2.46 mmol) was added, the mixture stirred a further ½ h and methanol (20 ml) in tetrahydrofuran (60 ml) added.

The mixture was evaporated to dryness under reduced pressure and the residue partitioned between ethyl acetate and 2M hydrochloric acid. The organic extracts were dried over sodium sulphate and concentrated under reduced pressure. The residue was purified by flash chromatography using gradient elution ($CH_2Cl_2$: MeOH containing 10% AcOH 100:0→95:5) to give the first title compound, as a single atropisomer, (6.0 g, 66%) m.p. 293°–294° C.

$[\alpha]_D^{25}$=+49.0 (c=0.1, 1M aqueous sodium hydroxide).

Analysis %: Found: C,35.89; H,2.83; N,11.42. $C_{11}H_{11}Cl_2N_3O_5S$ requires: C,35.88; H,3.01; N,11.41.

(e) (S)-N-(1,4-Dihydro-6,7-dichloro-2,3-dioxoquinoxaline-5-yl)-N-(methoxycarbonylmethyl)methanesulphonamide

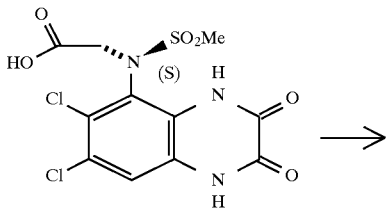

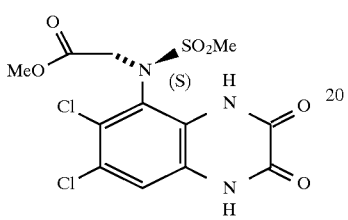

The subtitle compound was prepared from (S)-N-carboxymethyl-N-(1,4-dihydro-6,7-dichloro-2,3-dioxoquinoxalin-5-yl)methanesulphonamide (step (b)) by the method of step (c); yield 78% of a white solid.

$^1$H NMR (300 MHz, DMSO-$d_6$): δ=3.30 (3H,s), 3.75 (3H,s), 4.32 (1H,d), 4.85 (1H,d), 7.35 (1H,s), 10.85 (1H,s), 12.60 (1H,s). m/z (thermospray) 396 (MH$^+$).

(f) (S)-N-( 1.4-Dihydro-6.7-dichloro-2.3-dioxoquinoxalin-5-yl-N-(2-hydroyethyl)methanesulphonamide

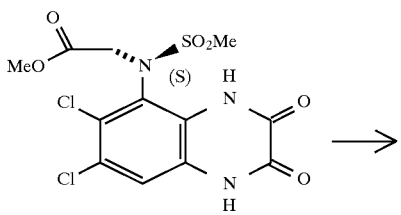

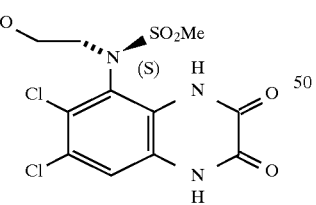

The second title compound was prepared from (S)-N-(1,4-Dihydro-6,7-dichloro-2,3-dioxoquinoxalin-5-yl)-N-(methoxycarbonylmethyl)-methanesulphonamide (step (e)) by the method of step (d); yield 60% of a white solid, m.p. >300°C.

$[\alpha]_D^{25}$=−45.0 (c=0.1, 1M aqueous sodium hydroxide).

$^1$H NMR (300 MHz, DMSO-$d_6$): δ=3.21 (5H,m), 3.65 (1H,m), 4.03 (1H,m), 6.02 (1H,br s), 7.32(1H,s), 11.00(1H, br s), 12.12(1H,br s). m/z (thermospray) 369(MH+).

EXAMPLE 81

(RS), (RS)-N-(1,4-Dihydro-6,7-dichloro-2,3-dioxoguinoxalin-5-yl)-N-(1-methoxycarbonylethyl)methanesulphonamide

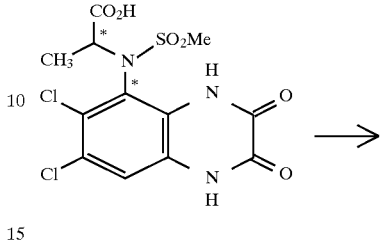

N-(1-carboxyethyl)-N-(1,4-dihydro-6,7-dichloro-2,3-dioxoquinoxalin-5-yl)methanesulphonamide (from Example 79, 1 g, 2.53 mmol) in methanol (100 ml) saturated with hydrogen chloride gas was stirred at room temperature for 24 h, then 8 h at 60° C. The solid was filtered off to give the title compound as a mixture of diastereomers (431 mg, 42%).

$^1$H NMR (300 MHz, DMSO-$d_6$): δ=1.70 (3H,d), 3.17 (3H,s), 3.77 (3H,s), 4.75 (1H,q), 7.39 (1H,s), 11.46 (1H,s), 12.20 (1H,s). m/z (thermospray) 413, 415 (MNH$_4^+$).

EXAMPLE 82

(RS), (RS)-N-(1 4-Dihydro-6,7-dichloro-2,3-dioxoquinoxaline-5-yl)-N-(1-(N'-methylcarbamoyl)ethyl)methanesulphonamide

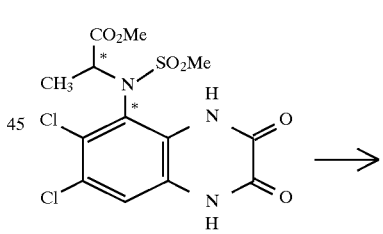

N-(1,4-Dihydro-6,7-dichloro-2,3-dioxoquinoxalin-5-yl)-N-(1-methoxycarbonylethyl)methanesulphonamide (from Example 81, 110 mg, 0.27 mmol) in 33% methylamine in ethanol (6 ml) was heated at 100° C. for 5 h in a sealed vessel, cooled and added to 2M hydrochloric acid (400 ml). The resulting solid was filtered off, dissolved in 1M sodium hydroxide, precipitated with 2M hydrochloric acid and filtered off to give the title compound, as a mixture of diastereomers (63 mg, 57%) m.p. 250° C. (dec). Analysis %: Found: C,37.98; H,3.37; N,13.19. $C_{13}H_{14}Cl_2N_4O_5S$ requires: C,37.66; H,3.55; N,13.51.

EXAMPLE 83

N-(1 4-Dihydro-7-chloro-6-fluoro-2,3-dioxoguinoxalin-5-yl)-N-(2-hydroxyethyl)methanesulphonamide

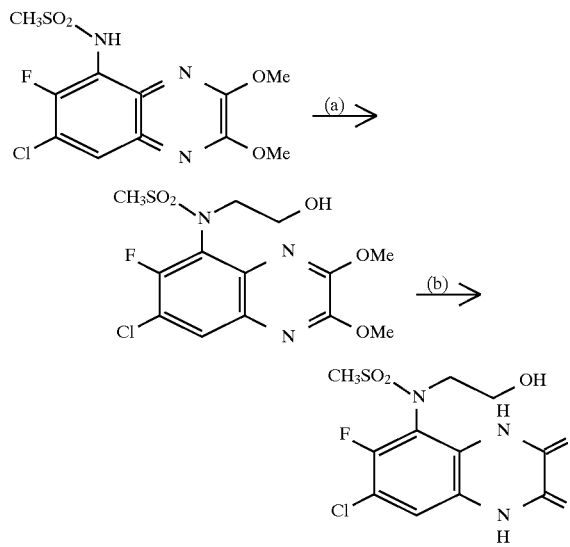

(a) N-(7-Chloro-6-fluoro-2,3-dimethoxyquinoxalin-5-yl) methanesulphonamide (Preparation 25) was converted by the method of Example 17(a) into N-(7-chloro-6-fluoro-2,3-dimethoxyquinoxalin-5-yl)-N-(2-hydroxyethyl)methanesulphonamide. The product was obtained as a white solid (91% yield), m.p. 209°–210° C.

$^1$H NMR (300 MHz, CDCl$_3$): δ=3.18 (3H,s), 3.32 (1H,m), 3.50 (1H,m), 3.74 (2H,m), 4.08 (1H,m), 4.14 (3H,s), 4.20 (3H,s), 7.90 (1H,d,J8 Hz). m/z (thermospray) 380 (MH$^+$).

(b) N-(7-Chloro-6-fluoro-2,3-dimethoxyquinoxalin-5-yl)-N-(2-hydroxyethyl)-methanesulphonamide [from step (a)] was converted by the method of Example 17(b) into N-(1, 4-dihydro-7-chloro-6-fluoro-2,3-dioxoquinoxalin-5-yl)-N-(2-hydroxyethyl) methanesulphonamide. The product was obtained as a white solid (86%), m.p. 298°–300° C.

Analysis %: Found: C,37.44; H,3.00; N,11.79. $C_{11}H_{11}ClFN_3O_5S$ requires: C,37.56; H,3.15; N,11.95%.

EXAMPLE 84

N-(1,4-Dihydro-6-chloro-7-fluoro-2,3-dioxoguinoxalin-5yl)-N-(2-hydroxyethyl)methanesulphonamide

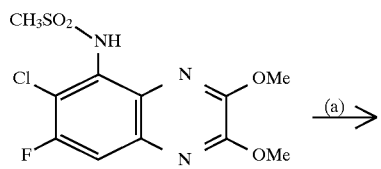

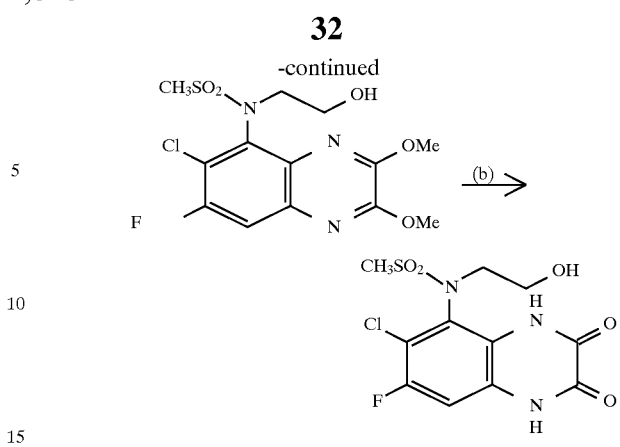

(a) N-(6-Chloro-7-fluoro-2,3-dimethoxyquinoxalin-5-yl) methanesulphonamide (Preparation 26) was converted by the method of Example 17(a) into N-(6-chloro-7-fluoro-2,3-dimethoxyquinoxalin-5-yl)-N-(2-hydroxyethyl)-methanesulphonamide. The product was obtained as a white solid (68% yield).

$^1$H NMR (300 MHz, CDCl$_3$): δ=3.26 (3H,s), 3.50 to 4.10 (4H,m), 4.16 (3H,s), 4.20 (3H,s), 7.60 (1H,d,J10 Hz). m/z (thermospray) 380, 382 (MH$^+$).

(b) N-(6-Chloro-7-fluoro-2,3-dimethoxyquinoxalin-5-yl)-N-(2-hydroxyethyl) methanesulphonamide [from step (a)] was converted by the method of Example 17(b) into N-(1, 4-dihydro-6-chloro-7-fluoro-2,3-dioxo-quinoxalin-5-yl)-N-(2-hydroxyethyl) methanesulphonamide. The product was obtained as a white solid (75% yield), m.p. 290°–291° C.

Analysis %: Found: C,37.62; H,3.10; N,11.88 $C_{11}H_{11}ClFN_3O_5S$ requires: C,37.56; H,3.15; N,11.95%.

EXAMPLE 85

N-(1,4-Dihydro-6,7-dichloro-2,3-dioxoguinoxalin-5-yl)-N-(2-aminoethyl)methanesulphonamide

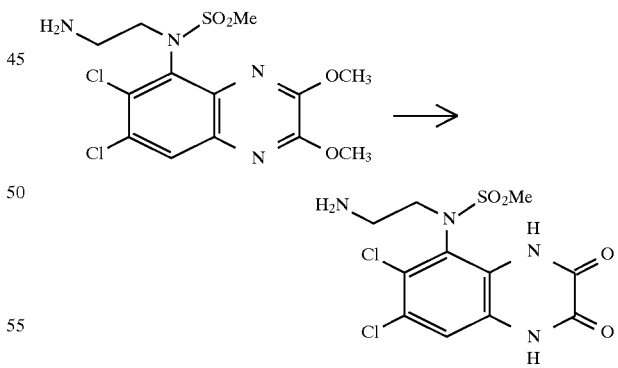

The title compound was prepared from N-(6,7-dichloro-2,3-dimethoxy-quinoxalin-5-yl)-N-(2-aminoethyl) methanesulphonamide (Preparation 27, 40 mg, 0.101 mmol) by the method of Example 7(b) and was obtained as a white solid (18 mg, 48%), m.p. >300° C.

Analysis %: Found: C,31.85; H,3.74; N,13.15. $C_{11}H_{12}Cl_2N_4O_4S.HCL$. $^2/_5H_2O$. $^1/_{10}CH_2Cl_2$ requires: C,31.79; H,3.36; N,13.36%.

EXAMPLE 86

N-(1,4-Dihydro-6,7-dichloro-2,3-dioxoquinoxaline-5-yl)-N-(2-phthalimidoethyl) methanesulphonamide

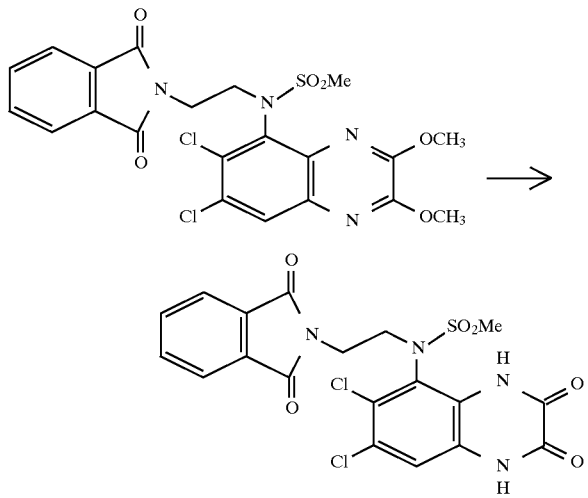

The title compound was prepared by the method of Example 85 from N-(6,7-dichloro-2,3-dimethoxyquinoxalin-5-yl)-N-(2-phthalimidoethyl)-methanesulphonamide (from Preparation 27(a), 150 mg, 0.285 mmol) as a white solid (131 mg, 92%), m.p. >300° C.

$^1$H NMR (300 MHz, d$_6$-DMSO): δ=3.25 (3H,s), 3.70–3.82 (2H,m), 3.91–4.07 (2H,m), 7.25 (1H,s), 7.80 (4H,s), 11.09 (1H,s), 12.15 (1H,s). m/z (thermospray) 497 (MH$^+$).

EXAMPLE 87

N-(1,4-Dihydro-6,7-dichloro-2,3-dioxoguinoxalin-5-yl)-N-(2-(N'-trifluoromethanesulphonyl) aminoethyl)methanesulphonamide

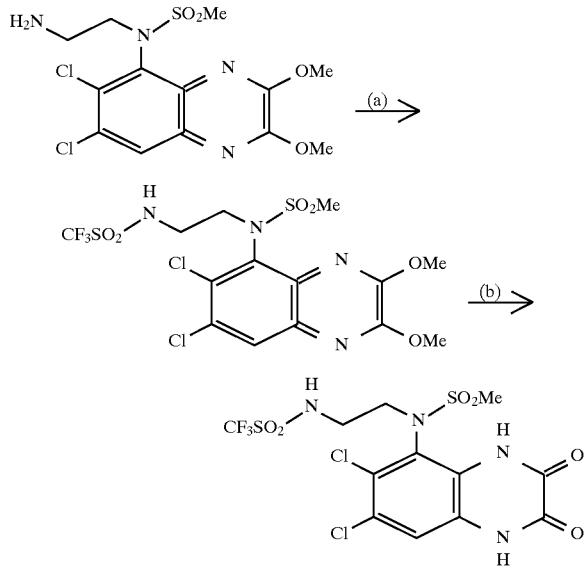

(a) Triethylamine (13 μl, 8 mg, 0.139 mmol) and then trifluoromethanesulphonic anhydride (223 μl, 39 mg, 0.139 mmol) were added dropwise to a stirred solution of N-(6,7-dichloro-2,3-dimethoxyquinoxalin-5-yl)-N-(2-aminoethyl)-methanesulphonamide (from Preparation 27, 50 mg, 0.126 mmol) in dichloromethane (1.5 ml) at −78° C. under nitrogen. The mixture was stirred for 30 minutes and was then allowed to warm to room temperature. The mixture was washed with water, saturated sodium bicarbonate solution and brine and then dried (MgSO$_4$). Concentration under reduced pressure gave N-(6,7-dichloro-2,3-dimethoxyquinoxalin-5-yl)-N-(2-(N'-trifluoromethanesulphonyl) aminoethyl) methanesulphonamide as a pale yellow solid (50 mg, 75%).

$^1$H NMR (300 MHz, CDCl$_3$): δ=3.20 (3H,s), 3.20–3.30 (1H,m), 3.52–3.62 (1H,m), 3.86–3.96 (1H,m), 4.04–4.17 (1H,m), 4.18 (3H,s), 4.23 (3H,s), 8.00 (1H,s). m/z (thermospray) 527 (MH$^+$).

(b) The title compound was prepared by the method of Example 7(b) from N-(6,7-dichloro-2,3-dimethoxyquinoxalin-5-yl)-N-(2-(N'-trifluoromethanesulphonyl) aminoethyl) methanesulphonamide [from step (a)] as a solid (60%), m.p. 203.8°–207.7° C.

Analysis %: Found: C,29.13; H,2.77; N,9.96; C$_{12}$H$_{11}$N$_4$S$_2$O$_6$Cl$_2$F$_3$. H$_2$O. $^3/_{10}$Et$_2$O requires: C,29.39; H,2.99; N,10.38.

EXAMPLE 88

N-(1,4-Dihydro-6,7-dichloro-2,3-dioxoquinoxalin-5-yl-N-(2-[methylaminocarbonyl]aminoethyl) methanesulphonamide

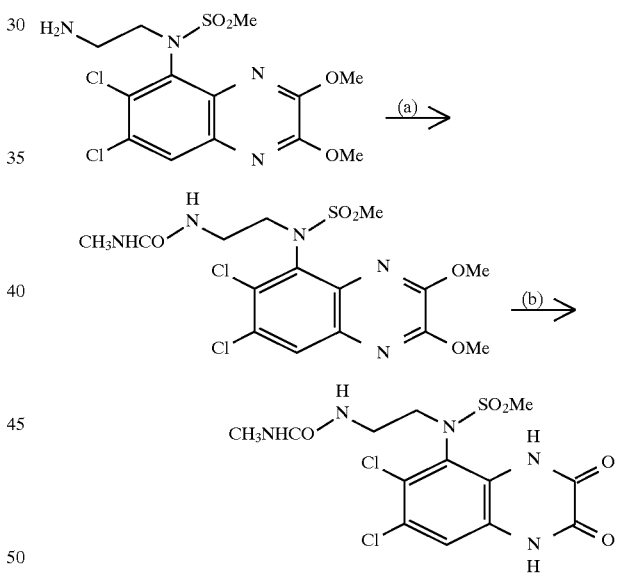

(a) Methylisocyanate (8.2 μl, 8.0 mg, 0.14 mmol) was added to a solution of N-(6,7-dichloro-2,3-dimethoxyquinoxalin-5-yl)-N-(2-aminoethyl)-methanesulphonamide (from Preparation 27, 50 mg, 0.127 mmol) in dichloromethane (2 ml) at room temperature under nitrogen. After 30 minutes the mixture was concentrated under reduced pressure. The residue was dissolved in ethyl acetate and concentrated under reduced pressure to give N-(6,7-dichloro-2,3-dimethoxyquinoxalin-5-yl)-N-(2-[methylaminocarbonyl]aminoethyl) methanesulphonamide as a pale yellow foam (52 mg, 91%).

$^1$H NMR (300 MHz, CDCl$_3$): δ=2.74 (3H,d,J2 Hz), 3.18 (3H,s), 3.36 (2H,m), 3.92 (2H,m), 4.15 (3H,s), 4.17 (3H,s), 4.2 (1H,br s), 5.14 (1H,br s), 7.96 (1H,s). m/z (thermospray) 452 (MH$^+$).

(b) The title compound was prepared by the method of Example 7(b) from N-(6,7-dichloro-2,3-dimethoxyquinoxalin-5-yl)-N-(2-[methylaminocarbonyl]aminoethyl)methanesulphonamide [from step (a)] as a pale yellow foam (60%).

Analysis %: Found: C,32.90; H,3.90; N,14.50. $C_{13}H_{15}N_5O_5Cl_2S.2\frac{1}{2}H_2O$ requires: C,33.27; H,4.30; N,14.92%.

$^1$H NMR (300 MHz, $d_6$-DMSO) δ=2.43 (3H,s), 3.21 (3H,s), 3.59–3.65 (2H,m), 3.75–3.86 (2H,m), 7.40 (1H,s), 10.60 (1H,s), 12.11 (1H,s).

EXAMPLE 89

N-(1,4-dihydro-6,7-dichloro-2,3-dioxoquinoxalin-5-yl)-N-(5-tetrazolylmethyl) methanesulphonamide

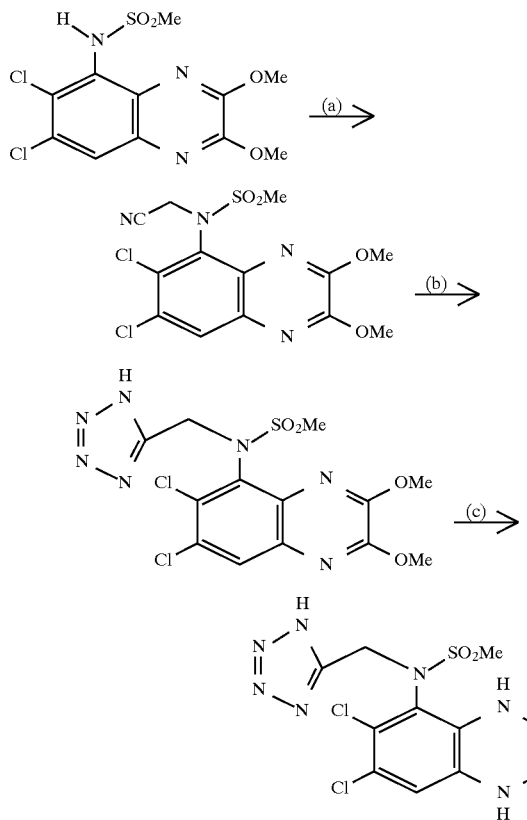

(a) Chloroacetonitrile (233 μl, 279 mg, 3,69 mmol) was added to a refluxing mixture of N-(6,7-dichloro-2,3-dimethoxyquinoxalin-5-yl)methane-sulphonamide (from Preparation 3, 1.00 g, 2.84 mmol) and potassium carbonate (0.47 g, 3.41 mmol) in acetone (50 ml) under nitrogen. The mixture was refluxed for 18 h and was then allowed to cool, and was partitioned between ethyl acetate (500 ml) and water (500 ml). The organic phase was dried (MgSO$_4$) and concentrated under reduced pressure. The residue was purified by flash chromatography (eluting with 0–100% ethyl acetate in hexane and then 5% methanol in dichloromethane) to give N-(6,7-dichloro-2,3-dimethoxyquinoxalin-5-yl)-N-(cyanomethyl) methane-sulphonamide as an off-white solid (600 mg, 54%).

$^1$HNMR (300 MHz, DMSO-$d_6$): δ=3.31 (3H,s), 4.07 (3H,s), 4.08 (3H,s), 4.84 (1H,d,J=19 Hz), 5.10 (1H,d,J=19 Hz), 8.11 (1H,s).

(b) A mixture of N-(6,7-dichloro-2,3-dimethoxyquinoxalin-5-yl)-N-(cyanomethyl) methanesulphonamide (100 mg, 0.256 mmol) and tributyltin azide (170 mg, 0.512 mmol) (Synthesis, 1976, 329) in toluene (10 ml) was heated at reflux for 18 hours. After cooling the mixture was concentrated under reduced pressure and the residue purified by flash chromatography (gradient elution from dichloromethane to 90:10:1 dichloromethane:methanol:ammonia) to give N-(6,7-dichloro-2,3-dimethoxyquinoxalin-5-yl)-N-(5-tetrazolylmethyl) methanesulphonamide as an off-white solid (78 mg, 70%).

$^1$HNMR (300 MHz, CDCl$_3$): δ=3.30 (3H,s), 4.14 (3H,s), 4.18 (3H,s), 5.12 (1H,d,J16 Hz), 5.31 (1H,d,J16 Hz), 7.99 (1H,s). m/z (thermospray) 434 (MH$^+$).

(c) The title compound was prepared by the method of Example 7(b) from N-(6,7-dichloro-2,3-dimethoxyquinoxalin-5-yl)-N-(5-tetrazolylmethyl)-methanesulphonamide, but triturating with water instead of ether, to give a white solid (66%), m.p. >300° C.

Analysis %: Found: C,32.79; H,2.15; N,23.25. $C_{11}H_9N_7O_4Cl_2S.\frac{1}{10}$Dioxane requires: C,32.99; H,2.38; N,23.62%.

EXAMPLE 90

(1,4-Dihydro-6,7-dichloro-2,3-dioxoguinoxalin-5-yl) methyl methyl sulphone

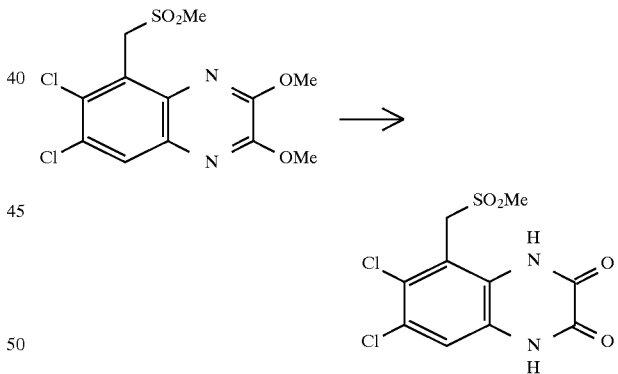

A mixture of (6,7-dichloro-2,3-dimethoxyquinoxalin-5-yl)methyl methyl sulphone (80 mg, 0.228 mmol) (Preparation 29), 2M hydrochloric acid (1 ml) and dioxane (3 ml) was heated at reflux for 3 h, cooled and concentrated under reduced pressure. The residue was diluted with water and the white solid obtained was collected by filtration, washed with water and ether and dried under reduced pressure at 60° C. to give the title compound (58 mg, 79%) as a white solid, m.p. >300° C.

Analysis %:—Found: C,37.35; H,2.35; N,8.44. $C_{10}H_8N_2O_4Cl_2S$ requires: C,37.17; H,2.50; N8.67%.

EXAMPLE 91

(1,4-Dihydro-6,7-dichloro-2,3-dioxoquinoxaline-5-yl)methyl ethyl sulphone

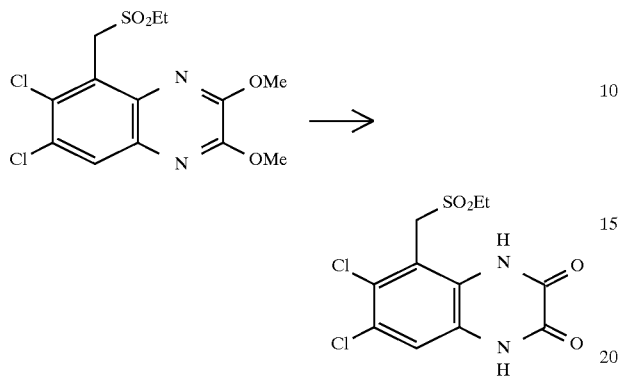

The title compound was prepared from (6,7-dichloro-2,3-dimethoxyquinoxalin-5-yl)methyl ethyl sulphone (Preparation 30) by the method of Example 90 and was obtained as a white solid (65%), m.p. >300° C.

Analysis %: Found: C,39.21; H,2.99; N,8.25; S,9.70. $C_{11}H_{10}N_2O_4Cl_2S$ requires: C,39.18; H,2.99; N,8.31; S,9.51%.

EXAMPLE 92

(1,4-Dihydro-6,7-dichloro-2,3-dioxoquinoxalin-5-yl) methyl benzyl sulphone

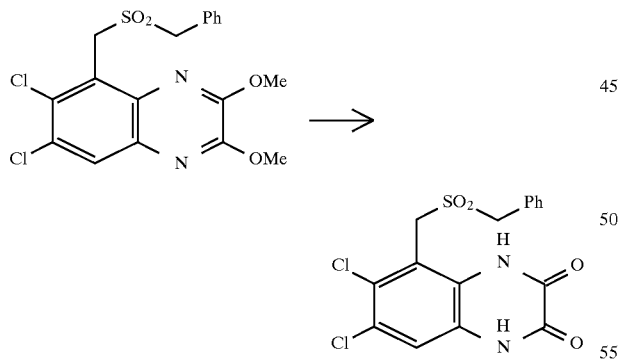

The title compound was prepared from (6,7-dichloro-2,3-dimethoxyquinoxalin-5-yl) methyl benzyl sulphone (Preparation 31) by the method of Example 90 and was obtained as a white solid (92%), m.p. >300° C.

Analysis %: Found: C,48.30; H,3.12; N,6.65. $C_{16}H_{12}N_2O_4Cl_2S$ 0.2 dioxane requires: C,48.40; H,3.29; N,6.72%.

EXAMPLE 93

1-(1,4-Dihydro-6,7-dichloro-2,3-dioxoquinoxaline-5-yl)-3-butenyl methyl sulphone

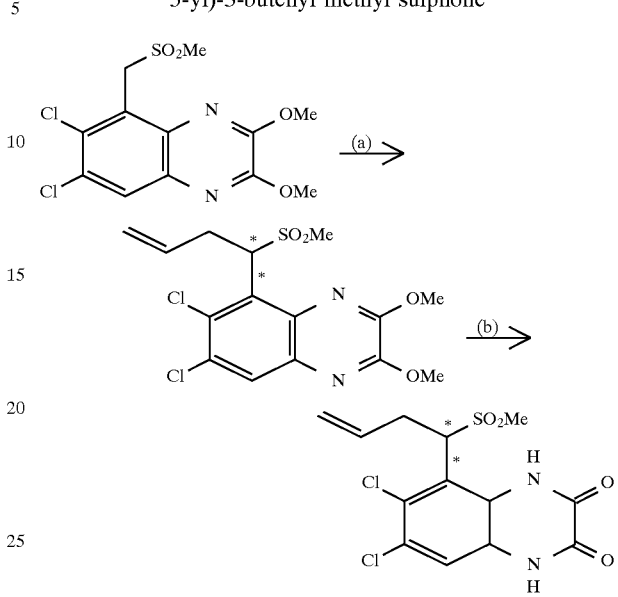

(a) A solution of (6,7-dichloro-2,3-dimethoxyquinoxalin-5-yl)methyl methyl sulphone (50 mg, 0.142 mmol) (Preparation 29) and diallyl carbonate (41 μl, 40 mg, 0.285 mmol) in dry tetrahydrofuran (0.8 ml) was added via cannula to a mixture of tris(dibenzylideneacetone)dipalladium (0 ml).chloroform adduct (7.4 mg, 0.007 mmol) and 1,2-bis (diphenylphosphino)ethane (11.3 mg, 0.028 mmol) in dry tetrahydrofuran (0.6 ml) under nitrogen at room temperature. The mixture was stirred at room temperature for 5 minutes and then at reflux for 2 hours. The mixture was allowed to cool, was diluted with dichloromethane and concentrated under reduced pressure. The residue was purified by flash chromatography (eluting with 3:1 hexane:ethyl acetate) to give 1-(6,7-dichloro-2,3-dimethoxyquinoxalin-5-yl)-3-butenyl methyl sulphone as a mixture of diastereoisomers (approximately 20:1 by $^1$HNMR) as a white foam (29 mg, 52%).

$^1$HNMR (300 MHz, CDCl$_3$): δ=(major diastereoisomer only) 2.93 (3H,s), 3.36 (1H,m), 3.84 (1H,m), 4.16 (3H,s), 4.25 (3H,s), 5.00 (2H,m), 5.45 (1H,m), 5.60(1H,m), 7.96 (1H,s). m/z (thermospray) 391 (MH$^+$).

(b) A mixture of 1-(6,7-dichloro-2,3-dimethoxyquinoxalin-5-yl)-3-butenyl methyl sulphone (from step (a), 27 mg, 0.069 mmol), 2M hydrochoric acid (0.5 ml) and dioxane (1 ml) was warmed at 90° C. for 15 h, cooled and concentrated under reduced pressure. The residue was sonicated with ether and a few drops of methanol and the resulting white solid was collected by filtration, washed with ether and dried to afford the title compound (17 mg, 68%) as a white powder, m.p. 270.5–272° C.

Analysis %: Found: C,42.98; H,3.35; N,7.45. $C_{13}H_{12}N_2Cl_2O_4S$ requires: C,42.99; H,3.33; N,7.71%.

EXAMPLE 94

1-(1,4-Dihydro-6,7-dichloro-2,3-dioxoguinoxalin-5-yl)-3-hydroxypropyl methyl sulphone

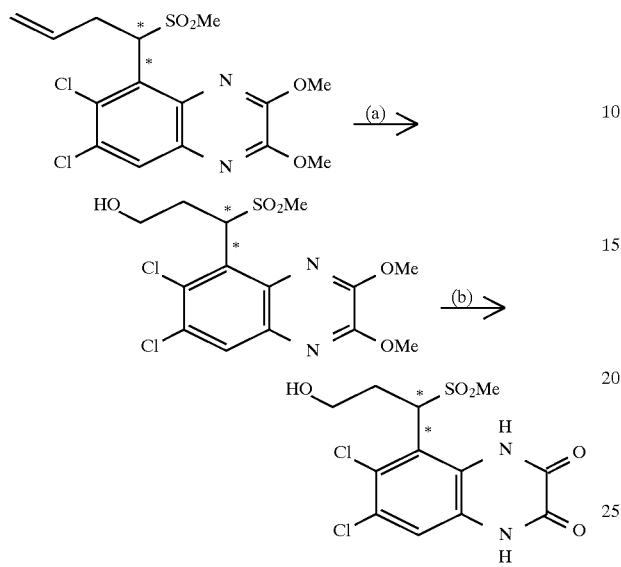

(a) Ozone was bubbled through a solution of 1-(6,7-dichloro-2,3-dimethoxyquinoxalin-5-yl)-3-butenyl methyl sulphone (50 mg, 0.128 mmol) [Example 93(a)] in dry dichloromethane (1.3 ml) at −78° C. until a blue colour developed. The mixture was stirred for 5 minutes and was then purged with a stream of oxygen and then nitrogen. Methanol (1.3 ml) was added and the mixture allowed to equilibrate at −78° C. before sodium borohydride (12 mg, 0.319 mmol) was added in two portions. The mixture was stirred for 5 mins and was then allowed to warm to room temperature. The mixture was poured into 2M hydrochloric acid (20 ml) and extracted with dichloromethane (2×20 ml). The combined extracts were washed with brine (20 ml), dried (MgSO$_4$) and concentrated under reduced pressure. The residue was purified by flash chromatography (eluting with 1:1 hexane:ethyl acetate) to give 1-(6,7-dichloro-2,3-dimethoxyquinoxalin-5-yl)-3-hydroxypropyl methyl sulphone (35.6 mg, 70%) as a white foam.

$^1$H NMR (300 MHz, CDCl$_3$): δ=2.96 (3H,s), 3.05 (2H,m), 3.51 (1H,m), 3.87 (1H,m), 4.15 (3H,s), 4.22 (3H,s), 5.18 (1H, dd, J 6,8 Hz), 7.98 (1H,s) m/z (thermospray) 395 (MH$^+$).

(b) A mixture of 1-(6,7-dichloro-2,3-dimethoxyquinoxalin-5-yl)-3-hydroxypropyl methyl sulphone (step (a)) (32.4 mg, 0.082 mmol), 2M hydrochloric acid (0.5 ml) and dioxane (1 ml) was heated at reflux for 16 hours, cooled and concentrated under reduced pressure. The residue was sonicated with ether and the resulting solid collected by filtration, washed with ether and dried under reduced pressure at 60° C. to give the title compound (24.7 mg, 82%) as a pale yellow solid, m.p. 267°–269° C.

Analysis %: Found: C,39.12; H,3.21; N,7.81. C$_{12}$H$_{12}$N$_2$Cl$_2$O$_5$S requires: C,39.25; H,3.29; N,7.63%.

EXAMPLE 95

1-(1,4-Dihydro-6,7-dichloro-2,3-dioxoguinoxalin-5-yl-4-hydroxybutyl methyl sulphone

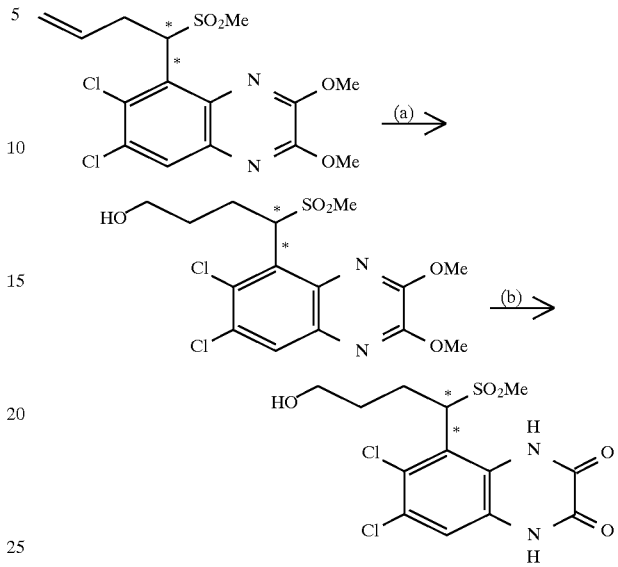

A solution of 9-borabicyclo[3.3.1]nonane in tetrahydrofuran (0.5M, 1.07 ml, 0.537 mmol) was added to a stirred solution of 1-(6,7-dichloro-2,3-dimethyoxyquinoxalin-5-yl)-3-butenyl methyl sulphone (Example 93 (a)) (200 mg, 0.511 mmol) at room temperature under nitrogen. The mixture was stirred for 20 hours and then trimethylamine N-oxide (119 mg, 1.58 mmol) was added in portions. The mixture was stirred at room temperature for 2 hours and then at reflux for 30 minutes, cooled and concentrated under reduced pressure. The residue was purified by flash chromatography (eluting with 1:1 hexane:ethyl acetate then neat ethyl acetate) to give 1-(6,7-dichloro-2,3-dimethoxyquinoxalin-5-yl)-4-hydroxybutyl methyl sulphone (120 mg, 57%) as a mixture of diastereoisomers (by $^1$HNMR).

$^1$H NMR (300 MHz, CDCl$_3$): δ=(major diastereoisomer only) 1.29 (1 H,m), 1.40 (1H,m), 2.66 (1H,m), 2.89 (3H,s), 3.26 (1H,m), 3.65 (2H,m), 4.15 (3H,s), 4.22 (3H,s), 5.42 (1H,dd,J6,8 Hz), 7.98 (1H,s). m/z (thermospray) 409 (MH$^+$).

(b)The title compound was prepared from 1-(6,7-dichloro-2,3-dimethoxyquinoxalin-5-yl)-4-hydroxybutyl methyl sulphone (step (a), 92 mg, 0.225 mmol) by the method of Example 94 (b) and sonication with a mixture of ether, methanol and aiisopropyl ether to give a pale grey solid (43 mg, 53%), m.p. 306°–307.5° C. (single unassigned diastereoisomer by $^1$HNMR).

Analysis %: Found: C,41.06; H,3.76; N,7.26; C$_{13}$H$_{14}$Cl$_2$N$_2$O$_5$S requires: C, 40.96; H,3.70; N,7.35%.

$^1$H NMR (300 MHz, d$_6$-DMSO): δ=1.15 (1H,m), 1.32 (1H,m), 2.20 (1H,m), 2.37 (1H,m), 3.30 (5H, obscured, m), 5.32 (1H,dd,J6,8 Hz), 7.38 (1H,s), 10.31 (1H,s), 12.12 (1H,s).

EXAMPLE 96

The binding affinity for the glycine site of the NMDA receptor of some of the compounds of the examples were determined in test (a) above, and those found to have an IC$_{50}$ of less than 50 nM included the compounds of the following examples: 1, 8, 17, 29, 40, 56, 70, 80(b) (first compound) and 80(d).

PREPARATION OF SYNTHETIC INTERMEDIATES PREPARATION 1

5-Amino-6,7-dichloro-2,3-dimethoxyquinoxaline

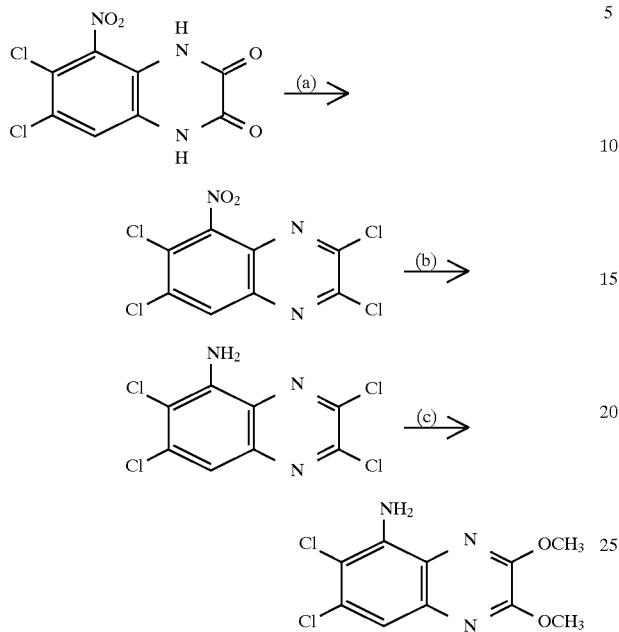

(a) A mixture of 6,7-dichloro-1,4-dihydro-5-nitroquinoxalin-2,3-dione (Example 1 of WO-A-94/00124, 84 g, 0.34 mol), thionyl chloride (840 ml) and dimethylformamide (0.5 ml) was heated at reflux for 3 hours, cooled and concentrated under reduced pressure. Ethyl acetate (300 ml) was added and removed under reduced pressure, followed by petroleum ether (b.p. 100°–120° C.). The solid residue was recrystallised from petroleum ether (b.p. 100°–120° C.) to give 2,3,6,7-tetrachloro-5-nitro-quinoxaline (78 g, 73%) as a light yellow solid.

$^1$H-NMR (300 MHz, CDCl$_3$): δ=8.6 (1H, s).

(b) Tin (II) chloride dihydrate (346.3 g, 1.54 mol) was added to a solution of the product from (a) above (96.2 g, 0.31 mol) in ethyl acetate (1.8 l). The mixture was heated under reflux for 4 hours, cooled and poured cautiously into an excess of aqueous saturated sodium bicarbonate. The mixture was filtered through "Celite", (Trade Mark), washing well with ethyl acetate. The filter cake was macerated with more ethyl acetate and the solid material filtered off. The combined ethyl acetate solutions were dried (MgSO$_4$) and concentrated under reduced pressure to give 5-amino-2,3,6,7-tetrachloroquinoxaline (73.4 g, 84%) as a yellow solid.

$^1$H NMR (300 MHz, CDCl$_3$): δ=5.45 (2H, br, s), 7.47 (1H, s). m/z (thermospray) 385 (MH$^+$).

(c) A solution of sodium methoxide (25% solution in methanol, 274 ml, 1.28 mol) was added to a suspension of 5-amino-2,3,6,7-tetrachloroquinoxaline (72.4 g, 0.256 mol) in dry methanol (1 l) and the resulting mixture was heated at reflux for 30 minutes. The mixture was cooled, concentrated under reduced pressure, and the residue partitioned between water and ethyl acetate (total of 8 l). The organic solution was dried (MgSO$_4$) and concentrated under reduced pressure. The crude product was purified by trituration with methanol, followed by dissolution in dichloromethane (2 l) and filtration. The filtrate was concentrated under reduced pressure to give the title compound as a yellow solid (55.0 g, 79%).

$^1$H NMR (300 MHz, CDCl$_3$): δ=4.13 (3H, s), 4.14 (3H, s), 5.07 (2H, br s), 7.26 (1H, s). m/z (thermospray) 274 (MH$^+$).

PREPARATION 2

5-Amino-2,3-dimethoxy-6,7-dimethyl quinoxaline

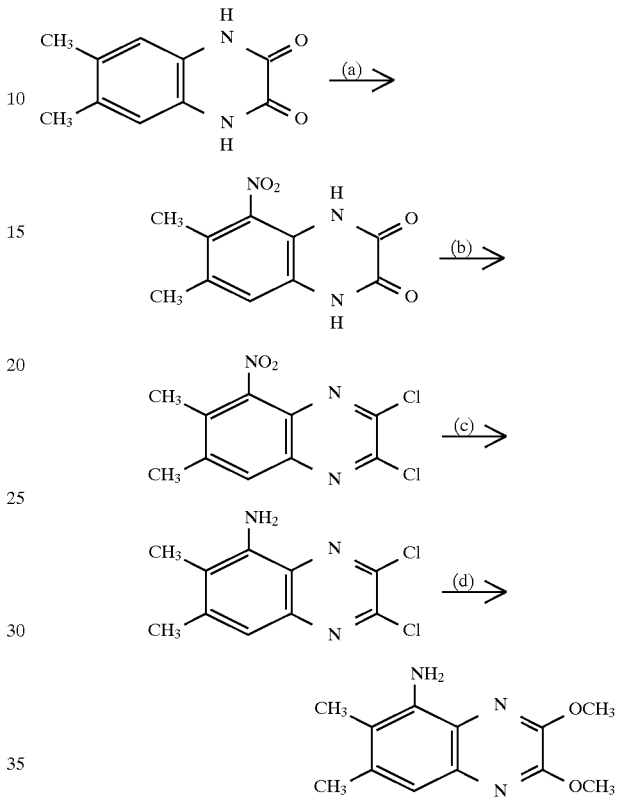

(a) 1,4-Dihydro-6,7-dimethylquinoxalin-2,3-dione (10.0 g, 52.6 mmol —see J. Liebigs Ann. Chem., 1982, 754–761) was added in portions over 10 minutes to concentrated nitric acid (density, 1.42 gcm$^{-3}$, 100 ml) at 0° C. After 5 minutes, the cooling bath was removed and the mixture was stirred at 20° C. for 7 hours, using cooling when necessary. The solution was poured into iced water, and the resulting solid filtered off and dried in vacuo at 75° C. to give 1,4-dihydro-6,7-dimethyl-5-nitroquinoxalin-2,3-dione (7.44 g, 60%) as a pale yellow solid, m.p. 280–290° C. (dec.) from dimethylformamide/water).

$^1$H-NMR (300 MHz, DMSO-d$_6$): δ=2.08 (3H, s), 2.25 (3H, s), 7.06 (1H, s), 11.70 (1H, br, s), 12.06 (1H, br, s). ν$_{max.}$ (KBr) 3185, 1703, 1533, 1400, 1355 cm$^{-1}$. m/z (thermospray) 253 (MNH$_4^+$).

(b) A mixture of 1,4-dihydro-6,7-dimethyl-5-nitroquinoxalin-2,3-dione (from step (a), 7.44 g, 31.6 mmol), thionyl chloride (69.2 ml, 0.949 mol) and dimethylformamide (0.25 ml, 3.16 mmol) was heated at reflux for 3 hours, cooled, and added gradually to a vigorously stirred mixture of ice and water (1.2 l) over 15 minutes. The resulting precipitate was filtered off and dried in vacuo at 80° C. to afford 2,3-dichloro-6,7-dimethyl-5-nitroquinoxaline (8.34 g, 97%), as a pale orange solid, m.p. 133°–134° C.

$^1$H NMR (300 MHz, DMSO-d$_6$): δ=2.38 (3H, s), 2.54 (3H, s), 8.12 (1H, s). ν$_{max.}$ (KBr) 1537, 1388, 1377, 1269, 1163 cm$^{-1}$. m/z (thermospray) 289 (MNH$_4^+$).

(c) A mixture of 2,3-dichloro-6,7-dimethyl-5-nitroquinoxaline (from step (b), 8.33 g, 30.6 mmol) and stannous chloride dihydrate (34.54 g, 153 mmol) in ethyl acetate (300 ml) was heated at reflux for 11 hours. A further portion of stannous chloride dihydrate (13.82 g, 61.2 mmol) was added and the mixture was heated for 2 hours, cooled and diluted with ethyl acetate (500 ml). The mixture was added to saturated aqueous sodium bicarbonate (200 ml) and filtered, washing the filter cake well with ethyl acetate. The organic layer was separated, washed with saturated aqueous sodium bicarbonate (3×100 ml), dried (MgSO$_4$) and concentrated under reduced pressure. The residue was purified by flash chromatography (gradient elution with methanol/dichloromethane) to afford 5-amino-2,3-dichloro-6,7-dimethylquinoxaline (6.15 g, 83%), as an orange solid, m.p. 178–180° C.

$^1$H-NMR (300 MHz, DMSO-d$_6$): δ=2.38 (3H, s), 2.54 (3H, s), 8.12 (1H, s). ν$_{max.}$ (KBr) 3475, 1613, 1267, 1178 cm$^{-1}$. m/z (thermospray) 242 (MNH$_4{}^+$).

(d) Sodium methoxide (25% solution in methanol, 13.9 ml, 61 mmol) was added over 12 minutes to a stirred solution of 5-amino-2,3-dichloro-6,7-dimethylquinoxaline (from step (c), 6.15 g, 25.4 mmol) in dry tetrahydrofuran (250 ml) under nitrogen at 0° C. The mixture was stirred at 0° C. for 20 minutes, and at room temperature for 72 hours. The mixture was diluted with ethyl acetate (750 ml), washed with water (2× 250 ml) and brine (250 ml), dried (MgSO$_4$), and concentrated under reduced pressure. The residue was purified by flash chromatography (gradient elution with hexane/dichloromethane) to give the title compound as a white solid (4.55 g, 77%), m.p. 166°–167° C.

$^1$H NMR (300 MHz, CDCl$_3$): δ=2.32 (3H, s), 2.35 (3H, s), 4.14 (3H, s), 4.15 (3H, s), 5.06 (2H, br, s), 7.06 (1H, s). ν$_{max.}$ (KBr) 3540, 2950, 1600, 1535, 1395, 1335, 1240 cm$^{-1}$. m/z (thermospray) 234 (MH$^+$).

PREPARATION 3

N-(6.7-Dichloro-2,3-dimethoxyquinoxalin-5-Ml) methanesulphonamide

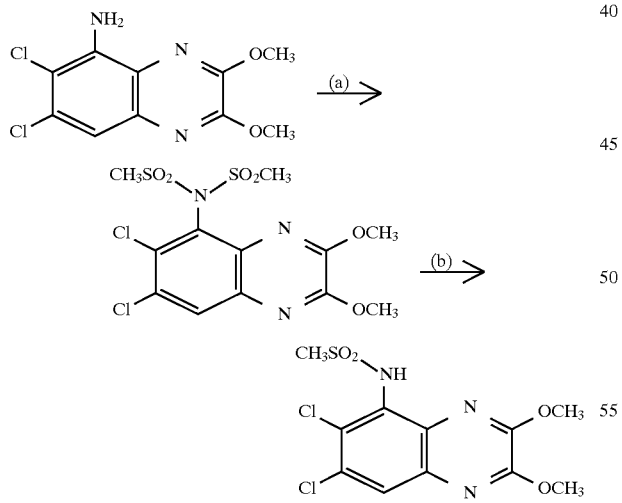

(a) A mixture of 5-amino-6,7-dichloro-2,3-dimethoxyquinoxaline (see Preparation 1) (10.0 g, 36.5 mmol), methanesulphonic anhydride (31.8 g, 183 mmol) and pyridine (14.8 ml, 183 mmol) in dry dichloromethane (150 ml) was stirred at 20° C. for 16 hours. The solvent was removed under reduced pressure and the residue dissolved in a mixture of water (5 ml) and tetrahydrofuran (50 ml). After being stirred for 10 minutes, the solution was partitioned between ethyl acetate and 2M hydrochloric acid.

The combined organic solutions were washed with saturated aqueous sodium bicarbonate, dried (MgSO$_4$), and concentrated under reduced pressure. Purification of the residue by flash chromatography (gradient elution with hexane/dichloromethane) gave 6,7-dichloro-5-di(methanesulphonyl) amino-2,3-dimethoxyquinoxaline as an off-white solid (12.3 g, 78%), m.p. 240°–244° C.

$^1$H NMR (300 MHz, CDCl$_3$): δ=3.62 (6H, s), 4.16 (3H, s), 4.18 (3H, s), 8.02 (1H, s). m/z (thermospray) 430, 432 (MH$^+$).

(b) Aqueous sodium hydroxide (1M, 145 ml, 145 mmol) was added to a suspension of 6,7-dichloro-5-di(methanesulphonyl)amino-2,3-dimethoxyquinoxaline (from step (a), 12.28 g, 28.6 mmol) and the mixture was stirred at room temperature for 16 hours. The resulting orange solution was treated with 2M hydrochloric acid (to pH3) and the solid which precipitated was filtered off, washed with water and ether, and dried in vacuo at 80° C. to give N-(6,7-dichloro-2,3-dimethoxyquinoxalin-5-yl) methanesulphonamide (8.46 g, 84%) as a white solid, m.p. 225°–227° C.

$^1$H NMR (300 MHz, CDCl$_3$): δ=3.42 (3H, s), 4.15 (3H, s), 4.20 (3H, s), 7.15 (1H, br, s), 8.02 (1H, s). m/z (thermospray) 352 (MH$^+$).

PREPARATION 4

N-(6,7-Dichloro-2,3-dimethoxyquinoxalin-5-yl) ethanesulphonamide

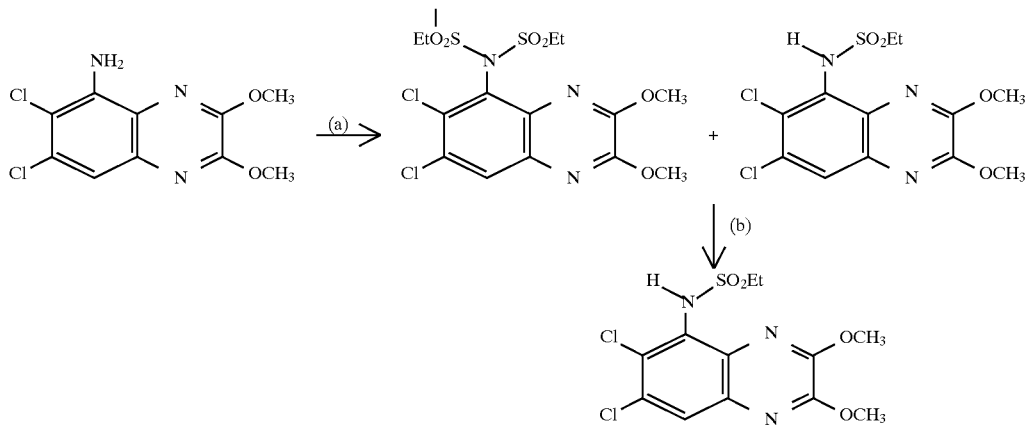

The title compound was prepared by the method of Preparation 3 (a) and (b) using ethanesulphonic anhydride [J Am Chem Soc, 76, 1222 (1954)] and 5-amino-6,7-dichloro-2,3-dimethoxyquinoxaline, and was obtained as a pale yellow solid (47% yield), m.p. 174°–176° C.

$^1$H-NMR (300 MHz, CDCl$_3$): δ=1.38 (3H, t, J 7 Hz), 3.56 (2H, q, J 7 Hz), 4.13 (3H, s), 4.20 (3H, s), 6.97 (1H, brs), 7.85 (1H, s). m/z (thermospray) 366 (MH$^+$).

In this case step (a) resulted in a mixture of products which were treated as in step (b) of Preparation 3.

PREPARATION 5

N-(6,7-Dichloro-2,3-dimethoxyquinoxalin-5-yl)-benzenesulphonamide

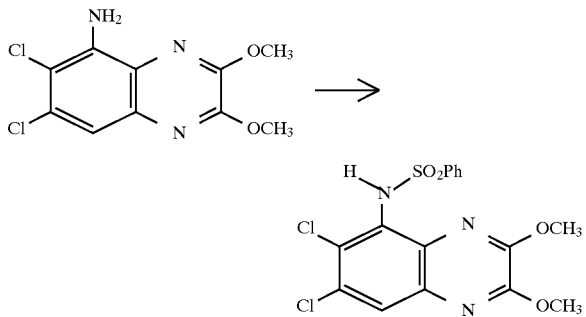

A mixture of 5-amino-6,7-dichloro-2,3-dimethoxyquinoxaline (Preparation 1) (548 mg, 2.0 mmol), benzenesulphonyl chloride (1.28 ml, 10 mmol) and pyridine (0.8 ml, 10 mmol) in dry dichloromethane (30 ml) was stirred at reflux for 100 hours. The mixture was poured into ethyl acetate/water and a white solid was filtered off, washed with water, ethyl acetate, then ether, and dried at 80° C. in vacuo to give the title compound (250 mg, 30%), m.p. 292°–293° C.

$^1$H NMR (300 MHz, DMSO-d$_6$): δ=3.53 (3H, s), 4.02 (3H, s), 7.48 (2H, J 8 Hz), 7.63 (3H, m), 8.00 (1H, s), 10.22 (1H, br, s). m/z (thermospray) 414 (MH$^+$).

PREPARATION 6

N-(2,3-Dimethoxy-6,7-dimethylquinoxalin-5-yl)-methanesulphonamide

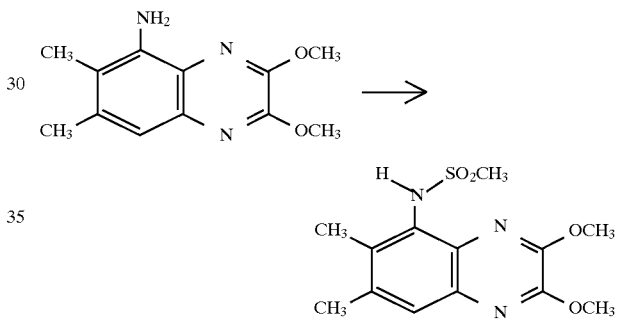

A mixture of 5-amino-2,3-dimethoxy-6,7-dimethylquinoxaline (from Preparation 2) (50 mg, 0.214 mmol), methanesulphonic anhydride (187 mg, 1.07 mmol) and pyridine (87 ml, 1.07 mmol) in dry tetrahydrofuran (1 ml) was stirred at 20° C. for 2.7 hours. Water (0.3 ml) was added, and the mixture was stirred for 40 minutes. The mixture was partitioned between ethyl acetate (15 ml) and 2M hydrochloric acid (5 ml). The organic solution was washed with saturated aqueous sodium bicarbonate (5 ml), dried (MgSO$_4$), and concentrated under reduced pressure to give the title compound (63 mg, 94%) as a white solid, m.p. 219° C.

$^1$H NMR (300 MHz, CDCl$_3$): δ=2.46 (3H, s), 2.55 (3H, s), 2.87 (3H, s), 4.16 (6H, s), 7.00 (1H, br, s), 7.57 (1H, s). ν$_{max.}$ (KBr) 3545, 1480, 1160 cm$^{-1}$. m/z (thermospray) 312 (MH$^+$).

Analysis %: Found C, 50.02; H, 5.48; N, 13.35; S, 10.51. C$_{13}$H$_{17}$N$_3$SO$_4$ requires C, 50.15; H, 5.50; N, 13.50; S, 10.30%.

PREPARATION 7

N-(2,3-Dimethoxy-6,7-dimethylquinoxalin-5-yl)-ethanesulphonamide

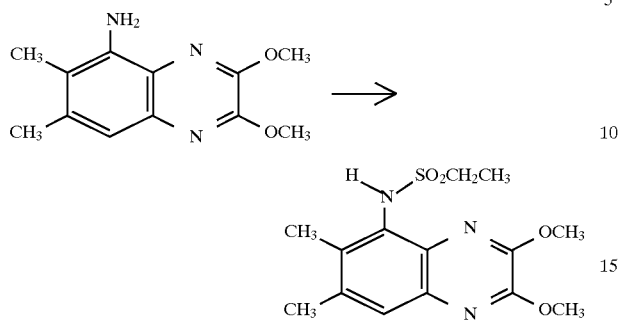

A mixture of 5-amino-2,3-dimethoxy-6,7-dimethylquinoxaline (from Preparation 2) (50 mg, 0.214 mmol), ethanesulphonyl chloride (138 mg, 1.07 mmol) and pyridine (87 μl, 1.07 mmol) in dry tetrahydrofuran (1 ml) was stirred at 20° C. for 3.5 hours. Additional portions of ethanesulphonyl chloride (138 mg, 1.07 mmol) and pyridine (87 ml, 1.07 mmol) were added and the mixture was stirred for a further 4 days. Water (0.6 ml) was added, and the mixture was stirred for 40 minutes. The mixture was partitioned between ethyl acetate (15 ml) and 2M hydrochloric acid (5 ml). The organic solution was washed with water (5 ml), saturated aqueous sodium bicarbonate (5 ml), dried (MgSO$_4$), and concentrated under reduced pressure to give the title compound (67 mg, 96%) as a straw-coloured solid, m.p. 201°–203° C.

$^1$H NMR (300 MHz, CDCl$_3$): δ=1.35 (3H, t, J 7 Hz), 2.44 (3H, s), 2.54 (3H, s), 3.03 (2H, q, J 7 Hz), 4.15 (3H, s), 4.16 (3H, s), 6.96 (1H, br, s), 7.56 (1H, s). ν$_{max}$. (KBr) 3250, 2940, 1480, 1323, 1239, 1157 cm$^{-1}$. m/z (thermospray) 326 (MH$^+$).

Analysis %: Found: C, 51.88; H, 6.02; N, 12.43. C$_{14}$H$_{19}$N$_3$SO$_4$.0.15 ethyl acetate requires: C, 51.79; H, 6.01; N, 12.41%.

PREPARATION 8

N-(6,7-Dichloro-2,3-dimethoxyquinoxalin-5-yl)-N-(2-oxypropyl)methanesulphonamide

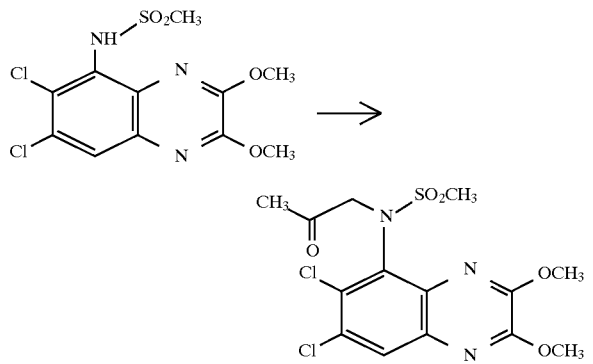

Potassium t-butoxide (246 mg, 2.2 mmol) was added to a stirred solution of N-(6,7-dichloro-2,3-dimethoxyquinoxalin-5-yl)methanesulphonamide (702 mg, 2.0 mmol, see Preparation 3) in dry dimethylformamide (10 ml) under nitrogen at 20° C. Chloroacetone (175 ml, 2.2 mmol) was added, and the mixture was stirred for 4 hours. The mixture was concentrated under reduced pressure, and the residue was partitioned between 1M aqueous sodium hydroxide and ethyl acetate. The organic extracts were combined, washed with brine, dried (Na$_2$SO$_4$) and concentrated under reduced pressure to give a white solid which was triturated with ether, filtered and dried to give the title compound (720 mg, 88%), m.p. 247°–2480° C.

$^1$H NMR (300 MHz, CDCl$_3$): δ=2.23 (3H, s), 3.42 (3H, s), 4.17 (3H, s), 4.23 (3H, s), 4.45 (1H, d, J 18 Hz), 4.74 (1H, d, J 18 Hz), 7.95 (1H, s). m/z (thermospray) 408 (MH$^+$).

PREPARATION 9

(RS)-N-(6,7-Dichloro-2,3-dimethoxyquinoxalin-5-yl)-N-(2-hydroxypropyl)methanesulphonamide

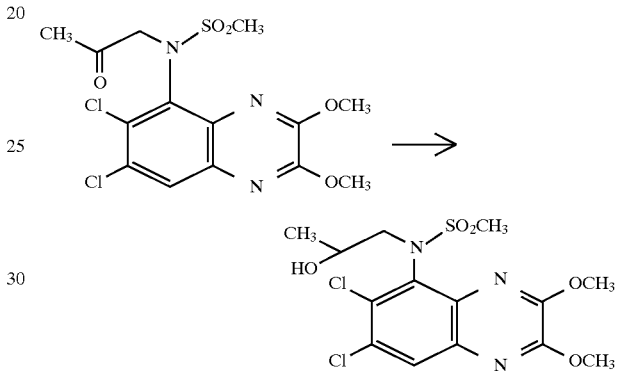

Diisobutylaluminium hydride (1.0M in dichloromethane, 1.0 ml, 1.0 mmol) was added dropwise to a stirred solution of N-(6,7-dichloro-2,3-dimethoxyquinoxalin-5-yl)-N-(2-oxypropyl)-methanesulphonamide (204 mg, 0.5 mmol - Preparation 8) in dry dichloromethane (10 ml) under nitrogen at 20° C. After 4 hours, saturated aqueous ammonium chloride (2 ml) was added and the mixture was stirred for 15 minutes before being filtered through "Arbocel" (Trade Mark) filter aid. The filter cake was washed with dichloromethane, and the filtrate was dried (Na$_2$SO$_4$) and concentrated under reduced pressure. The residue was purified by flash chromatography (gradient elution with hexane/ether) to give the title compound (182 mg, 89%) as a white solid, m.p. 176°–177° C.

Analysis %:—Found: C, 40.67; H, 4.07; N, 10.06. C$_{14}$H$_{17}$Cl$_2$N$_3$O$_5$S requires: C, 40.99; H, 4.18; N, 10.24%.

PREPARATION 10

N-(6,7-Dichloro-2,3-dimethoxyquinoxalin-5-yl)-N-(2-hydroxy-2-methylpropyl) methanesulphonamide

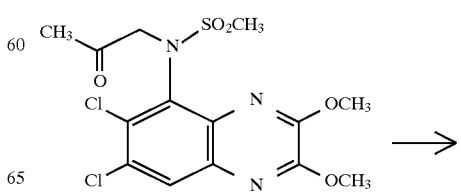

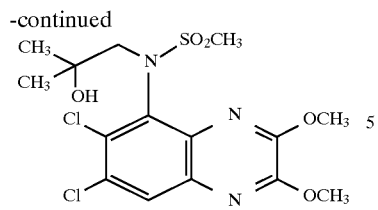

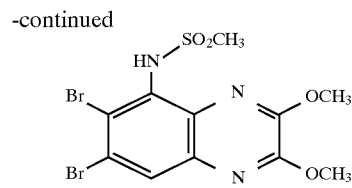

Methylmagnesium bromide (1.4 ml, 1M in di-n-butylether, 1.4 mmol) was added dropwise to a solution of N-(6,7-dichloro-2,3-dimethoxyquinoxalin-5-yl)-N-(2-oxypropyl)methanesulphonamide (143 mg, 0.35 mmol, see Preparation 8) in dry tetrahydrofuran (10 ml) under nitrogen at 5° C. The mixture was allowed to warm slowly to room temperature and stirred for 5 hours. Saturated aqueous ammonium chloride (1 ml) was added and the tetrahydrofuran was removed under reduced pressure. The residue was partitioned between water and ethyl acetate (3 portions). The combined extracts were dried ($Na_2SO_4$), concentrated under reduced pressure, and the residue was purified by flash chromatography (gradient elution with hexane/ether) to give the title compound (105 mg, 75%) as a white solid, m.p. 160° C.

$^1$H NMR (300 MHz, $CDCl_3$): δ=0.97 (3H, s), 1.30 (3H, s), 3.22 (3H, s), 3.56 (1H, s), 3.79 (1H, d, J 15 Hz), 3.96 (1H, d, J 15 Hz), 4.14 (3H, s), 4.19 (3H, s), 7.96 (1H, s). m/z (thermospray) 424 (MH$^+$).

PREPARATION 11

N-(6,7-Dibromo-2,3-dimethoxyquinoxalin-5-yl)-methanesulphonamide

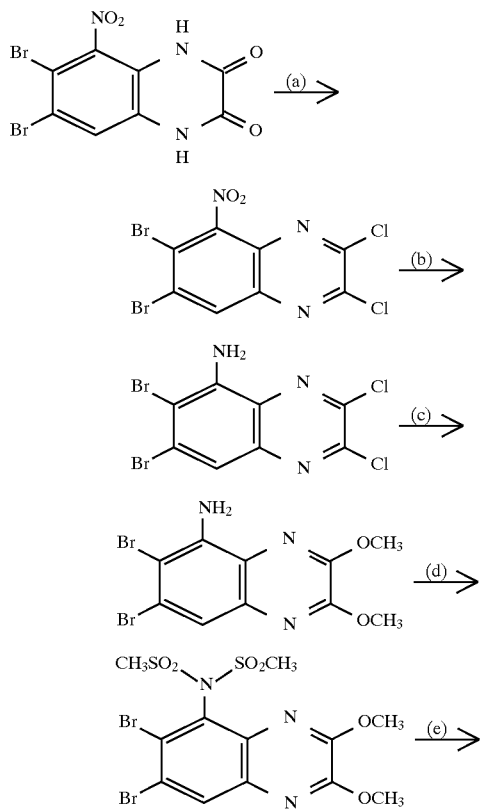

(a) 1,4-Dihydro-6,7-dibromo-5-nitroquinoxalin-2,3-dione (see Example 33, WO-A-94/00124) was converted into 6,7-dibromo-2,3-dichloro-5-nitroquinoxaline by the method of Preparation 1 (a). The product was obtained as an off-white solid (72% yield), m.p. 126°–128° C. (from hexane). $^1$H NMR (300 MHz, $CDCl_3$): δ=8.50 (1H, s).

(b) The intermediate from (a) above was converted into 5-amino-6,7-dibromo-2,3-dichloroquinoxaline by the method of Preparation 1 (b). The product was obtained as a yellow solid (61% yield), m.p. 108°–110° C. (after purification by flash chromatography). $^1$H NMR (300 MHz, $CDCl_3$): δ=5.55 (2H, br s), 7.68 (1H, s).

(c) The intermediate from (b) above was converted into 5-amino-6,7-dibromo-2,3-dimethoxyquinoxaline by the method of Preparation 1 (c). The product was obtained as a yellow solid, (59% yield), m.p. 148°–150° C. (after purification by flash chromatography). $^1$H NMR (300 MHz, $CDCl_3$): δ=4.13 (6H, s), 5.20 (2H, br s), 7.51 (1H, s). m/z (thermospray) 364 (MH$^+$).

(d) The intermediate from (c) above was converted by the method of Preparation 3(a) into 6,7-dibromo-5-di(methanesulphonyl)amino-2,3-dimethoxyquinoxaline (85% yield), as a pale yellow solid, m.p. 204–206 (after purification by flash chromatography). $^1$H NMR (300 MHz, $CDCl_3$): δ=3.61 (6H, s), 4.15 (3H, s), 4.19 (3H, s), 8.20 (1H, s). m/z (thermospray) 520 (MH$^+$).

(e) The intermediate from (d) above was converted into N-(6,7-dibromo-2,3-dimethoxyquinoxalin-5-yl)-methanesulphonamide by the method of Preparation 3(b). The product was obtained as a pale yellow solid (86% yield), m.p. 186°–187° C. $^1$H NMR (300 MHz, $CDCl_3$): δ=3.45 (3H, s), 4.16 (3H, s), 4.21 (3H, s), 7.08 (1H, br, s), 8.09 (1H, s). m/z (thermospray) 442 (MH$^+$).

PREPARATION 12

N-(2,3-Dimethoxy-6,7-dimethylquinoxalin-5-yl)-trifluoromethanesulphonamide

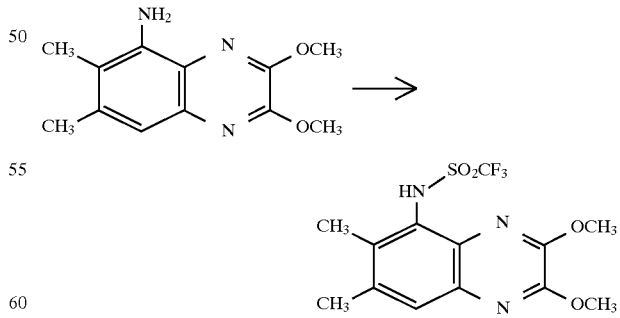

Trifluoromethanesulphonic anhydride (126 ml, 0.75 mmol) was added dropwise to a solution of 5-amino-2,3-dimethoxy-6,7-dimethylquinoxaline (Preparation 2) (170 mg, 0.73 mmol) and triethylamine (112 ml, 0.81 mmol) in dry dichloromethane (15 ml) under nitrogen at −50° C. The mixture was stirred at −30° C. for 2 hours, poured into water and extracted with three portions of dichloromethane. The product was then extracted from the dichloromethane using 1M aqueous sodium hydroxide. The aqueous phase was acidified with excess 2M hydrochloric acid, and the product extracted into dichloromethane (3 portions). The combined extracts were dried (MgSO$_4$) and concentrated under reduced pressure to give a white solid (260 mg, 98%).

$^1$H NMR (300 MHz, CDCl$_3$): δ=2.44 (3H, s), 2.49 (3H, s), 4.14 (3H, s), 4.15 (3H, s), 7.13 (1H, br s), 7.61 (1H, s). m/z (thermospray) 366 (MH$^+$).

PREPARATION 13

N-(6-Chloro-7-ethyl-2,3-dimethoxyquinoxalin-5-yl)methanesulphonamide and N-(7-Chloro-6-ethyl-2,3-dimethoxyquinoxalin-5-yl)methanesulphonamide aqueous sodium chloride (100ml), dried (MgSO$_4$) and concentrated under reduced pressure to give a white solid (2.70 g, >100%) which was used directly without further purification.

$^1$H NMR (300MHz, CDCl$_3$) δ=1.19 (3H,t,J 7 Hz), 2.63 (2H,q,J 7 Hz), 3.30 (4H, br s), 6.57 (1H,s), 6.70 (1H,s).

(b) 1,4-Dihydro-6-chloro-7-ethylquinoxalin-2,3-dione

A mixture of 1,2-diamino-4-chloro-5-ethylbenzene (from (a), 2.70 g, ca 13 mmol), oxalic acid (1.65 g, 18.3 mmol) and 4M hydrochloric acid (66 ml) was heated at reflux for 4.6 h, cooled, and the grey solid collected by filtration and washed with water. The solid was dried in vacuo at 50° C. to afford the title compound (2.34 g, 80%), m.p. >315° C.

Analysis %: Found, C,53.60; H,3.87; N,12.40. C$_{10}$H$_9$ClN$_2$O$_2$ requires: C,53.47; H,4.04; N,12.47%.

$^1$H NMR (300 MHz, DMSO-d$_6$) δ=1.17 (3H,t,J 7 Hz), 2.66 (2H,q, J 7 Hz), 7.05 (1H,s), 7.14 (1H,s), 11.78 (1H, br s), 11.82 (1H, br s).

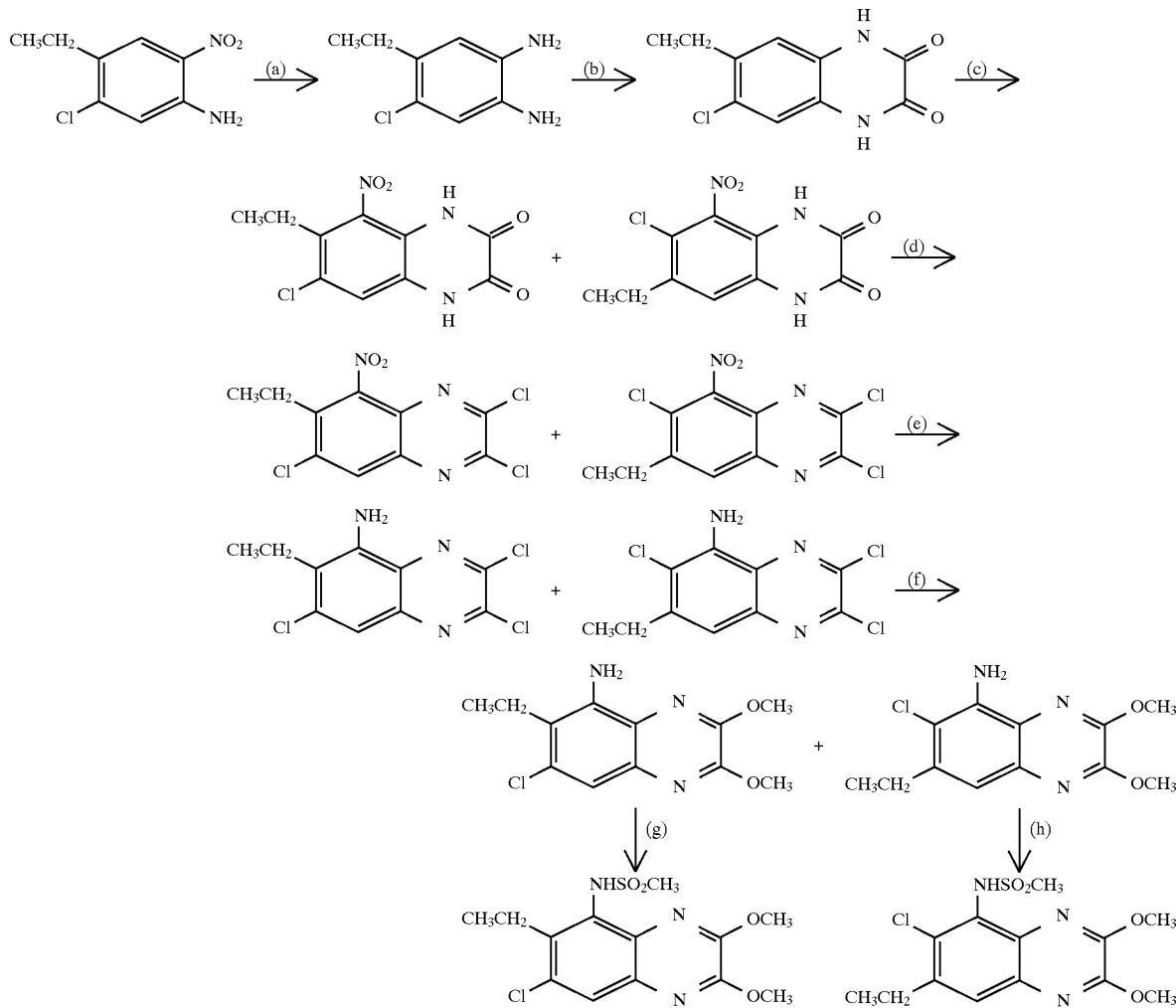

(a) 1,2-Diamino-4-chloro-5-ethylbenzene

A mixture of 5-chloro-4-ethyl-2-nitroaniline (supplied by the Sigma-Aldrich Library of Rare Chemicals, 2.62g, 13.1 mmol), tin (II) chloride dihydrate (14.7 g, 65.3 mmol) and ethyl acetate (130 ml) was heated under reflux for 22 h. The mixture was cooled and partitioned between 1M aqueous sodium hydroxide (500 ml) and ethyl acetate (500 ml). The aqueous layer was extracted with ethyl acetate (250 ml), and the combined organic solutions were washed with saturated (c) 1,4-Dihydro-6-chloro-7-ethyl-5-nitroquinoxalin-2,3-dione and 1.4-Dihydro-7-chloro-6-ethyl-5-nitroquinoxalin-2,3-dione 1,4-Dihydro-6-chloro-7-ethylquinoxalin-2,3-dione (from (b), 2.34 g, 10.4 mmol) was added in small portions over 10 minutes to vigorously stirred concentrated nitric acid (20 ml) at room temperature. The mixture was then heated at 40° C. for 12 h, cooled, and poured into ice water. The yellow solid which formed was filtered off, washed with water, and dried to give the title compounds (2.55 g, 91%), as a mixture (1.7:1 ratio).

$^1$H NMR (300 MHz, DMSO-d$_6$) δ=1.09–1.19 (3H,m), 2.56 (1.3H,q,J 7 Hz), 2.71 (0.7H,q,J 7 Hz), 7.19 (0.4H,s), 7.29 (0.6H,s), 11.95–12.15 (2H, br m). m/z (thermospray) 287 (MNH$_4^+$).

(d) 2,3,7-Trichloro-6-ethyl-5-nitroquinoxaline and 2,3,6-trichloro-7-ethyl-5-nitroquinoxaline A mixture of the quinoxalines from (c) above (2.75 g, 11 mmol), thionyl chloride (28.6 ml, 0.305 mol) and N,N-dimethylformamide (85 μl, 1.0 mmol) was heated under nitrogen at reflux for 24 h. The solution was cooled and cautiously added dropwise to stirred ice-water (600 ml). After 1 h, the beige solid was filtered off, washed with water and dried in vacuo to afford a mixture of the title compounds (2.26 g, 67%). Purification of the mixture by flash chromatography (eluting with hexane:dichloromethane =3:1) permitted isolation of small quantities of the two isomers for characterisation purposes.

The first eluted isomer had m.p. 106°–109° C.

Analysis %: Found C,39.21; H,1.99; N,13.71 C$_{10}$H$_6$Cl$_3$N$_3$O$_2$ requires C,39.18; H,1.97; N,13.71%.

$^1$H NMR (300 MHz, CDCl$_3$) δ=1.41 (3H,t,J 7 Hz), 3.06 (2H,q,J 7Hz), 8.02 (1H,s).

m/z (thermospray) 323 (MH$^+$).

The second isomer had m.p. 88–92° C.

Analysis %: Found C,39.06; H,1.87; N,13.85%

$^1$H NMR (300 MHz, CDCl$_3$) δ=1.35 (3H,t J 8 Hz), 2.98 (2H,q,J 8 Hz), 8.19 (1 H,s).

m/z (thermospray) 323 (MH$^+$).

(e) 5-Amino-2,3,7-trichloro-6-ethylquinoxalin and 5-amino-2,3,6-trichloro-7-ethylquinoxaline A mixture of quinoxalines from (d) above (200 mg, 0.652 mmol), tin (II) chloride dihydrate (1.03 g, 4.57 mmol) and ethyl acetate (6.5ml) was heated under reflux for 4 h, cooled and diluted with ethyl acetate. The solution was washed with 10% aqueous sodium carbonate (25 ml). The aqueous layer was extracted with ethyl acetate (2×25 ml), and the combined organic solutions were washed with 10% aqueous sodium carbonate (2×25 ml), saturated aqueous sodium chloride (25 ml), dried (MgSO$_4$) and concentrated under reduced pressure to give the title compounds as an orange solid (174 mg, 91%), ratio 1:1.

$^1$H NMR (300 MHz, CDCl$_3$) δ=1.25 (1.5H,t, J 8 Hz), 1.37 (1.5H,t,J 8 Hz), 2.84–2.98 (2H,m), 5.05 (1H,br s), 5.28 (1 H, br s), 7.22 (0.5H,s), 7.43 (0.5H,s).

(f) 5-Amino-6-chloro-7-ethyl-2,3-dimethoxyquinoxaline and 5-amino-7-chloro-6-ethyl-2, 3-dimethoxyquinoxaline A mixture of the trichloroquinoxalines from (e) above (169 mg, 0.611 mmol) in anhydrous tetrahydrofuran (6 ml) was treated with a solution of sodium methoxide (0.84 ml, 25% solution in methanol, 1.47 mmol) at 0° C. with stirring. After 3.5 h, the solution was diluted with ethyl acetate, washed with water (2×10 ml), saturated aqueous sodium chloride (10 ml), dried (MgSO$_4$) and concentrated under reduced pressure. Purification by flash chromatography (eluting with hexane/ethyl acetate 19:1) gave two fractions.

The first eluted compound, 5-amino-6-chloro-7-ethyl-2, 3-dimethoxyquinoxaline (42mg, 26%), was obtained as a white solid.

$^1$H NMR (300 MHz, CDCl$_3$) δ=1.32 (3H,t,J8 Hz), 2.87 (2H,q,J 7 Hz), 4.18 (6H,s), 4.90 (2H,br s), 7.08 (1H,s).

The second eluted compound, 5-amino-7-chloro-6-ethyl-2,3-dimethoxy-quinoxaline (57 mg, 35%), was obtained as a pale green solid.

$^1$H NMR (300 MHz, CDCl$_3$) δ=1.14 (3H,t,J 7 Hz), 2.84 (2H,q,J 7 Hz), 4.12 (3H,s), 4.14 (3H,s), 4.70 (2H,br s), 7.22 (1H,s).

(g) N-(6-Chloro-7-ethyl-2,3-dimethoxyquinoxalin-5-yl) methanesulphonamide

Methanesulphonic anhydride (671 mg, 3.85 mmol) was added to a stirred solution of 5-amino-6-chloro-7-ethyl-2,3-dimethoxyquinoxaline (207 mg, 0.77 mmol) and anhydrous pyridine (305 mg, 3.85 mmol) in anhydrous tetrahydrofuran (7.7 ml) at room temperature. After 72 h, water (3 ml) was added and the mixture was stirred for a further 60 minutes. The mixture was diluted with ethyl acetate and washed with 2M hydrochloric acid (50 ml), water (50 ml), saturated aqueous sodium bicarbonate (50 ml) and saturated aqueous sodium chloride (50 ml). The organic phase was dried (MgSO$_4$) and concentrated under reduced pressure to give the title compound (206 mg, 77%).

$^1$H NMR (300 MHz, CDCl$_3$) δ=1.37 (3H,t,J 8 Hz), 2.89–3.00 (2H,m), 3.39 (3H,s), 4.16 (3H,s), 4.19 (3H,s), 7.01 (1H,s), 7.60 (1H,s). m/z (thermospray) 346 (MH$^+$).

(h) N-(7-Chloro-6-ethyl-2,3-dimethoxyquinoxalin-5-yl) methanesulphonamide

5-Amino-7-chloro-6-ethyl-2,3-dimethoxyquinoxaline was converted to the methane sulphonamide derivative by the method of step (g) above. The product was obtained in 47% yield.

$^1$H NMR (300 MHz, CDCl$_3$) δ=1.25 (3H,t,J 8 Hz), 3.00 (3H,s), 3.28 (2H,q,J 7 Hz), 4.17 (3H,s), 4.27 (3H,s), 6.87 (1H,s), 7.83 (1H,s). m/z (thermospray) 346 (MH$^+$).

PREPARATION 14

N-(6-Chloro-2,3-dimethoxy-7-methylquinoxalin-5-yl)methanesulphonamide and N-(7-Chloro-2,3-dimethoxy-6-methylquinoxalin-5-yl) methanesulphonamide

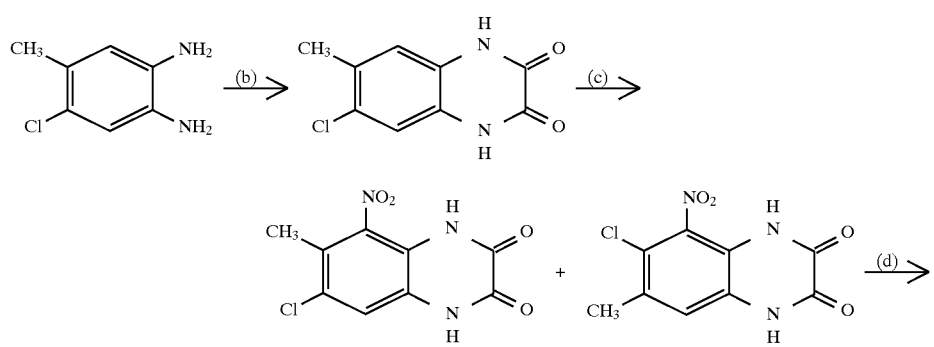

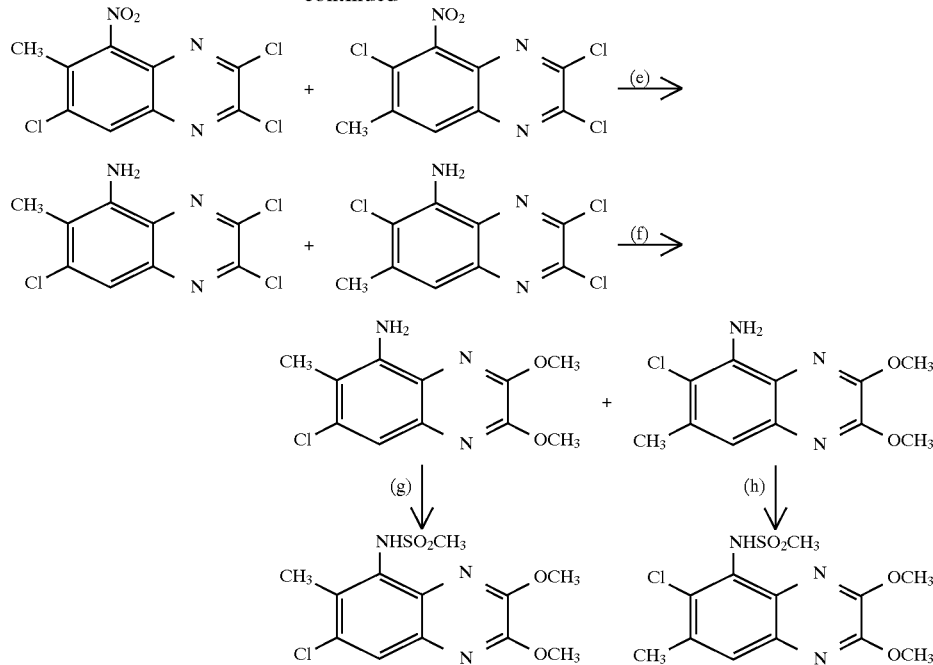

The following compounds listed below were obtained in an analogous manner to the 6-chloro-7-ethyl and 7-chloro-6-ethyl derivatives prepared in Preparation 13.

1,4-Dihydro-6-chloro-7-methylquinoxalin-2,3-dione was obtained from 1, 2-diamino-4-chloro-5-methylbenzene (supplied by Maybridge Chemicals) as a dark grey solid, m.p. >330° C.

Analysis %: Found; C,51.58; H,2.98; N,13.27; $C_9H_7ClN_2O_2$ requires C,51.32; H,3.35; N,13.30%.

1,4-Dihydro-6-chloro-7-methyl-5-nitroquinoxalin-2,3-dione and 1, 4-dihydro-7-chloro-6-methyl-5-nitroquinoxalin-2,3-dione were obtained as a yellow solid (1:2 ratio).

$^1$H NMR (300 MHz, CDCl$_3$) δ=2.23 (2H,s), 2.35 (1H,s), 7.19 (0.3H,s), 7.30 (0.7H,s), 11.9–12.25 (2H,br m).

2,3,7-Trichloro-6-methyl-5-nitroquinoxaline and 2,3,6-trichloro-7-methyl-5-nitro-quinoxaline were obtained as a straw-coloured powder, and could be separated with difficulty for characterisation purposes. Flash chromatography (gradient elution with hexane/dichloromethane) gave first the 6-methyl-7-chloro isomer as a white solid, m.p. 164°–165° C.

Analysis %: Found, C,36.76; H,1.37; N,14.43, $C_9H_4Cl_3N_3O_2$ requires: C,36.96; H,1.38; N,14.37%.

The second eluted isomer (7-methyl-6-chloro) was a straw-coloured solid, m.p. 121°–122° C.

Analysis %: Found, C,39.78; H,2.02; N,13.23; $C_9H_4Cl_3N_3O_2$. 0.22 hexane requires: C,39.80; H,2.29; N,13.49%.

5-Amino-2,3,7-trichloro-6-methylquinoxaline and 5-amino-2,3,6-trichloro-7-methylquinoxaline were obtained as a brown solid.

$^1$H NMR (300 MHz, CDCl$_3$) δ=2.41 (2H,s), 2.55 (1H,s), 5.03 (1.3H, br s), 5.08 (0.7H, br s), 7.23 (0.3H,s), 7.44 (0.7H,s).

5-Amino-7-chloro-2,3-dimethoxy-6-methylquinoxaline and 5-amino-6-chloro-2, 3-dimethoxy-7-methylquinoxaline were separated by repeated column chromatography on silica gel, eluting with hexane/ethyl acetate =1:1 followed by dichloromethane.

The first eluted compound, the 6-chloro-7-methyl isomer, was obtained as an off-white solid, m.p. 169°–170° C.

Analysis %: Found, C,53.80; H,5.16; N,16.18; $C_{11}H_{12}ClN_3O_2$. 0.15 hexane requires: C,53.61; H,5.33; N,15.76%.

The second eluted compound, the 7-chloro-6-methyl isomer, was obtained as an orange solid, m.p. 181°–182° C.

Analysis %: Found, C,52.55; H,4.72; N,16.61 $C_{11}H_{12}ClN_3O_2$. 0.05 hexane requires: C,52.61; H,4.96; N,16.29%.

N-(6-Chloro-2,3-dimethoxy-7-methylquinoxalin-5-yl) methanesulphonamide was obtained as a white solid m.p. 198° C.

$^1$H NMR (300 MHz,CDCl$_3$) δ=2.58, (3H,s), 3.38 (3H,s), 4.15 (3H,s), 4.18 (3H,s), 7.00 (1H,br s), 7.60 (1H,s).

m/z (thermospray) 332 (MH$^+$). ν$_{max.}$ (KBr) 3230, 2950, 1480 and 1150 cm$^{-1}$.

N-(7-Chloro-2,3-dimethoxy-7-methylquinoxalin-5-yl) methanesulphonamide was obtained as a white solid m.p. 228°–229° C.

Analysis %: Found, C,43.51; H,3.98; N,12.60 $C_{12}H_{14}ClN_3O_4S$ requires: C,43.44; H,4.25; N,12.60%.

PREPARATION 15

4-Hydroxymethyl-2-(triphenylmethyl)-1,2,3-triazole

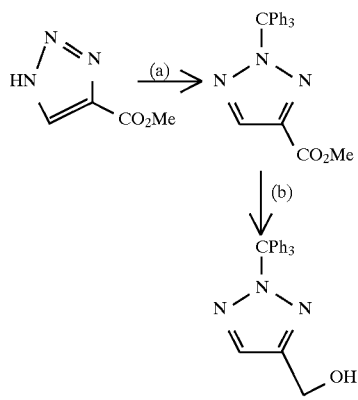

(a) Methyl 1 H-1,2,3-triazole-4-carboxylate [J Org Chem 41, 1041 (1976)] (1.00 g, 7.09 mmol) was added to a stirred suspension of sodium hydride (234 mg, 80% oil dispersion, 7.80 mmol) in anhydrous tetrahydrofuran (100 ml) under nitrogen at room temperature. After 20 minutes the mixture was cooled to 0° C. and trityl chloride (2.17 g, 7.80 mmol) was added. The mixture was stirred for 4 hours at 0° C. Water (100 ml) was added and the tetrahydrofuran was removed under reduced pressure. The remaining mixture was extracted with ethyl acetate (100 ml). The organic layer was dried ($MgSO_4$), filtered and concentrated under reduced pressure to afford a solid which was purified by flash chromatography on silica gel eluting with 5–30% ethyl acetate in hexane. The first eluted product was tentatively identified as methyl 1-(triphenylmethyl)-1, 2,3-triazole-4-carboxylate and was obtained as a white solid (600 mg, 21%).

$^1$H NMR (300 MHz, $CDCl_3$) δ=3.92 (3H,s), 7.11 (6H,m), 7.32 (9H,m), 8.15 (1H,s).

The second eluted product was tentatively identified as methyl 2-(triphenylmethyl)-1, 2,3-triazole-4-carboxylate and was obtained as a white solid (500 mg, 18%).

$^1$H NMR (300 MHz, $CDCl_3$) δ=3.94 (3H,s), 7.11 (6H,m), 7.36 (9H,m), 8.02 (1H,s).

(b) A solution of lithium aluminium hydride (1.04 ml, 1M in tetrahydrofuran, 1.04 mmol) was added dropwise to a stirred solution of methyl 2-(triphenylmethyl)-1, 2,3-triazole-4-carboxylate (from step (a), 500 mg, 1.38 mmol) in anhydrous tetrahydrofuran (30 ml) at 0° C. under nitrogen. The mixture was stirred for 1 hour at 0° C. and then water (2 ml), 15% aqueous sodium hydroxide (4 ml) and then more water (4 ml) were added. The resulting suspension was filtered through Arbocel filter aid and the filtrate was dried ($MgSO_4$) and concentrated under reduced pressure. The residue was partitioned between dichloromethane (150 ml) and water (150 ml). The dichloromethane layer was washed with water (600 ml) and then dried ($MgSO_4$) and concentrated under reduced pressure to leave the title compound as a white solid (401 mg, 85%).

$^1$H NMR (300 MHz, $CDCl_3$) δ=2.05 (1H,t,J7 Hz), 4.81 (2H,d,J7 Hz), 7.12 (6H,m), 7.35 (9H,m), 7.47 (1H,s).

PREPARATION 16

4-Hydroxymethyl-5-methyl-1 -(triphenylmethyl) imidazole

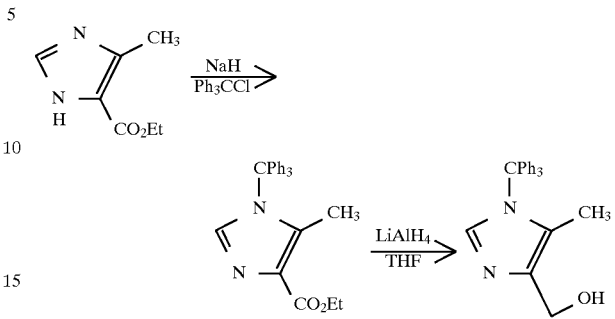

(a) Sodium hydride (900 mg, 80% oil dispersion, 30 mmol) was added in portions over 5 minutes to a stirred solution of ethyl 4-methyl-imidazole-5-carboxylate (3.85 g, 25 mmol) in dry tetrahydrofuran (100 ml) at room temperature under nitrogen. After 10 minutes, trityl chloride (8.36 g, 30 mmol) was added in one portion. After 1 h, the mixture was diluted with ethyl acetate (500 ml) and washed with water (200 ml). The washings were extracted with ethyl acetate (2×75 ml) and the combined organic solutions were dried ($MgSO_4$) and concentrated under reduced pressure. The residue was purified by flash chromatography (gradient elution with hexane/ethyl acetate to give ethyl 5-methyl-1-(triphenylmethyl)imidazole-4-carboxylate (1.01 g, 10%) as a white solid.

$^1$H NMR (300 MHz, $CDCl_3$) δ=1.38 (3H,t,J 6Hz), 1.83 (3H,s), 4.36 (2H,q,J 6 Hz), 7.14 (6H,m), 7.35 (10H,m).

(b) A solution of lithium aluminium hydride (7.65 ml, 1M in tetrahydrofuran, 7.65 mmol) was added dropwise to a stirred suspension of ethyl 5-methyl-1 -(triphenylmethyl) imidazole-4-carboxylate (1.01 g, 2.55 mmol) in anhydrous tetrahydrofuran (50 ml) under nitrogen at 0° C. over 1 minute. After 30 minutes, water (300 µl) was added cautiously, followed by aqueous sodium hydroxide (1M, 300 µl) and water (900 µl). The suspension was filtered using Arbocel filter aid and the filter cake was washed with tetrahydrofuran (2×30 ml). The filtrate was concentrated under reduced pressure, and the residue was dissolved in boiling methanol (50 ml). Dichloromethane (200 ml) and anhydrous magnesium sulphate were added, and the mixture was filtered through Arbocel filter aid. The filtrate was concentrated under reduced pressure to give a white solid (325 mg, 36%).

$^1$H NMR (300 MHz, $CDCl_3$) δ=1.47 (3H,s), 4.05 (2H,s), 7.14 (6H,m), 7.35 (10H,m).

PREPARATION 17

4-Hydroxymethyl-1 -(trilhenylmethyl)pyrazole

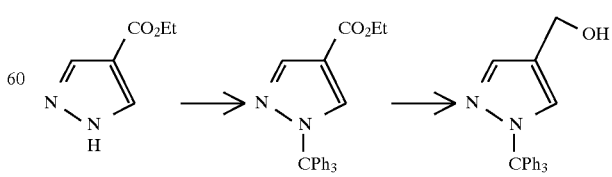

(a) Ethyl 1 H-pyrazole-4-carboxylate (1.50 g, 10.7 mmol) was added in portions to a stirred suspension of sodium hydride (353 mg, 80% oil dispersion, 11.8 mmol) in anhydrous tetrahydrofuran (100 ml) under nitrogen at room temperature. After 20 minutes, the mixture was cooled to 0° C. and trityl chloride (3.28 g, 11.8 mmol) was added. The mixture was stirred at 0° C. for 4 h and allowed to warm to room temperature overnight. The mixture was then heated at 50° C. for 3 h, cooled, and further portions of sodium hydride (321 mg, 10.7 mmol) and trityl chloride (1.0 g, 3.59 mmol) were added. The mixture was heated at 50° C. for 2 h, cooled, treated with water (50 ml) and concentrated under reduced pressure. The product was extracted into ethyl acetate (200 ml), the solution was dried (MgSO$_4$) and concentrated under reduced pressure. The residue was purified by flash chromatography (gradient elution with hexane/ethyl acetate) to give ethyl 1 -(triphenylmethyl)-pyrazole-4-carboxylate (2.273 g, 56%), as a white solid.

$^1$H NMR (300 MHz, CDCl$_3$) δ=1.31 (3H,t,J 7 Hz), 4.27 (2H,q, J 7 Hz), 7.13 (6H,m), 7.32 (9H,m), 7.94 (1H,s), 8.02 (1H,s).

(b) Lithium aluminium hydride (1M solution in tetrahydrofuran, 4.45 ml, 4.45 mmol) was added dropwise to a stirred solution of ethyl 1-(triphenylmethyl)-pyrazole-4-carboxylate (2.27 g, 5.93 mmol) in anhydrous tetrahydrofuran (300 ml) under nitrogen at 0° C. After 1 h, the mixture was treated sequentially with water (3 ml), 15% aqueous sodium hydroxide (3 ml) and water (6 ml). The mixture was filtered through Arbocel filter aid, the filtrate was dried (MgSO$_4$) and concentrated under reduced pressure, to give 4-hydroxymethyl-1-(triphenylmethyl) pyrazole (1.746g, 86%), as a white solid.

$^1$H NMR (300 MHz, CDCl$_3$) δ=1.43 (1H,brs), 4.35 (2H, s), 7.16 (6H,m), 7.26 (9H,m), 7.37 (1H,s), 7.68 (1H,s).

PREPARATION 18

3-Hydroxymethyl-1-(triphenylmethyl)-1,2,4-triazole

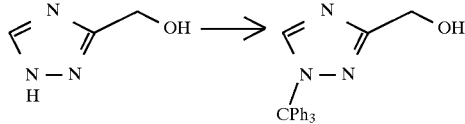

Triethylamine (1.13 ml, 8.08 mmol) was added to a suspension of 3-hydroxymethyl-1 H- 1, 2,4-triazole [J Am Chem Soc, 77, 1538 (1955)], (400 mg, 4.04 mmol) in dry dichloromethane (8 ml) at 0° C. A solution of trityl chloride (1.24 g, 4.44 mmol) in anhydrous tetrahydrofuran was added, and the mixture was stirred at room temperature for 3 h. The mixture was partitioned between water (75 ml) and dichloromethane (75 ml). The organic layer was dried (MgSO$_4$) and concentrated under reduced pressure to give the title compound (1.547 g, >100%) which was used without purification.

$^1$H NMR (300 MHz, CDCl$_3$) δ=4.77 (2H,s), 7.13 (6H,m), 7.32 (9H,m), 7.95 (1 H,s).

PREPARATION 19

3-(Hydroxymethyl)-1 -(triphenylmethyl)pyrazole

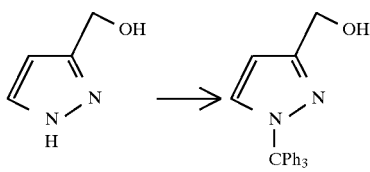

This compound was prepared from 3-(hydroxymethyl)-1 H-pyrazole, [J. Am. Chem. Soc, 71, 3996, (1949)], trityl chloride and trimethylamine using the method of Preparation 18, above. The crude product was purified by flash chromatography (gradient elution with hexane/ethyl acetate) to give a white solid (1.428 g, 60%).

$^1$H NMR (300 MHz, CDCl$_3$) δ=1.14 (1 H,t,J 5 Hz), 4.67 (2H,dd,J 2 and 5 Hz), 6.22 (1H,d,J 2 Hz), 7.16 (6H,m), 7.30 (10H,m).

m/z (thermospray) 341 (MH$^+$).

PREPARATION 20

N-(3-Amino-6-chloro-7-trifluoromethyl-2-methoxyquinoxalin-5-yl)methanesulphonamide

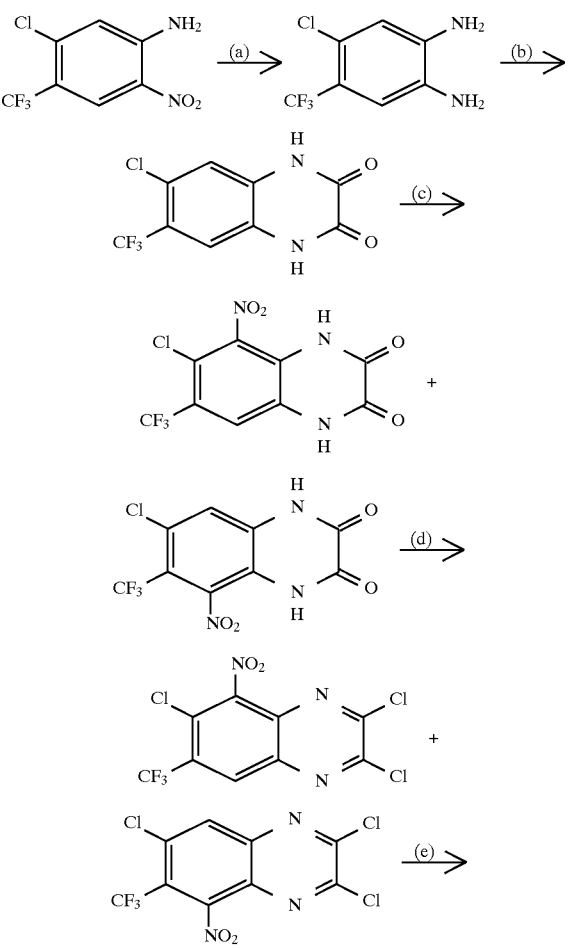

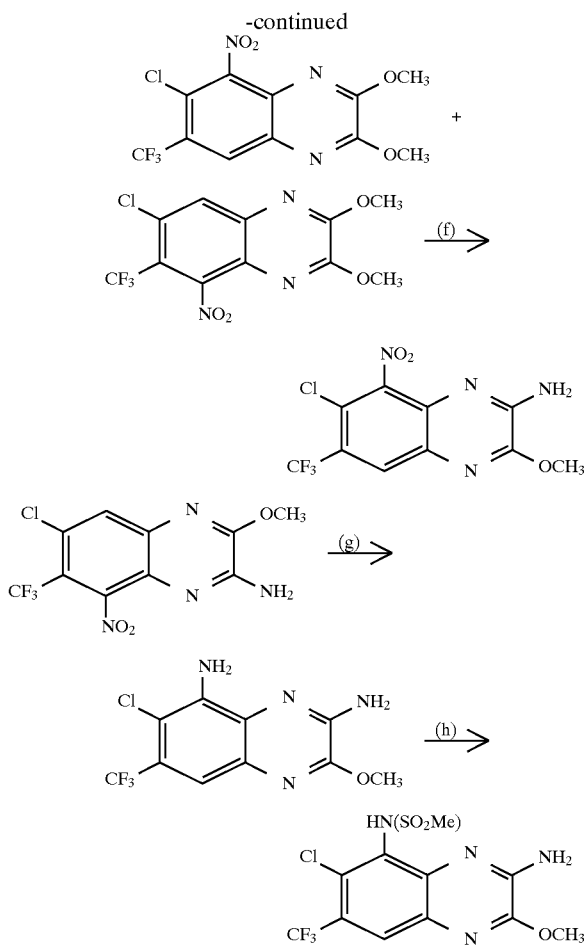

(a) 1,2-Diamino-4-chloro-5-trifluoromethyl benzene

A solution of sodium dithionite (51.0 g, 293 mmol) in water (700 ml) was added to a stirred mixture of 5-chloro-4-trifluoromethyl-2-nitroaniline [Khim Geterotsikl Soedin, 1136 (1976)] (23.5 g, 97.7 mmol) and potassium bicarbonate (51.0 g) in methanol (700 ml) at room temperature. After 30 minutes, the mixture was concentrated under reduced pressure, and the residue was partitioned between dichloromethane and water. The combined organic extracts were dried (MgSO$_4$) and concentrated under reduced pressure to give an orange solid (13.3 g, 65%).

$^1$H NMR (300 MHz, CDCl$_3$) δ=3.37 (2H, br s), 3.70 (2H, br s), 6.78 (1H,s), 6.98 (1H,s).

(b) 1,4-Dihydro-6-chloro-7-trifluoromethylquinoxalin-2,3-dione

A mixture of 1,2-diamino-4-chloro-5-trifluoromethylbenzene (13.4 g, 63.6 mmol) and diethyl oxalate (100 ml) was heated at reflux under nitrogen with stirring for 5 h. After being cooled, the solid which formed was filtered off and washed well with ether to afford a pale orange solid (14.5 g, 86%).

Analysis%: Found, C,40.93; H,1.35; N,10.43: C$_9$H$_4$ClF$_3$N$_2$O$_2$ requires: C,40.85; H,1.52; N,10.59%.

(c) 1,4-Dihydro-6-chloro-7-trifluoromethyl-5-nitroquinoxalin-2,3-dione and 1,4-dihydro-7-chloro-6-trifluoromethyl-5-nitroquinoxalin-2,3-dione 1,4-Dihydro-6-chloro-7-trifluoromethylquinoxalin-2,3-dione (from step (b), 14.06 g, 53.1 mmol) was added in portions to stirred fuming nitric acid (100 ml) at 0° C. The mixture was allowed to warm to 20° C. over 30 minutes after the addition was complete, and the resulting solution was poured onto iced water and the solid which precipitated was filtered off, washed with water, and dried to afford a pale orange solid (15.06 g, 92%), as a 2:1 mixture of isomers.

$^1$H NMR (300 MHz, DMSO-d$_6$) δ=7.42 (1 H minor,s), 7.62 (1H major,s), 12.33 (1H major, 1H minor,br s), 12.51 (1H major, 1H minor,br s).

(d) 2,3,6-Trichloro-7-trifluoromethyl-5-nitroquinoxaline and 2, 3,7-trichloro-6-trifluoromethyl-5-nitroquinoxaline A mixture of the quinoxalindiones from (c) above, (14.7 g, 47.5 mmol) thionyl chloride (140 ml) and dry dimethylformamide (1.4 ml) was heated at reflux for 30 minutes, cooled and added dropwise to iced water. The solid which formed was extracted into ethyl acetate and the solution was washed with one portion of saturated aqueous sodium bicarbonate, and two portions of water. The solution was dried (MgSO$_4$) and concentrated under reduced pressure to give a yellow oil (17.9 g, 100%).

$^1$H NMR (300 MHz, CDCl$_3$) δ=8.33 (1H minor,s), 8.58 (1H major,s).

(e) 6-Chloro-7-trifluoromethyl-2,3-dimethoxy-5-nitroquinoxaline and 7-chloro-6-trifluoromethyl-2,3-dimethoxy-5-nitroquinoxaline Sodium hydride (0.95 g, 80% oil dispersion, 31.7 mmol) was added in portions to a stirred solution of a mixture of the trichloroquinoxalines from (d) above (5.0 g, 14.4 mmol) in anhydrous methanol (125 ml) at room temperature. After 18 h, the mixture was concentrated under reduced pressure, diluted with water and the resulting solid was filtered off, washed with water, and dried, to afford a white solid (4.4 g, 90%), as a 2:1 mixture of isomers.

$^1$H NMR (300 MHz, CDCl$_3$) δ=4.10 (3H minor,s), 4.15 (3H major,s), 4.20 (3H major, 3H minor,s), 8.00 (1H minor, s), 8.25 (1H major,s).

(f) 3-Amino-6-chloro-7-trifluoromethyl-2-methoxy-5-nitroquinoxaline and 3-amino-7-chloro-6-trifluoromethyl-2-methoxy-5-nitroquinoxaline A mixture of the dimethoxyquinoxaline isomers from (e) above (0.5 g, 1.5 mmol) and saturated methanolic ammonia (7 ml) was heated at 100° C. in a closed pressure vessel for 4 h. The mixture was cooled, poured into water and extracted with three portions of ethyl acetate. The combined extracts were dried (MgSO$_4$) and concentrated under reduced pressure. The reaction was repeated on the same scale, and the crude products were combined and purified by flash chromatography (eluting with hexane/ethyl acetate =3:1). The first eluted compound was the 6-chloro-7-trifluoromethyl isomer, (590mg, 61%) obtained as an off-white solid.

hu 1H NMR (300 MHz, CDCl$_3$) δ=4.08 (3H,s), 7.88 (1H,br s), 8.08 (1H,s), 18.43 (1H,br.,s).

The second eluted compound was the 7-chloro-6-trifluoromethyl isomer (205 mg, 21%), obtained as an off-white solid.

$^1$H NMR (300 MHz, CDCl$_3$) δ=4.12 (3H,s), 5.65 (2H, br.,s) 7.80 (1 H,s).

(g) 3,5-Diamino-6-chloro-7-trifluoromethyl-2-methoxyquinoxalin

Hydrazine hydrate (0.34 ml, 7.0 mmol) was added to a stirred solution of 3-amino-6-chloro-7-trifluoromethyl-2-methoxy-5-nitroquinoxaline (0.55g, 1.7 mmol) in ethanol (25 ml) containing suspended 10% ruthenium-on-carbon (55 mg) under nitrogen at reflux. After 20 minutes, additional hydrazine hydrate (0.17 ml, 3.4 mmol) was added, and the mixture was stirred at reflux for 30 minutes, then allowed to stand at room temperature overnight. The mixture was filtered through Arbocel filter aid, and the filter cake was washed with ethanol and dichloromethane. The filtrate was concentrated under reduced pressure to give the title compound (0.50 g, 100%) as an off-white solid.

$^1$H NMR (300 MHz, CDCl$_3$) δ=4.13 (3H,s), 5.08 (2H,br s), 5.30 (2H,br s), 7.47 (1H,s).

(h) N-(3-Amino-6-chloro-7-trifluoromethyl-2-methoxyquinoxalin-5-yl)methanesulphonamide Methanesulphonic anhydride (2.9 g, 16.6 mmol) was added to a stirred solution of 3,5-diamino-6-chloro-2-methoxy-7-trifluoromethylquinoxaline (0.48 g, 1.64 mmol) and pyridine (1.34 ml, 16.6 mmol) in anhydrous tetrahydrofuran under nitrogen at room temperature. After 18 h, the mixture was concentrated under reduced pressure, diluted with water, and the products extracted into ethyl acetate (three portions). The combined organic solutions were washed with 2M hydrochloric acid, saturated aqueous sodium bicarbonate and saturated aqueous sodium chloride, dried (MgSO$_4$) and concentrated under reduced pressure to give a yellow solid (0.9 g). This material was suspended in a 25% solution of ethylamine in ethanol (20 ml) at 50° C. for 2 h. The mixture was concentrated under reduced pressure, and partitioned between ethyl acetate and 2M hydrochloric acid. The extracts were dried (MgSO$_4$) and concentrated under reduced pressure. The residue was purified by flash chromatography (eluting with dichloromethane, then dichloromethane/ methanol =99:1 and finally dichloromethane/ methanol =98:2). Fractions containing the product were concentrated under reduced pressure, dissolved in ethyl acetate and extracted with 2M hydrochloric acid. The acid solution was rendered basic (pH8) by the addition of saturated aqueous sodium bicarbonate, and the product was extracted into ethyl acetate. The organic solution was dried (MgSO$_4$) and concentrated to give the title compound (0.25 g, 41%), as a white solid.

$^1$H NMR (300 MHz, DMSO-d$_6$) δ=3.29 (3H,s), 4.07 (3H,s), 7.70 (2H,br s), 7.90 (1H,s), 9.35 (1H,s).

m/z (thermospray) 371 (MH$^+$).

PREPARATION 21

N-(6,7-Dichloro-2,3-dimethoxyquinoxalin-5-yl)-N-(methoxycarbonylmethyl)-methanesulphonamide

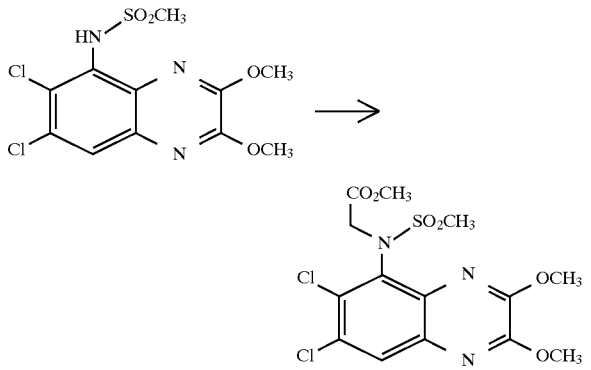

Anhydrous potassium carbonate (1.60 g, 11.2 mmol) was added to a suspension of N-(6,7-dichloro-2,3-dimethoxyquinoxalin-5-yl)-methanesulphonamide (see Preparation 3, 3.0 g, 9.4 mmol) in acetone (70 ml) with stirring. The mixture was heated at reflux for 15 minutes, cooled, and methyl bromoacetate (1.8 ml, 18.7 mmol) was added. The mixture was then heated at reflux for 2 h, cooled, diluted with ethyl acetate (300 ml) and washed with water (2×100 ml). The organic phase was dried (MgSO$_4$) and concentrated under reduced pressure. The residue was purified by flash chromatography (gradient elution with hexane/ ethyl acetate) to give the title compound as a white solid (3.177 g, 80%).

$^1$H NMR (300 MHz, CDCl$_3$) δ=3.44 (3H,s), 3.71 (3H,s), 4.14 (3H,s), 4.20 (3H,s), 4.37 (1H,d,J 18 Hz), 4.71 (1H,d,J 18 Hz), 7.95 (1H,s) m/z (thermospray) 424 (MH$^+$).

PREPARATION 22

N-(6,7-Dichloro-2,3-dimethoxyquinoxalin-5-yl)-N-F (6-methoxypyridin-2-yl) methyl-methanesulphonamide

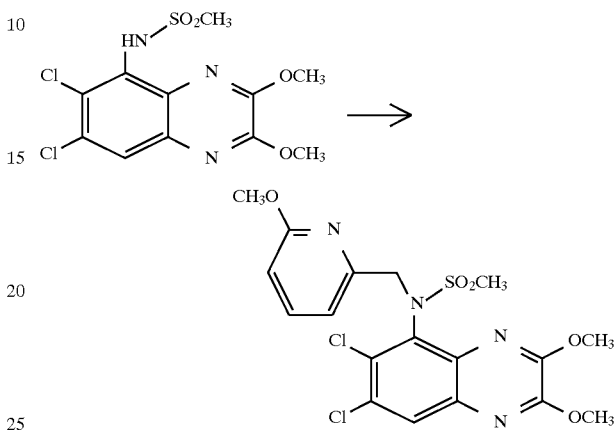

This compound was prepared by the method of Preparation 21, above, using 2-(bromomethyl)-6-methoxypyridine [(see Synth Commun, 24, 1367 (1994)] in place of methyl bromoacetate. The compound was obtained as a white solid (299 mg, 84%).

$^1$H NMR (300 MHz, CDCl$_3$) δ=3.38 (3H,s), 3.68 (3H,s), 4.07 (3H,s), 4.15 (3H,s), 4.85 (1H,d,J 14 Hz), 4.99 (1H,d,J 14 Hz), 6.58 (1H,d,J 8 Hz), 6.73 (1H,d,J 7 Hz), 7.40 (1H,dd,J 8 and 7 Hz), 7.92 (1H,s). m/z (thermospray) 473 (MH$^+$).

PREPARATION 23

N-(6,7-Dichloro-2,3-dimethoxyquinoxalin-5-yl)-N-(1-methoxycarbonylethyl)-methanesulphonamide

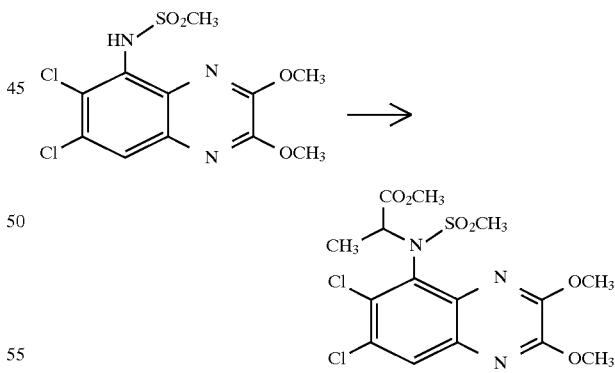

The compound was prepared by the method of Preparation 21, above, using methyl 2-bromopropanoate in place of methyl bromoacetate. The product was obtained as a mixture of two diastereomers, which were separable by flash chromatography (gradient elution with hexane/ethyl acetate). The first isomer was obtained as a white solid, (1.456 g, 57%) (Rf. 0.63, hexane/ethyl acetate =1:1).

$^1$H NMR (300 MHz, CDCl$_3$) δ=1.11 (3H,d,J 7 Hz), 3.36 (3H,s), 3.82 (3H,s), 4.15 (3H,s), 4.18 (3H,s), 5.10 (1H,q,J 7 Hz), 7.96 (1H,s).

m/z (thermospray) 438 (MH⁺).

The second isomer was also obtained as a white solid (0.75 g, 29%) (Rf 0.45, hexane/ethyl acetate =1:1).

¹H NMR (300 MHz, CDCl₃) δ=1.26 (3H,d,J 7 Hz), 3.36 (3H,s), 3.61 (3H,s), 4.15 (3H,s), 4.21 (3H,s), 4.98 (1H,q,J 7 Hz), 7.97 (1H,s).

m/z (thermospray) 438 (MH⁺).

PREPARATION 24

5-Amino-7-chloro-6-fluoro-2,3-dimethoxyquinoxaline and 5-amino-6-chloro-7-fluoro-2, 3-dimethoxyquinoxaline mixture of 2,3,6-trichloro-7-fluoro-5-nitroquinoxaline and 2,3,7-trichloro-6-fluoro-5-nitroquinoxaline. The mixture of products was obtained as a pale yellow solid (92% yield).

¹H NMR (300 MHz, CDCl₃) δ=7.90 (1H major, d,J 10 Hz), 8.28 (1H minor, d,J 8 Hz).

(c) The mixture of intermediates from (b) above was converted into a 6:1 mixture of 5-amino-2,3,6-trichloro-7-fluoroquinoxaline and 5-amino-2, 3,7-trichloro-6-fluoroquinoxaline by the method of Preparation 1(b). The mixture of products was obtained as a yellow solid (100% yield).

¹H NMR (300 MHz, CDCl₃) δ=4.92 (2H minor, br s), 5.45 (2H major, br s), 7.08 (1H major, d,J 10 Hz), 7.38 (1H minor d, J 8 Hz). m/z (thermospray) 267 (MH⁺).

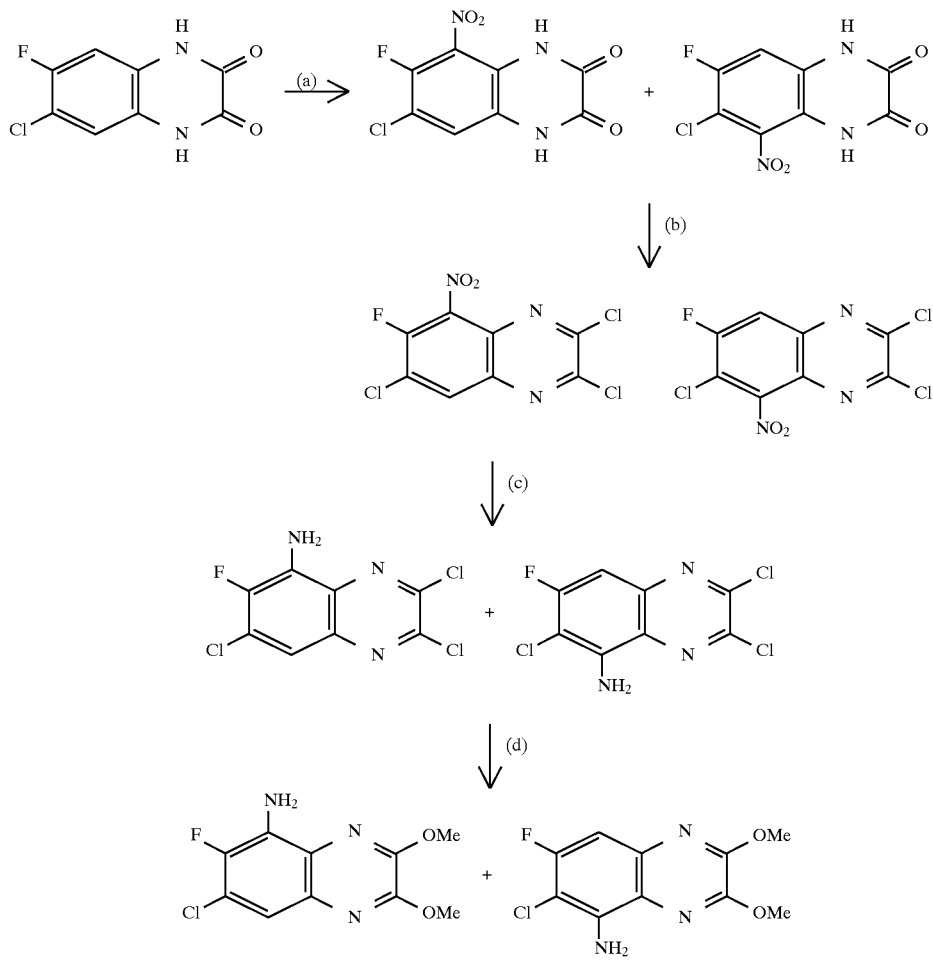

(a) 1,4-Dihydro-6-chloro-7-fluoroquinoxalin-2,3-dione (see Example 17, WO94/00124) (0.200 g, 0.93 mmol) was added in portions to fuming nitric acid (density, 1.5 g.cm⁻³, 5 ml) at room temperature. After 30 minutes, the mixture was added to water (50 ml). The resulting solid was filtered off and dried in vacuo to give a 6:1 mixture of 1,4-dihydro-6-chloro-7-fluoro-5-nitroquinoxalin-2, 3-dione and 1,4-dihydro-7-chloro-6-fluoro-5-nitroquinoxalin-2, 3-dione (0.095 g, 39%) as a pale orange solid.

¹H NMR (300 MHz, DMSO-d₆) δ=7.24 (1H major, d,J 10 Hz), 7.39 (1H minor, d,J 8Hz), 12.17 (1H major, 1H minor. br s), 12.29 (1H major, 1H minor, br s).

m/z (thermospray) 277, 279 (MNH₄⁺).

(b) The mixture of intermediates from (a) above was converted by the method of Preparation 1(a) into a 6:1

(d) The mixture of intermediates from (c) above was converted into a mixture of 5-amino-6-chloro-7-fluoro-2,3-dimethoxyquinoxaline and 5-amino-7-chloro-6-fluoro-2,3-dimethoxyquinoxaline by the method of Preparation 1(c). The mixture of products was separated by flash chromatography (elution with toluene) to afford 5-amino-6-chloro-7-fluoro-2, 3-dimethoxyquinoxaline as a white solid (27% yield), m.p. 199°–200° C.

¹H NMR (300 MHz, CDCl₃) δ=4.15 (6H,s), 5.04 (2H,br s), 6.90 (1H,d,J 10 Hz).

m/z (thermospray) 258,260 (MH⁺).

5-Amino-7-chloro-6fluoro-2,3-dimethoxyquinoxaline was obtained as a white solid (6% yield), m.p. 198°–199° C.

$^1$H NMR (300 MHz, CDCl$_3$) δ=4.14 (3H,s), 4.18 (3H,s), 4.62 (2H,br s), 7.40 (1H,d,J 8 Hz).

m/z (thermospray): 258,260 (MH$^+$)

PREPARATION 25

N-(7-Chloro-6fluoro-2,3-dimethoxyquinoxalin-5-yl-methanesulphonamide

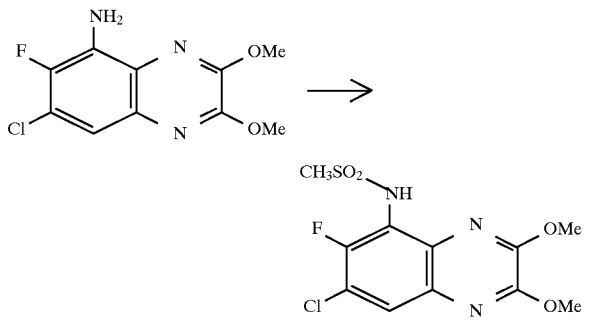

Methanesulphonic anhydride (0.55 g, 3.16 mmol) and pyridine (255 μl, 3.15 mmol) were added to a stirred suspension of 5-amino-7-chloro-6-fluoro-2,3-dimethoxyquinoxaline (see Preparation 24) (0.274 g, 1.06 mmol) in dichloromethane (15 ml) at room temperature under nitrogen. The mixture was stirred at room temperature overnight, concentrated to dryness and suspended in tetrahydrofuran (30 ml). The reaction mixture was treated with 1M sodium hydroxide (5.3 ml, 5.3 mmol) with ice-cooling, followed by stirring at 5° C. for 1.5 h. The reaction mixture was acidified to pH2 with 2M hydrochloric acid, concentrated and partitioned between water and dichloromethane. The layers were separated and the aqueous layer was extracted with dichloromethane twice. The combined organics were dried (MgSO$_4$) and concentrated to give a pale yellow solid. Suspension in THF (30 ml) and treatment with 1M sodium hydroxide (5.3 ml, 5.3 mmol) at 5° C. was followed by stirring at room temperature for 2 h. The reaction mixture was acidified to pH2 with 2M hydrochloric acid, concentrated to a small volume, diluted with water and filtered. The filtrate was washed with water and cold diethyl ether to afford a white solid (0.32 g, 90%), m.p. 227°–228° C.

$^1$H NMR (300 MHz, DMSO-d$_6$) δ=3.12 (3H,s), 4.04 (3H,s), 4.12 (3H,s), 7.90 (1H,d,J 8 Hz), 9.50 (1H,s). m/z (thermospray) 336, 338 (MH$^+$).

PREPARATION 26

N-(6-Chloro-7-fluoro-2,3-dimethoxyquinoxalin-5-yl)methanesulphonamide

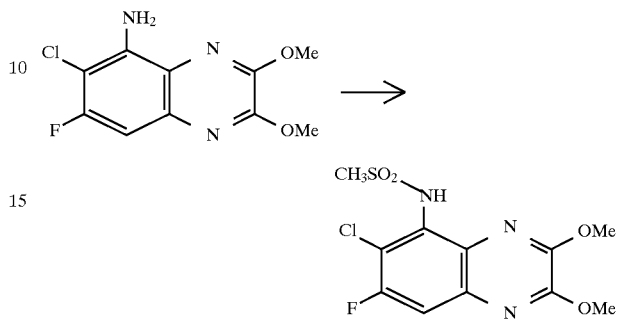

5-Amino-6-chloro-7-fluoro-2,3-dimethoxyquinoxaline (see Preparation 24) was converted by the method of Preparation 25 into N-(6-Chloro-7-fluoro-2,3-dimethoxyquinoxalin-5-yl)methanesulphonamide. The product was obtained as a white solid (30% yield).

$^1$H NMR (300 MHz, DMSO-d$_6$) δ=3.16 (3H,s), 4.04 (3H,s), 4.12 (3H,s), 7.72 (1H,d,J 10 Hz), 9.60 (1H,s).

m/z (thermospray) 336, 338 (MH$^+$).

PREPARATION 27

N-(6,7-Dichloro-2,3-dimethoxyquinoxalin-5-yl)-N-(2-aminoethyl) methanesulphonamide

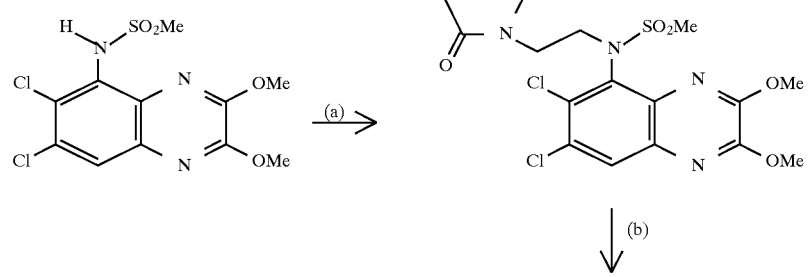

-continued

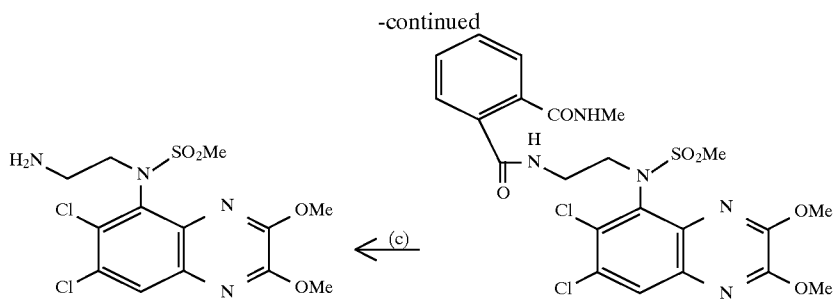

(a) N-(2-bromoethyl)phthalimide (1.73 g, 6.81 mmol) was added to a refluxing mixture of N-(6,7-dichloro-2,3-dimethoxy-quinoxalin-5-yl)-methanesulphonamide (Preparation 3, 2.00 g, 5.68 mmol) and potassium carbonate (1.88 g, 13.63 mmol) in acetone (100 ml) under nitrogen. After 48 hours, further N-(2-bromoethyl)phthalimide (1.73 g, 6.81 mmol) was added and refluxing continued for 18 hours. After cooling the mixture was concentrated under reduced pressure and the residue dissolved in dichloromethane. The resulting solution was washed twice with 1N sodium hydroxide solution, water and brine and then dried (MgSO$_4$) and concentrated under reduced pressure. The residue was purified by flash chromatography (eluting with hexane:ethyl acetate) to afford N-(6,7-dichloro-2,3-dimethoxyquinoxalin-5-yl)-N-(2-phthalimidoethyl) methanesulphonamide as a pale yellow solid (2.55g, 85%).

$^1$H NMR (300 MHz, CDCl$_3$) δ=3.25 (3H,s), 3.64 (2H,t,J 8 Hz), 3.90–4.02 (2H,m), 4.12 (3H,s), 4.17 (3H,s), 7.65–7.80 (3H,m), 7.82–7.92 (2H,m). m/z (thermospray) 525 (MH$^+$).

(b) A 33% solution of methylamine in IMS (industrial methylated spirits) (1.77 ml, 19.03 mmol) was added to a stirred solution of N-(6,7-dichloro-2,3-dimethoxyquinoxalin-5-yl)-N-(2-phthalimidoethyl) methanesulphonamide (2.00 g, 3.81 mmol) in dichloromethane (38 ml) in a nitrogen filled flask equipped with a rubber septum. The mixture was stirred for 72 hours and then further 33% methylamine in IMS solution (1.77 ml, 19.03 mmol) was added. The mixture was stirred for 18 h and then concentrated under reduced pressure. The residue was dissolved in dichloromethane and extracted twice with 10% aqueous citric acid. The organic layer was concentrated under reduced pressure to afford N-(6,7-dichloro-2,3-dimethoxyquinoxalin-5-yl)-N-(N'-([2-methylaminocarbonyl]benzoyl) aminoethyl) methanesulphonamide as a solid (996 mg, 49%).

$^1$H NMR (300 MHz, CDCl$_3$) δ=2.92 (3H,d,J5 Hz), 3.20 (3H,s), 3.45–3.62 (2H,m), 3.97 (3H,s), 3.98–4.10 (2H,m), 4.13 (3H,s), 6.60 (1H,br d), 7.44 (1H,m), 7.60 (1H,m), 7.72 (1H,m), 7.83 (1H,m), 7.95 (1H,s).

m/z (thermospray) 556 (MH$^+$).

(c) Hydrazine hydrate (26 μl, 26 mg, 0.531 mmol) was added dropwise to a solution of N-(6,7-dichloro-2,3-dimethyoxyquinoxalin-5-yl)-N-(N'-([2-methylaminocarbonyl]benzoyl)aminoethyl) methanesulphonamide (283 mg, 0.531 mmol) in dichloromethane (5 ml) and the mixture was refluxed for 4 h. Methanol (1 ml) was added and refluxing continued for 18 h. After cooling the mixture was concentrated under reduced pressure. The residue was dissolved in ethyl acetate and extracted with 10% citric acid. The aqueous layer was adjusted to pH8 with solid potassium carbonate and extracted twice with dichloromethane. The combined organic layers were dried (MgSO$_4$) and concentrated under reduced pressure to give N-(6,7-dichloro-2,3-dimethoxyquinoxalin-5-yl)-N-(2-aminoethyl) methanesulphonamide as a pale yellow solid (138 mg, 66%).

$^1$H NMR (300 MHz, CDCl$_3$) δ=2.70–2.88 (2H,m), 3.11 (3H,s), 3.79 (2H,t,J 8 Hz), 4.17 (3H,s), 4.20 (3H,s), 7.95 (1H,s). m/z (thermospray) 395 (MH$^+$).

PREPARATION 28

5-Bromomethyl-6,7-dichloro-2,3-dimethoxyquinoxaline

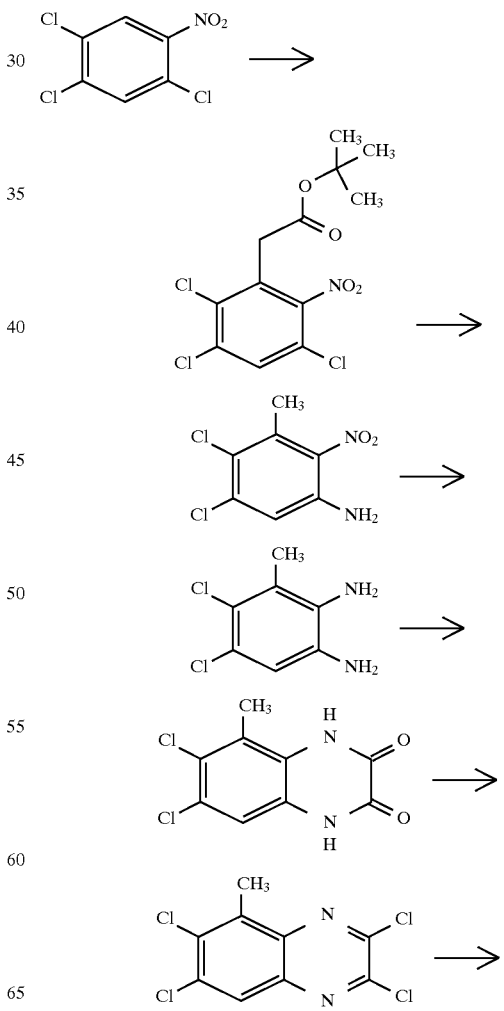

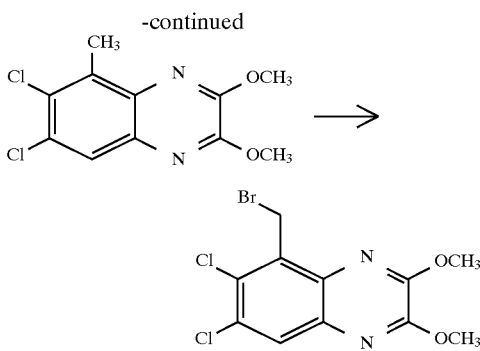

(a) A solution of 2,4,5-trichloronitrobenzene (Jpn. Kokai Tokyo Koho JP 81,169,651 (1980), Chem. Abstr. 1981,96, 162307 q)(103 g, 0.46 mol) and t-butyl chloroacetate (79 ml, 0.55 mol) in dry tetrahydrofuran (400 ml) was added dropwise over 30 minutes to a solution of potassium t-butoxide (128 g, 1.14 mol) in dry tetrahydrofuran (800 ml) with stirring, under nitrogen keeping the temperature at −40° C. After the addition was complete, the resulting dark blue solution was stirred for a further 30 minutes. The mixture was poured into 0.5M hydrochloric acid (2 L) and the product was extracted into ethyl acetate (2.5L and 1 L). The combined organic solutions were dried ($MgSO_4$) and evaporated onto silica gel (70–200 m, 200 g). The silica gel was applied to the top of a silica gel chromatography column (800 g), and the product was eluted using a hexane/ethyl acetate gradient. Product-containing fractions were combined and evaporated to give a yellow solid, which was triturated with hexane to give t-butyl 2-nitro-3,5,6-trichlorophenylacetate (91.8 g, 59%) as a white solid.

Found C, 42.32; H, 3.50; N, 4.03 $C_{12}H_{12}Cl_3NO_4$ requires C,42.32; H, 3.55; N, 4.11%.

$^1$H NMR (300 MHz, $CDCl_3$) δ=1.42 (9H,s), 3.73 (2H,s), 7.60 (1H,s) m/z (thermospray) 357 ($MNH_4^+$).

(b) A mixture of t-butyl 2-nitro-3,5,6-trichlorophenylacetate (from step (a), 123 g, 0.361 mol), and saturated aqueous ammonia (300ml) in 2-methoxy ethanol (360 ml) was heated in an autoclave at 150° C. for 72 h. The resulting viscous, black mixture was diluted with water (1 L) and ethyl acetate (1 L) and filtered through Arbocel filter aid. The dark red filtrate was separated, and the aqueous layer extracted with ethyl acetate (2×1 L). The combined organic solutions were washed with brine (1 L), dried ($MgSO_4$) and evaporated onto silica gel (70–200 m, 200 g). The silica gel was applied to the top of the chromatography column containing silica gel (40–60 m, 800 g). Elution with hexane/ethyl acetate (98:2–92:8) gave 3-amino-5,6-dichloro-2-nitrotoluene (Eur. Pat. 385,850) as a bright orange solid (39.7 g), which was contaminated with 5-amino-3,6-dichloro-2-nitrotoluene (14%). This mixture was carried onto the next step without further purification.

$^1$H NMR (300 MHz, $CDCl_3$) δ=2.48 (3H,s), 4.80 (2H,s), 6.82 (1H,s).

(c) A solution of sodium dithionite (94 g, 0.54 mol) in water (1 L) was added to a stirred mixture of 3-amino-5,6-dichloro-2-nitrotoluene (from step (b), 39.7 g, 0.18 mol) and potassium bicarbonate (94 g, 0.94 mmol) in methanol (1 L) at room temperature. After 30 minutes, the mixture was concentrated under reduced pressure and the resulting suspension extracted with ethyl acetate (total of 700mi). The extracts were dried ($MgSO_4$) and concentrated under reduced pressure to give 2,3-diamino-5,6-dichlorotoluene (26.1 g, 38% over 2 steps) as a brown solid.

$^1$H NMR (300 MHz, $CDCl_3$) δ=2.28 (3H,s), 3.36 (2H,br s), 3.42 (2H,br s), 6.72 (1H,s).

(d) A mixture of 2,3-diamino-5,6-dichlorotoluene (from step (c), 21.6 g, 0.137 mol) and oxalic acid (18.45 g, 0.206 mol) in hydrochloric acid (4M, 900 ml) was heated at reflux for 6 hours, cooled and filtered. The dark brown solid was suspended in diethyl ether, filtered and washed with more ether to give 6,7-dichloro-5-methyl-quinoxalin-2,3-dione (22.06 g, 66%).

$^1$H NMR (300 MHz, DMSO) δ=2.40 (3H,s), 7.14 (1H,s), 11.37 (1H,s), 11.94 (1H,s).

(e) A mixture of 6,7-dichloro-5-methylquinoxalin-2,3-dione (from step (d) 22.06 g, 90 mmol), thionyl chloride (300 ml) and dimethylformamide (1 ml) was heated at reflux for 3 hours, cooled and poured slowly into iced water. The resulting dark yellow precipitate was filtered off to give 5-methyl-2,3, 6,7-tetrachloroquinoxaline (24.42 g, 96%).

$^1$H NMR (300 MHz, $CDCl_3$) δ=2.85 (3H,s), 8.02 (1 H,s).

(f) A solution of sodium methoxide (38 ml, 25% solution in methanol, 175 mmol) was added over 10 minutes to a solution of 5-methyl-2,3,6,7-tetrachloroquinoxaline (from step (e), 21 g, 74 mmol) in dry tetrahydrofuran (200 ml) at 20° C. There was a mildly exothermic reaction followed by formation of a precipitate. After 1 h the mixture was diluted with ethyl acetate (3 L), washed with water (1 L), dried ($MgSO_4$) and concentrated under reduced pressure to give 6,7-dichloro-2,3-dimethoxy-5-methylquinoxaline (20.3 g, 100%).

$^1$H NMR (300 MHz, $CDCl_3$) δ=2.75 (3H,s), 4.15 (3H,s), 4.18 (3H,s), 7.78 (1H,s).

m/z (thermospray) 273 ($MH^+$).

(g) A mixture of 6,7-dichloro-2,3-dimethoxy-5-methylquinoxaline (from step (f), 22.0 g, 80.5 mmol), N-bromosuccinimide (17.2 g, 96.6 mmol) and α,α-azoisobutyronitrile (1.3 g, 8.0 mmol) was heated at reflux in 1,1,1-trichloroethane (400 ml) for 4 h under irradiation from a 500 W sunlamp. The mixture was cooled, silica gel (50 g, 60–230 m) was added, and the solvent was removed under reduced pressure. The residue was applied to the top of a silica gel chromatography column, and the product was eluted using a hexane/ethyl acetate gradient. The product was triturated with hexane to give 5-bromomethyl-6,7-dichloro-2,3-dimethoxyquinoxaline (25.3 g, 87%) as a fluffy white solid. Found: C, 37.72; H, 2.40; N, 7.40; $C_{11}H_9BrCl_2N_2O_2$ requires C,37.53; H, 2.58; N, 7.96%.

$^1$H NMR (300 MHz, $CDCl_3$) δ=4.15 (3H,s), 4.22 (3H,s), 5.20 (2H,s), 7.89 (1H,s).

PREPARATION 29

(6,7-Dichloro-2,3-dimethoxyquinoxalin-5-yl)methyl methyl sulphone

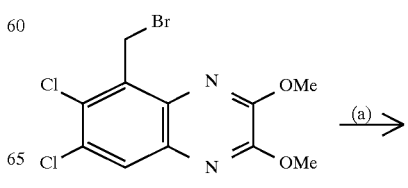

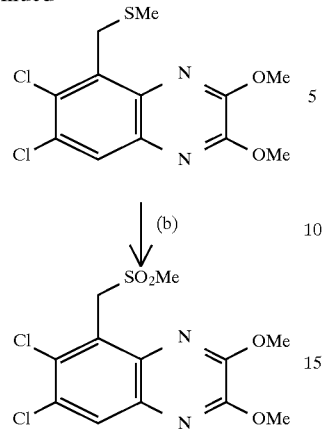

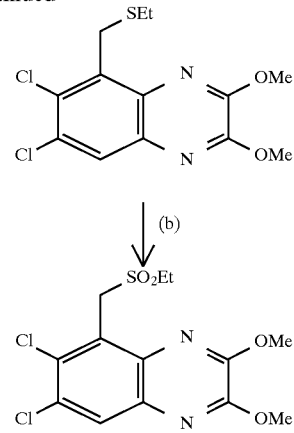

(a) Sodium methanethiolate (22 mg, 0.312 mmol) was added to a stirred solution of 5-bromomethyl-6,7-dichloro-2,3-dimethoxyquinoxaline (see Preparation 28) (100 mg, 0.284 mmol) in dry dimethylformamide (5 ml) under nitrogen at room temperature. The mixture was stirred for 10 minutes and was then quenched with brine and extracted twice with dichloromethane. The combined extracts were dried (MgSO$_4$) and concentrated under reduced pressure. The residue was purified by flash chromatography (eluting with 1:1 hexane:dichloromethane) to give 6,7-dichloro-2,3-dimethoxy-5-methylthiomethylquinoxaline (79 mg, 87%) as a white solid, m.p. 143°–5° C.

$^1$H NMR (300 MHz, CDCl$_3$) δ=2.10 (3H,s), 4.12 (3H,s), 4.15 (3H,s), 4.39 (2H,s), 7.81 (1H,s).

m/z (thermospray) 319 (MH$^+$).

(b) 3-Chloroperoxybenzoic acid (50%, 1.904 g, 5.52 mmol) was added in portions to a stirred solution of 6,7-dichloro-2,3-dimethoxy-5-methylthiomethylquinoxaline (step (a), 800mg, 2.51 mmol) in dry dichloromethane (30 ml) at room temperature under nitrogen. The mixture was stirred for 30 minutes and was then quenched with 10% aqueous sodium sulphite solution and the organic layer separated. The dichloromethane solution was washed with 10% aqueous potassium carbonate solution, dried (MgSO$_4$) and concentrated under reduced pressure to leave (6,7-dichloro-2,3-dimethoxy-quinoxalin-5-yl)methyl methyl sulphone (980mg, >100% contains some dichloromethane) as a white solid, m.p. 161°–3° C.

$^1$H NMR (300 MHz, CDCl$_3$) δ=2.92 (3H,s), 4.13 (3H,s), 4.19 (3H,s), 5.16 (2H,s), 7.94 (1H,s).

m/z (thermospray) 351 (MH$^+$).

PREPARATION 30

(6.7-Dichloro-2.3-dimethoxyquinoxalin-5-yl)methyl ethyl sulphone

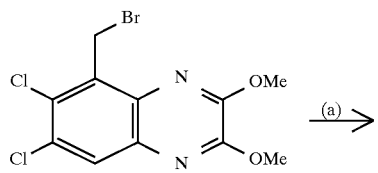

The title compound was prepared from the compound of Preparation 28 by the method of Preparation 29 (a) and (b) using sodium ethanethiolate, and was obtained as an off-white solid (31% for two steps), m.p. 150°–2° C.

$^1$H NMR (300 MHz, CDCl$_3$) δ=1.43 (3H,t,J 8 Hz), 3.08 (2H,q,J 8Hz), 4.16 (3H,s), 4.21 (3H,s), 5.14 (2H,s), 7.96 (1H,s).

m/z (thermospray) 365 (MH$^+$).

PREPARATION 31

(6.7-Dichloro-2.3-dimethoxyquinoxalin-5-yl)methyl benzyl sulphone

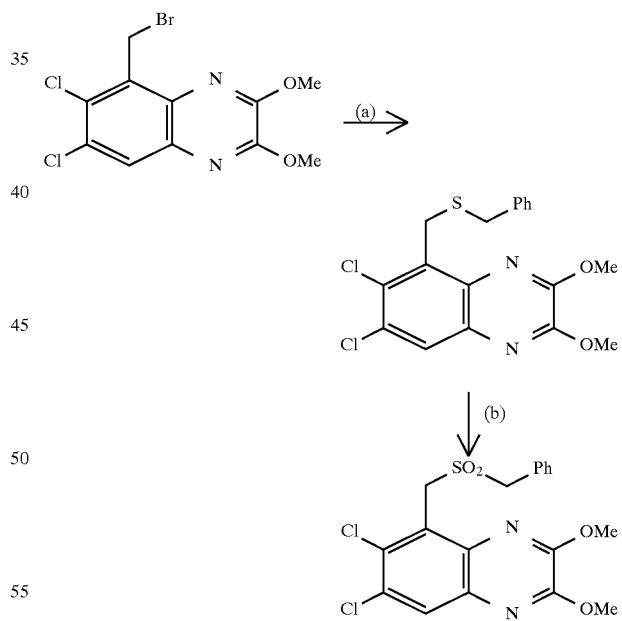

(a) Potassium carbonate (108 mg, 0.781 mmol) followed by benzyl mercaptan (92 μl, 97 mg, 0.781 mmol) were added to a stirred solution of 5-bromomethyl-6,7-dichloro-2,3-methoxyquinoxaline (Preparation 28) (250 mg, 0.71 mmol) in dry dimethylformamide (10 ml) under nitrogen at room temperature. The mixture was stirred for 30 minutes and was then partitioned between brine and ethyl acetate. The organic layer was separated and the aqueous phase was extracted twice with ethyl acetate. The combined extracts were dried (MgSO$_4$) and concentrated under reduced pressure. The residue was purified by flash chromatography (eluting with 3:1 then 2:1 hexane:dichloromethane) to give 5-benzylthiomethyl-6,7-dichloro-2,3-dimethoxyquinoxaline (268 mg, 96%) as a white solid, m.p. 121°–122° C.).

$^1$H NMR (300 MHz, CDCl$_3$) δ=3.86 (2H,s), 4.00 (3H,s), 4.14 (3H,s), 4.43 (2H,s), 7.25 (5H,m), 7.80 (1H,s).

m/z (thermospray) 395 (MH$^+$).

(b) The title compound was prepared from 5-benzylthiomethyl-6,7-dichloro-2,3-dimethoxyquinoxaline (step (a)) by the method of Preparation 29 (b) and was obtained as a white solid (93%), m.p. 185°–7° C.

$^1$H NMR (300 MHz, CDCl$_3$) δ=4.03 (3H,s), 4.12 (3H,s), 4.35 (2H,s), 5.12 (2H,s), 7.40 (5H,m), 7.93 (1H,s). m/z (thermospray) 427 (MH$^+$).

We claim:

1. A compound of formula I,

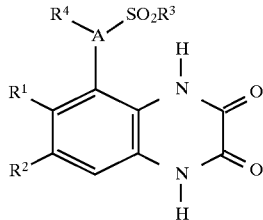

wherein

A represents N or CH;

$R^1$ and $R^2$ independently represent $C_{1-4}$ alkyl, halo or $CF_3$;

$R^3$ represents $C_{1-4}$ alkyl (optionally substituted by $C_{3-7}$ cycloalkyl or aryl), $C_{3-7}$ cycloalkyl, $CF_3$ or aryl;

$R^4$ represents H, $C_{3-7}$ cycloalkyl or $C_{1-6}$ alkyl;

$R^5$ and $R^6$ independently represent H or $C_{1-4}$ alkyl, or taken together with the nitrogen atom to which they are attached they may represent a pyrrolidino, piperidino or morpholino group; and n represents 2, 3 or 4;

or a pharmaceutically acceptable salt thereof.

2. A compound as claimed in claim 1, wherein A represents N.

3. A compound as claimed in claim 1, wherein $R^1$ represents halo or $C_{1-4}$ alkyl.

4. A compound as claimed in claim 1, wherein $R^2$ represents halo or $C_{1-4}$ alkyl.

5. A compound as claimed in claim 1, wherein $R^3$ represents $C_{1-4}$ alkyl.

6. A compound as claimed in claim 5, wherein $R^3$ represents methyl.

7. A compound as claimed in claim 1, wherein $R^4$ represents $C_{1-6}$ alkyl substituted by OH or $CO_2H$.

8. A compound as claimed in claim 7, wherein $R^4$ represents $CH_2CH_2OH$ or $CH_2CO_2H$.

9. A compound as claimed in claim 2, wherein the chirality of the bond between the nitrogen atom represented by A and the 1,4-dihydro-2,3-dioxoquinoxaline ring is as shown in formula IA,

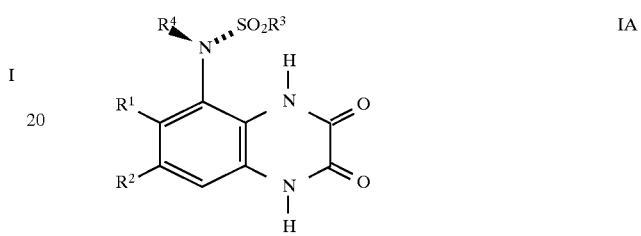

wherein $R^{1-4}$ are as defined in claim 1.

10. A compound as claimed in any claim 1, which is (R)-N-(1,4-dihydro-6,7-dichloro-2,3-dioxoquinoxalin-5-yl)-N-(2-hydroxyethyl)methane-sulphonamide.

11. A compound as claimed in claim 1, which is (R)-N-(carboxymethyl)-N-(1,4-dihydro-6,7-dichloro-2,3-dioxoquinoxalin-5-yl)methane-sulphonamide.

12. A pharmaceutical composition comprising a compound of the formula (I), or a pharmaceutically acceptable salt thereof, as claimed according to claim 1, together with a pharmaceutically acceptable carrier or diluent.

13. The method of treating neurodogenerative disorder in a patient in need of such treatment, which comprises administering to said afflicted subject a therapeutically-effective amount of a compound of the formula (I), or a pharmaceutically acceptable salt thereof, as claimed in claim 1.

* * * * *

UNITED STATES PATENT AND TRADEMARK OFFICE
CERTIFICATE OF CORRECTION

PATENT NO : 5,852,016
DATED : December 22, 1998
INVENTOR(S) : Michael J. Fray et al.

It is certified that error appears in the above-identified patent and that said Letters Patent is hereby corrected as shown below:

In claim 1, line 34, in the definition of $R^4$, after "$C_{1-6}$ alkyl," please insert the following passage encomapssed by square brackets, viz., -- [optionally substituted by OH, $C_{1-4}$ alkoxy, aryl (optionally substituted by up to 3 substituents independently selected from $C_{1-4}$ alkyl, $C_{1-4}$ alkoxy, halo and $CF_3$), heterocyclyl (optionally substituted by up to 3 substituents independently selected from $C_{1-4}$ alkyl, $C_{1-4}$ alkoxy, OH, halo, $CF_3$ and oxo and optionally benzo-fused), $C_{2-6}$ alkenyl, $C_{2-6}$ alkynyl $C_{2-6}$ alkanoyl, $CO_2H$, $C_{1-4}$ alkoxycarbonyl, $NH_2$, $C_{1-4}$ alkylamino, di($C_{1-4}$ alkyl)amino, $NHSO_2CF_3$, $CONR^5R^6$, $NHCONR^5R^6$ or $O(CH_2)_nNR^5R^6$] --.

Signed and Sealed this

Eleventh Day of May, 1999

Q. TODD DICKINSON

*Attest:*

*Attesting Officer*     *Acting Commissioner of Patents and Trademarks*